US012584916B2

(12) United States Patent
Roux et al.

(10) Patent No.: US 12,584,916 B2
(45) Date of Patent: Mar. 24, 2026

(54) METHOD FOR MEASURING THE MODULATION OF THE ACTIVATION OF A G PROTEIN-COUPLED RECEPTOR WITH GTP ANALOGUES

(71) Applicants: CISBIO BIOASSAYS, Codolet (FR); CENTRE NATIONAL DE LA RECHERCHE SCIENTIFIQUE, Paris (FR)

(72) Inventors: Thomas Roux, Nîmes (FR); Eric Trinquet, Pont-Saint-Esprit (FR); Elodie Dupuis, Caissargues (FR); Sara Bdioui, Sérignan du Comtat (FR); Jean-Philippe Pin, Montpellier (FR); Philippe Rondard, Saint-Gély-du-Fesc (FR)

(73) Assignees: CISBIO BIOASSAYS, Codolet (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 1272 days.

(21) Appl. No.: 17/426,571

(22) PCT Filed: Jan. 30, 2020

(86) PCT No.: PCT/FR2020/050151
§ 371 (c)(1),
(2) Date: Jul. 28, 2021

(87) PCT Pub. No.: WO2020/157441
PCT Pub. Date: Aug. 6, 2020

(65) Prior Publication Data

US 2022/0099669 A1 Mar. 31, 2022

(30) Foreign Application Priority Data

Jan. 30, 2019 (FR) ...................................... 1900880

(51) Int. Cl.
*G01N 33/566* (2006.01)
*G01N 33/542* (2006.01)

(52) U.S. Cl.
CPC ......... *G01N 33/566* (2013.01); *G01N 33/542* (2013.01); *G01N 2333/4719* (2013.01); *G01N 2333/726* (2013.01); *G01N 2500/02* (2013.01)

(58) Field of Classification Search
CPC ......... G01N 33/542; G01N 2333/4719; G01N 2333/726; G01N 2500/02
See application file for complete search history.

(56) References Cited

FOREIGN PATENT DOCUMENTS

| | | | | |
|---|---|---|---|---|
| WO | 2004/035614 A1 | | 4/2004 | |
| WO | WO-2009033743 A1 | * | 3/2009 | ............ C07K 16/18 |
| WO | 2010/125314 A1 | | 11/2010 | |
| WO | 2011/018586 A2 | | 2/2011 | |

OTHER PUBLICATIONS

Mariuzza (Annu. Rev. Biophys. Biophys. Chem., 16: 139-159, 1987) (Year: 1987).*
McCarthy et al. (J. Immunol. Methods, 251(1-2): 137-149, 2001) (Year: 2001).*
Lin et al. (African Journal of Biotechnology, 10(79):18294-18302, 2011) (Year: 2011).*
Bowie et al. (Science, 247:1306-1310, 1990) (Year: 1990).*
Whisstock et al. (Quarterly Reviews in Biophysics. 36(3):307-340, 2007) (Year: 2007).*
Lazar et al. (Molecular and Cellular Biology. 1988; 8(3): 1247-1252) (Year: 1988).*

(Continued)

*Primary Examiner* — Gregory S Emch
*Assistant Examiner* — Ashley H. Gao
(74) *Attorney, Agent, or Firm* — MH2 Technology Law Group, LLP

(57) ABSTRACT

The invention relates to a method for determining the ability of a molecule to modulate the activation of a G protein-coupled receptor (GPCR), said method comprising the following steps:

a) introducing, in a first container:
 a membrane preparation bearing one or more GPCRs and one or more alpha G-proteins,
 a source of nonhydrolyzable or slowly hydrolyzable GTP labeled with a first member of a pair of RET partners,
 a ligand of the alpha subunit of a G protein (alpha G-protein) labeled with a second member of the pair of RET partners, said ligand being capable of binding to the full alpha G-protein bound to the nonhydrolyzable or slowly hydrolyzable GTP labeled with the first member of a pair of RET partners,
 optionally a GPCR agonist;
b) measuring the RET signal emitted in the first container;
c) introducing (i) in a second container, the same reagents as in step a) and the molecule to be assayed or (ii) in the first container, the molecule to be assayed;
d) measuring the RET signal emitted in the second container or in the first container obtained in step c);
e) comparing the signals obtained in steps b) and d), a modulation of the signal obtained in step d) relative to that obtained in step b) indicating that the molecule to be tested is capable of modulating the activation of the GPCR.

16 Claims, 28 Drawing Sheets

Specification includes a Sequence Listing.

(56) References Cited

OTHER PUBLICATIONS

Dacres et al (Effect of enhanced Renilla luciferase and fluorescent protein variants on the Foster distance of Bioluminescence resonance energy transfer (BRET), https://doi.org/10.1016/j.bbrc.2012.07.133 (2012)) (Year: 2012).*
Scholler et al ( "Time-Resolved Forster Resonance Energy Transfer-Based Technologies to Investigate G Protein-Coupled Receptor Machinery: High-Throughput Screening Assays and Future Development", In: Progess in Molecular Biology and Translational Science, 2013, vol. 113, pp. 275-312). (Year: 2013).*
Registry (Answers 17 and 18 of L44 as retrieved by STIC (available to the public as of 2009, as evidenced by STIC)). (Year: 2009).*
J. Vuojola et al., 81 Analytical Chemistry, 5033-5038 (2009) (Year: 2009).*
Geißler et al., 1 Current Inorganic Chemistry, 17-35 (2011) (Year: 2011).*
Q. Wang et al., 52 Inorganic Chemistry, 8461-8456 (2013) (Year: 2013).*
U.S. Appl. No. 17/796,375, filed 2021.*
U.S. Appl. No. 17/427,200, filed 2021.*
H. Takalo, 5 Bioconjugate Chemistry, 278-282 (1994) (Year: 1994).*
Johnston et al ("Minimal Determinants for Binding Activated Ga from the Structure of a Gail-Peptide Dimer". Biochemistry, vol. 45, No. 38, Sep. 1, 2006, pp. 11390-11400, XP055457282, US ISSN: 0006-2960, DOI: 10.1{021/bi061 3832) (Year: 2006).*
Al Qaraghuli et al. (2020, Nature Scientific Reports 10:13969) (Year: 2020).*
Rabia, et al. (2018, Biochemical Engineering Journal 137:365-374) (Year: 2018).*
Tiller et al (2017, J. Biol. Chem. (2017) 292(40) 16638-16652) (Year: 2017).*
Tsuji et al (2022, J Virol 96:e00071-22) (Year: 2022).*
International Search Report dated Jun. 12, 2020 and Written Opinion of the International Searching Authority for International Application No. PCT/FR2020/050151 (Authorized officer, Murielle Giry), 15 pages.
Maurel, D. et al., "Cell-surface protein-protein interaction analysis with time-resolved FRET and snap-tag technologies: Application to GPCR oligomerization," Nature Meth., vol. 5, No. 6, Jun. 2008, pp. 561-567. XP002556321.
Cottet, M. et al., "Fluorescent ligands to investigate GPCR binding properties and oligomerization," Biochem. Soc. Trans., vol. 41, No. 1, Jan. 29, 2013, pp. 148-153.

* cited by examiner

[Fig. 1]
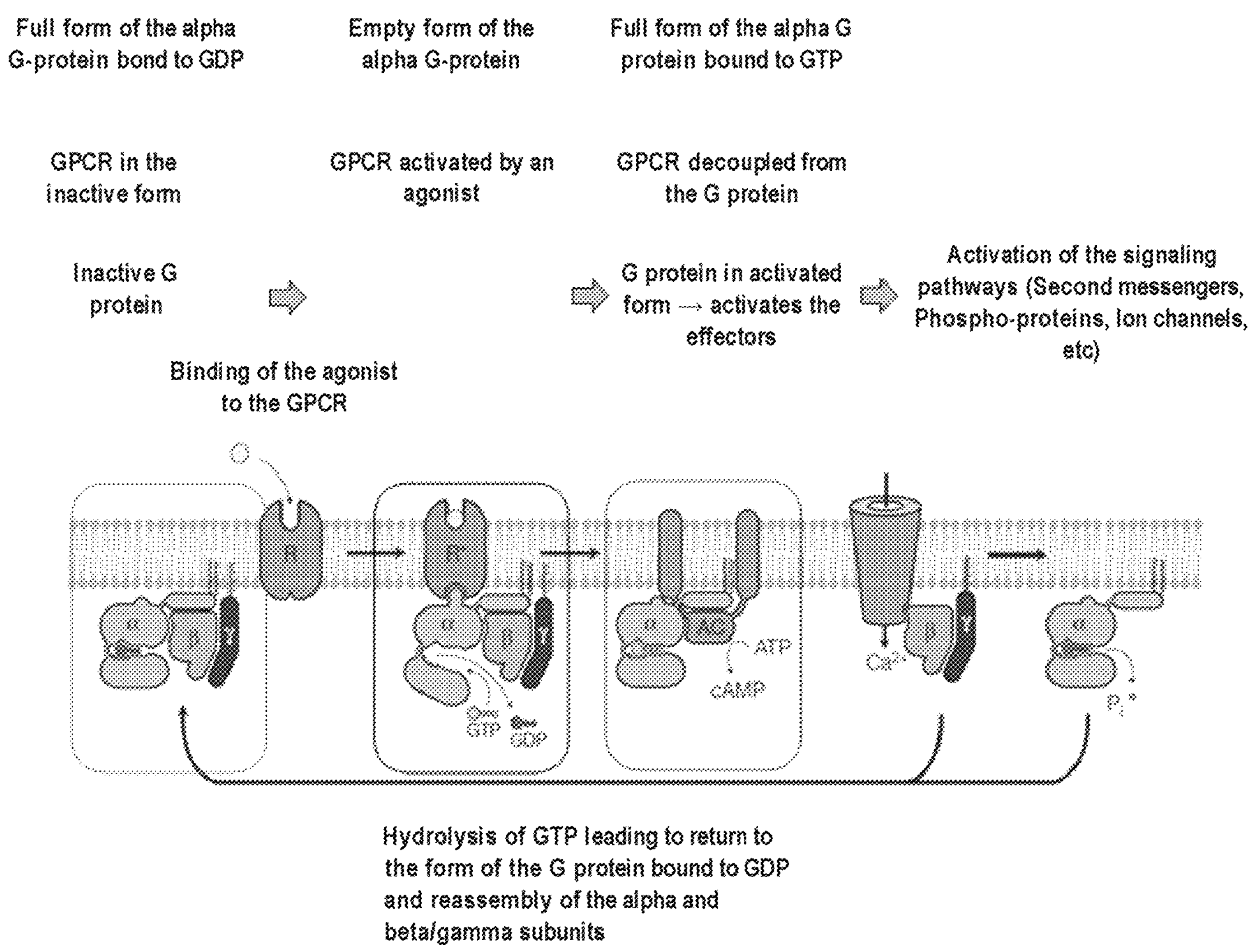

[Fig. 2A-2B]
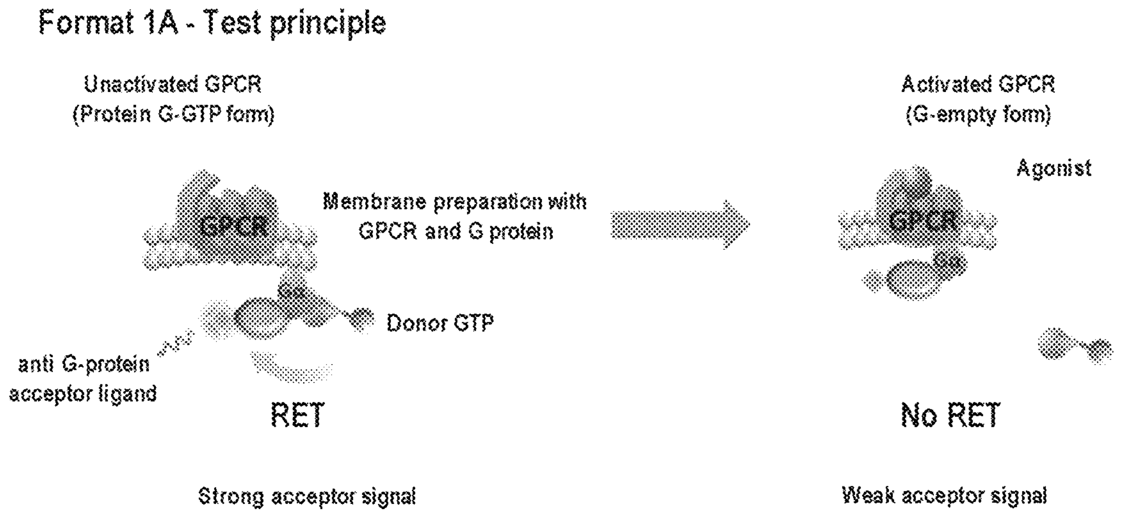
2A
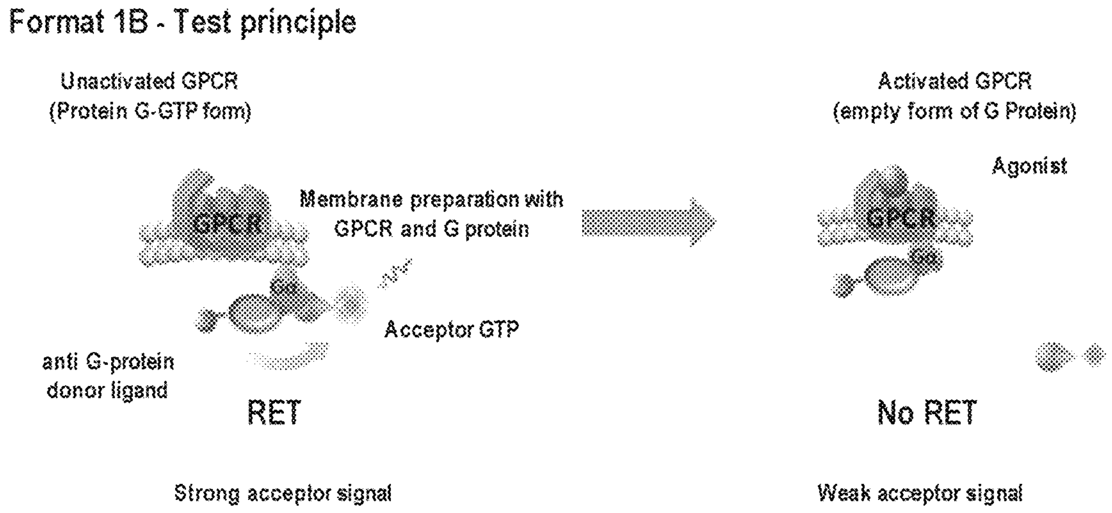
2B

[Fig. 2C-2D]
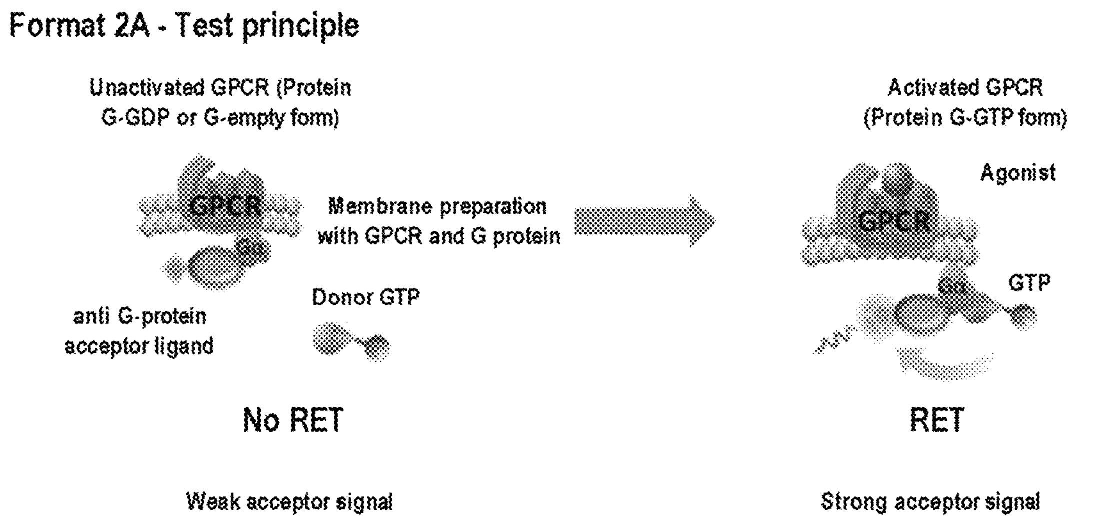
2C
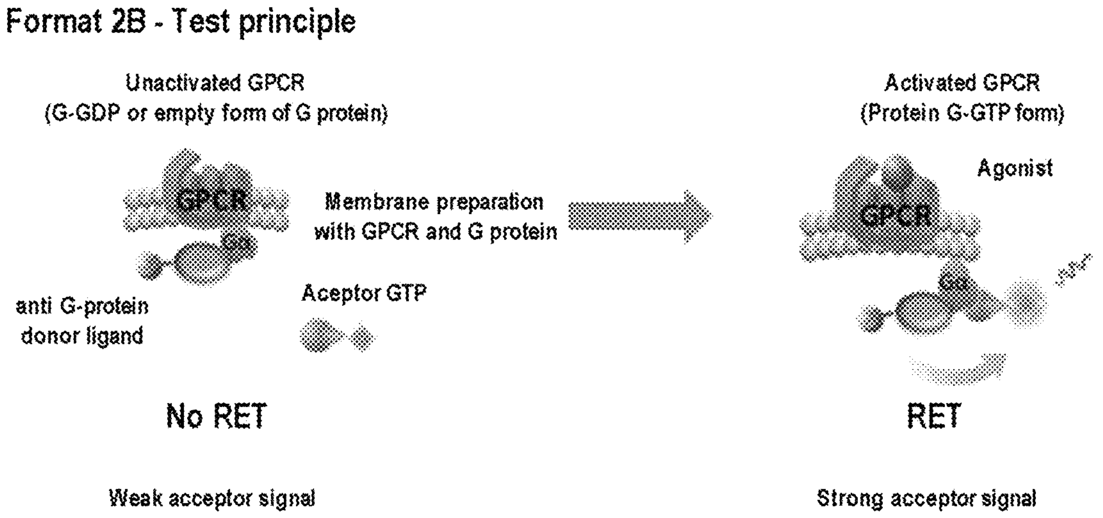
2D

[Fig. 3A-3B]
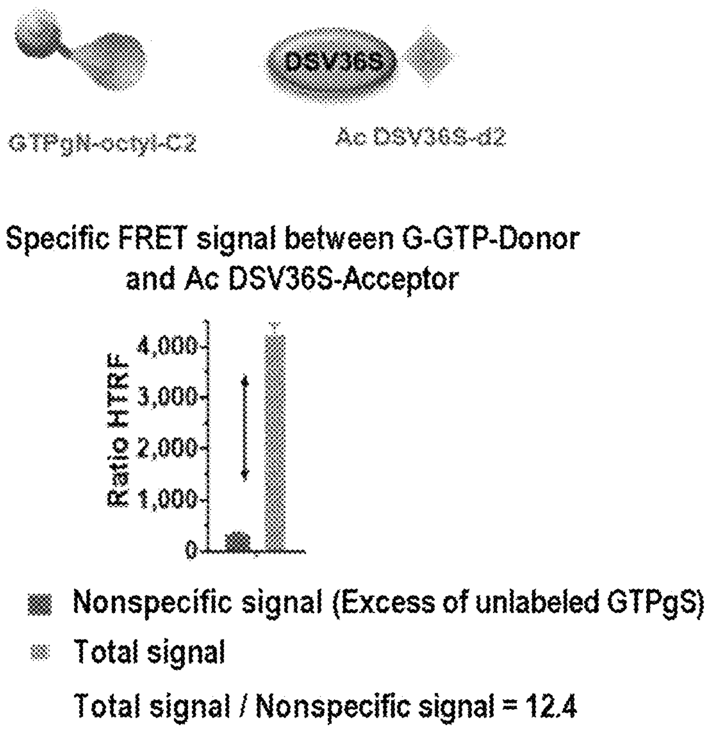
3A
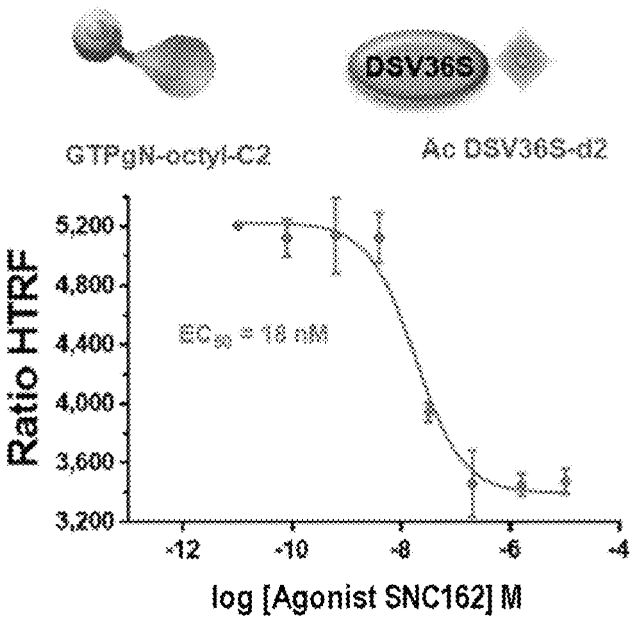
3B

[Fig. 4A-4B]
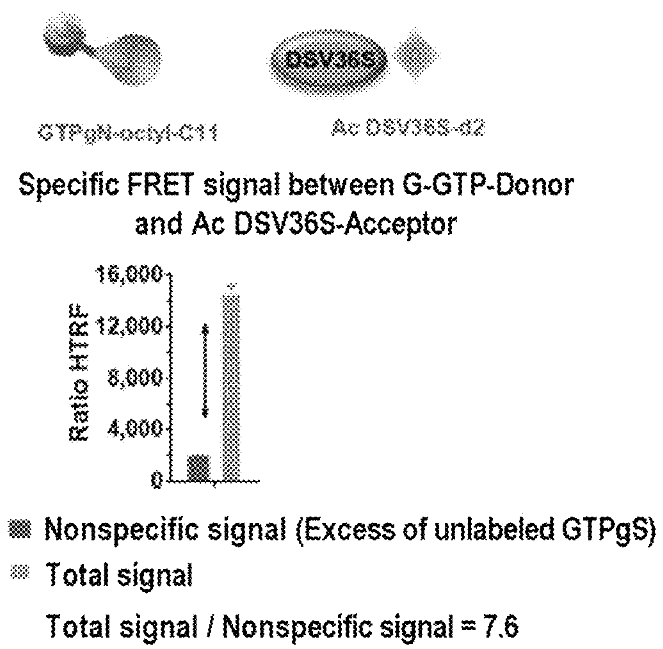
4A
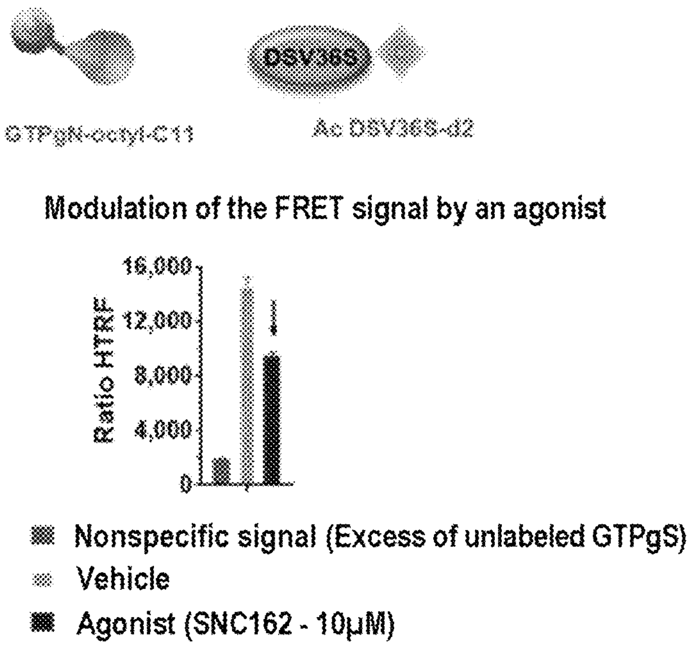
4B

[Fig. 5A-5B]
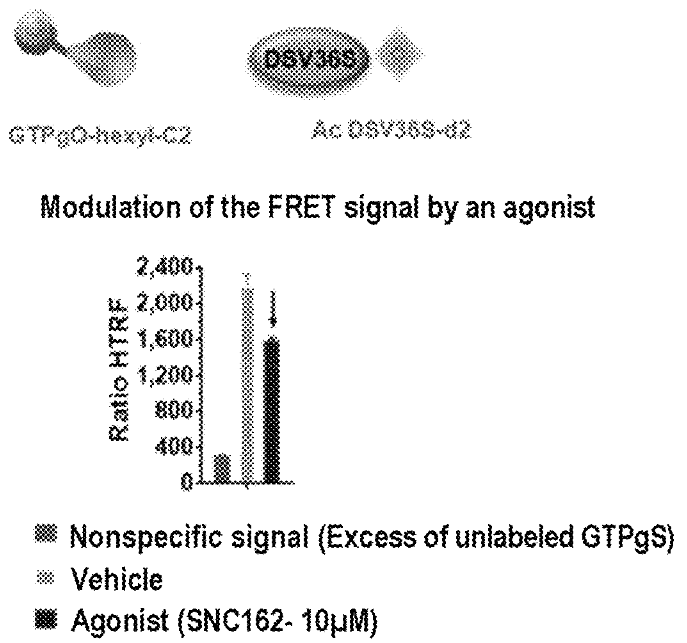
5A
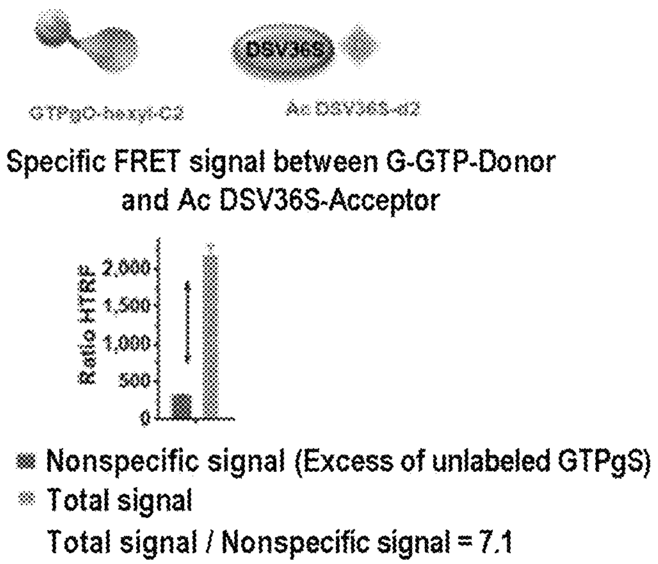
5B

[Fig. 6A-6B]
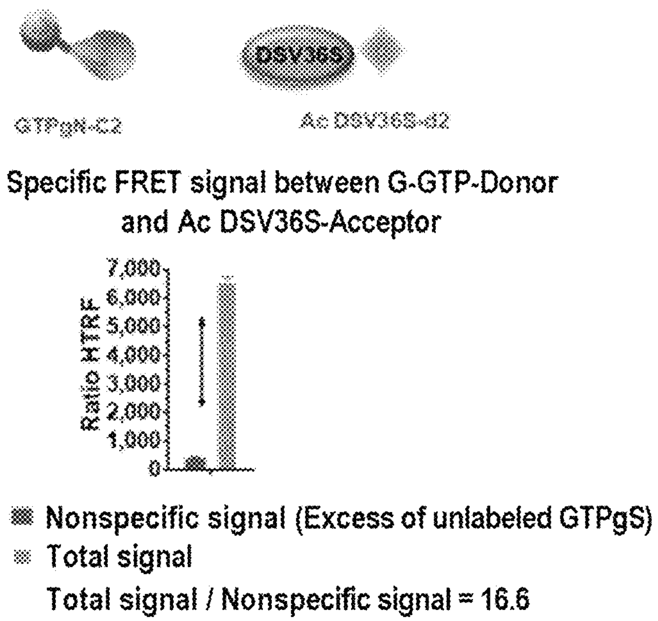
6A
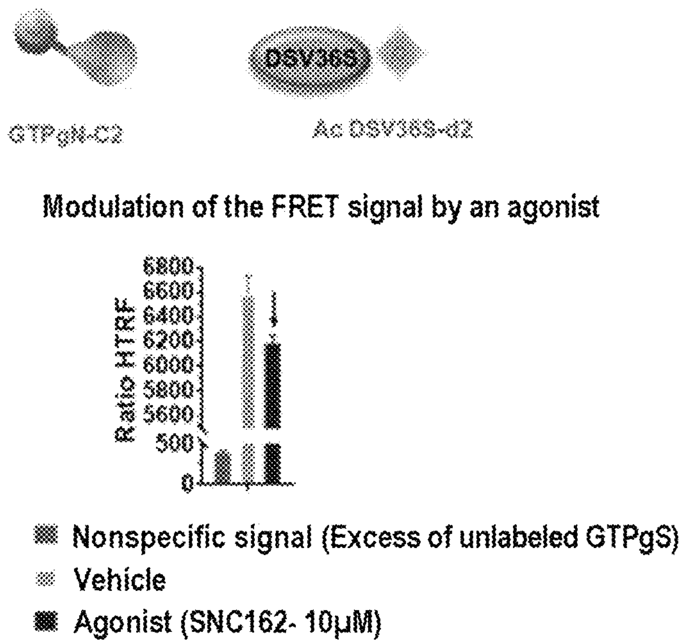
6B

[Fig. 7A-7B]
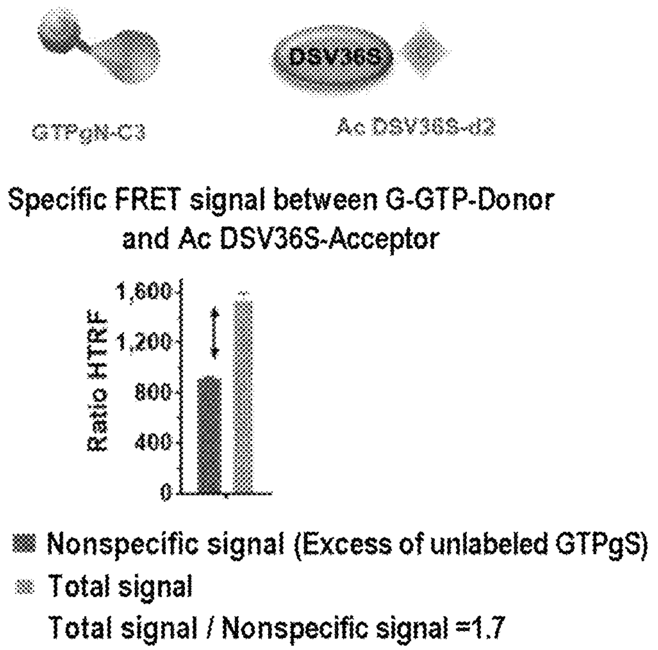
7A
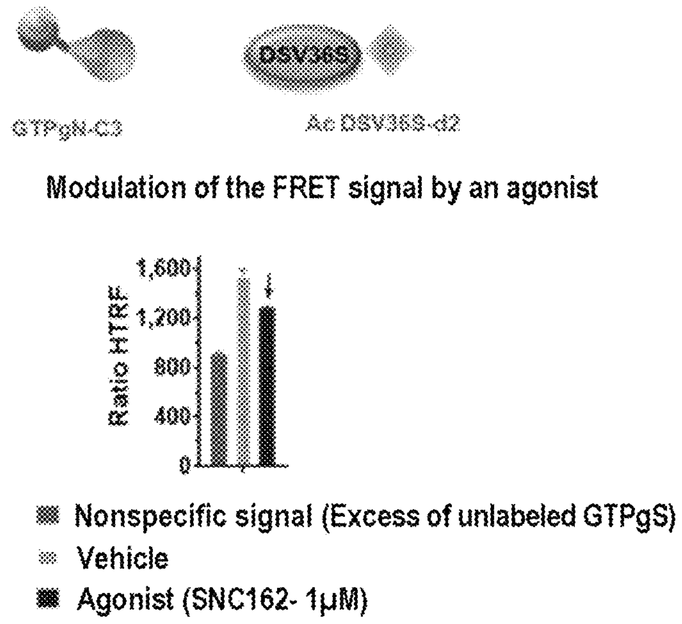
7B

[Fig. 8]
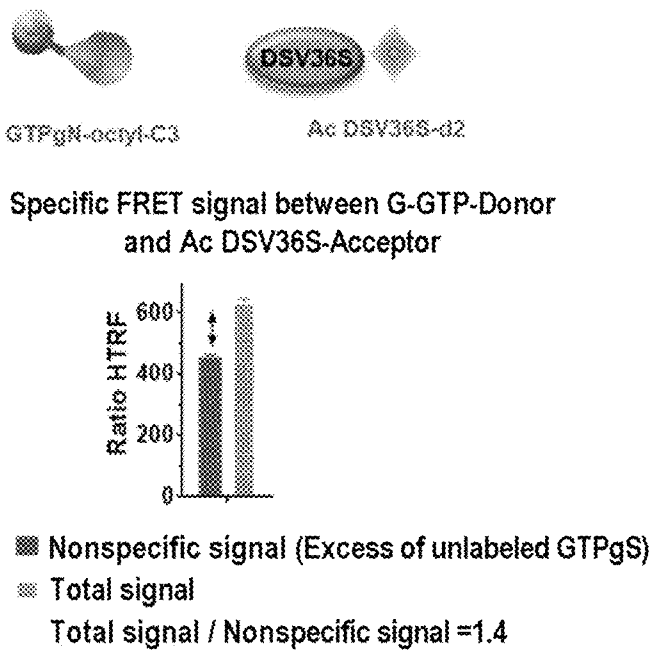

[Fig. 9]
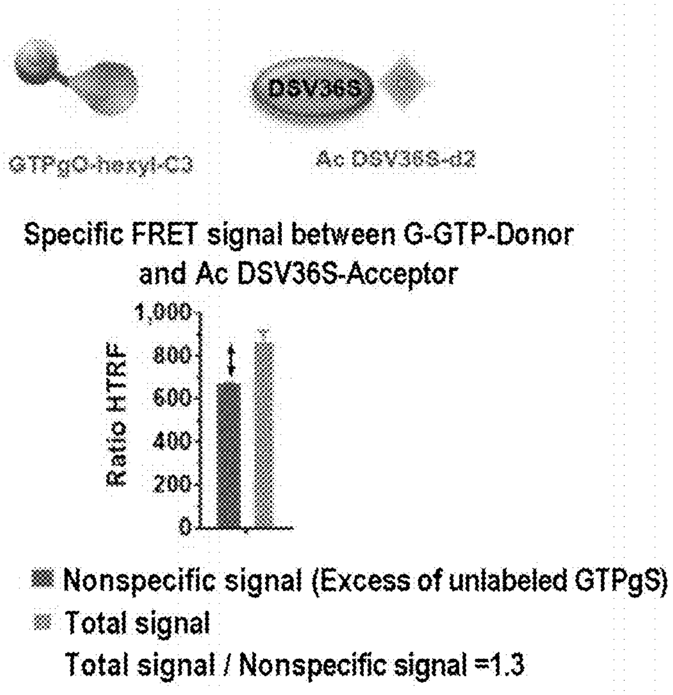

[Fig. 10A-10B]
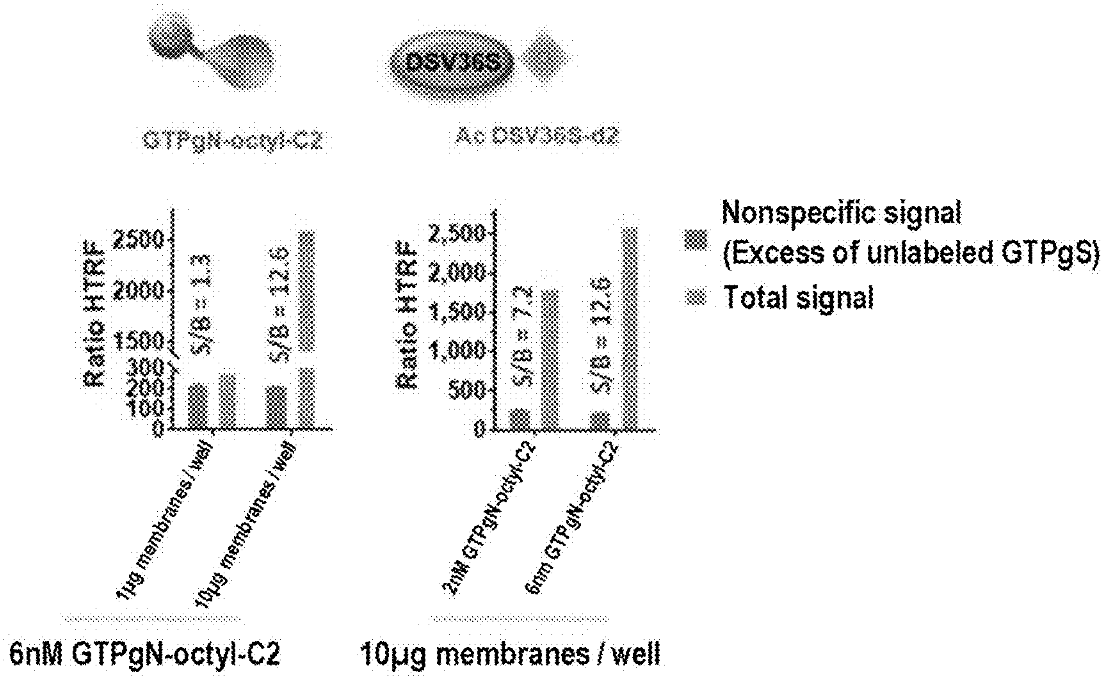
10A
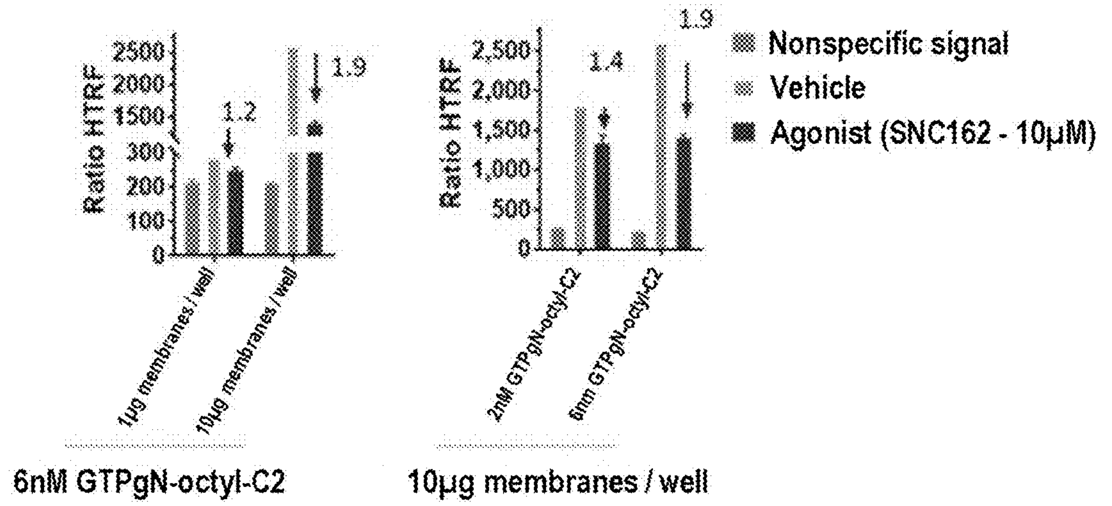
10B

[Fig. 11A-11B]
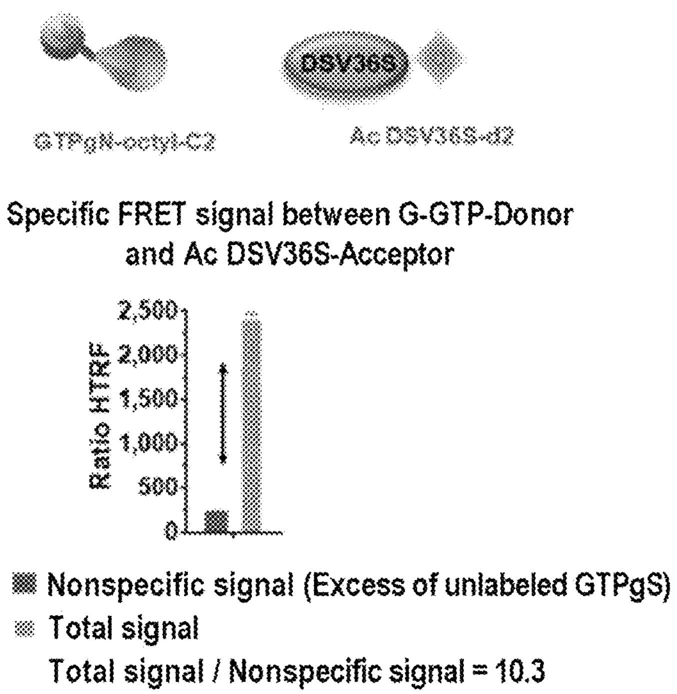
11A
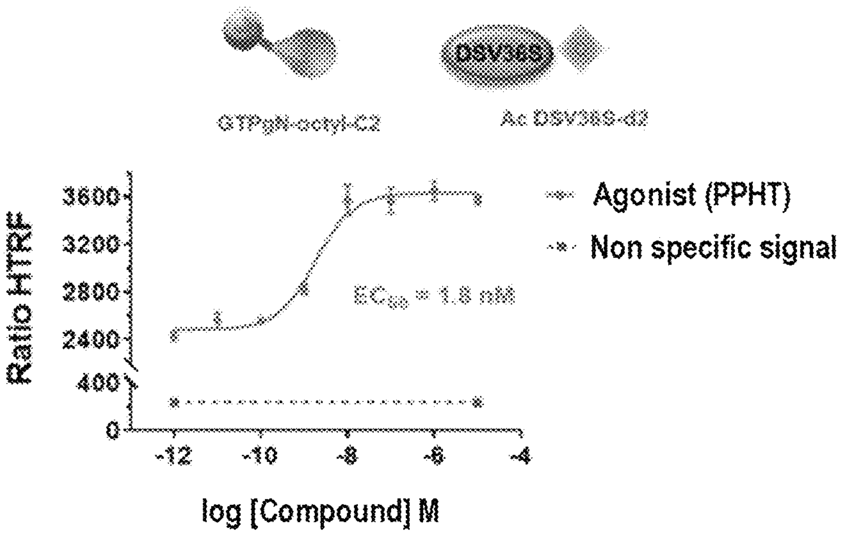
11B

[Fig. 12A-12B]
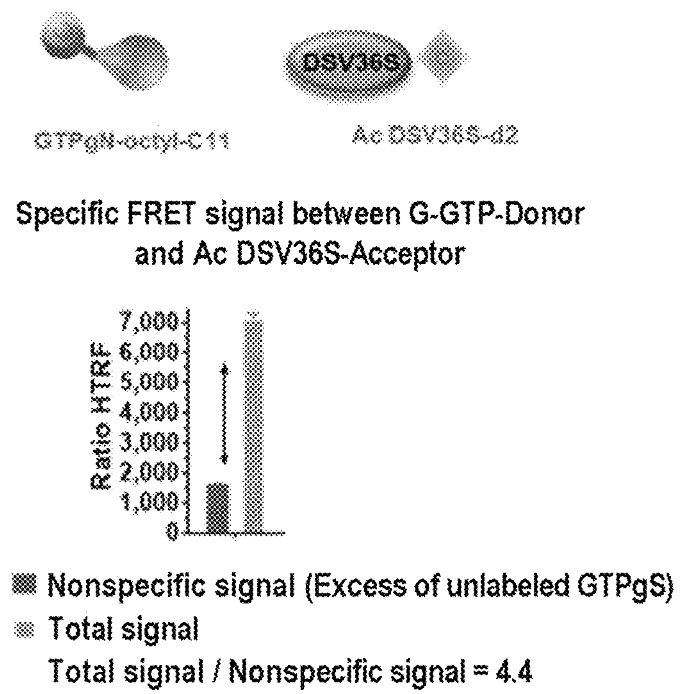
12A
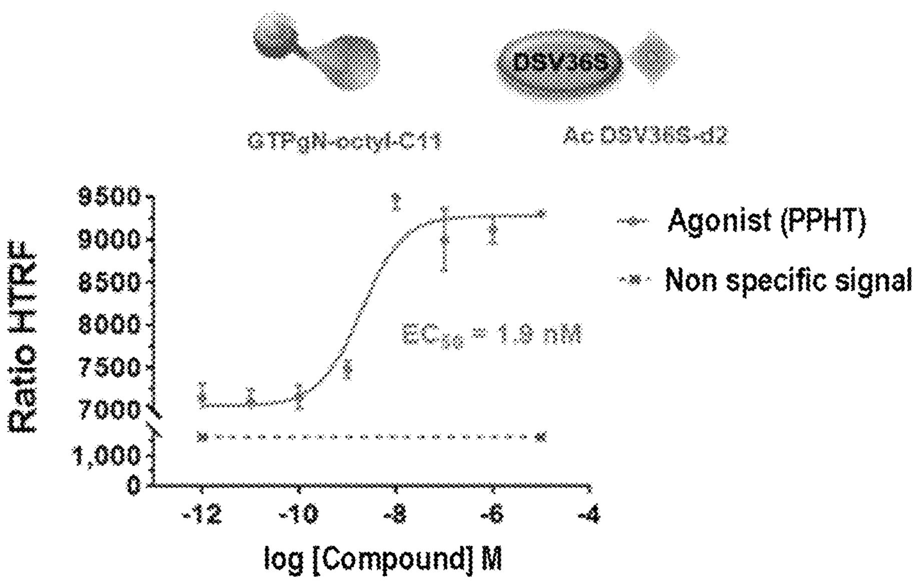
12B

[Fig. 13A-13B]
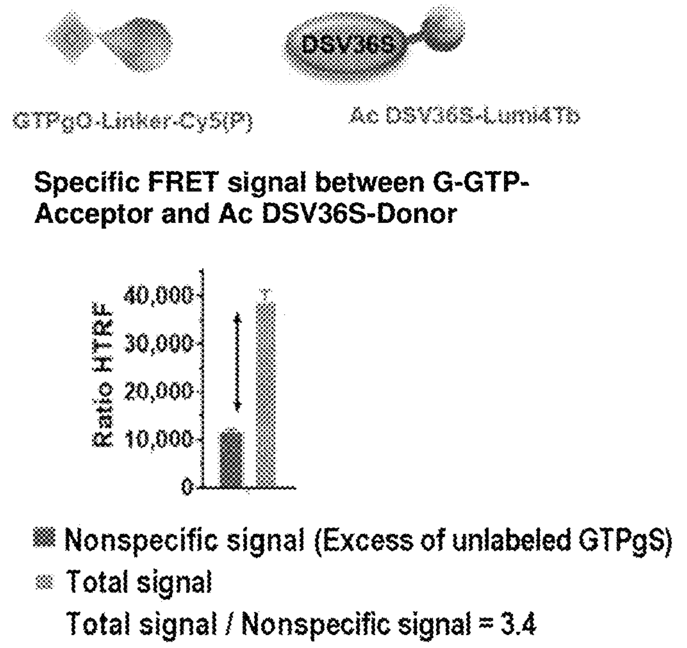
13A
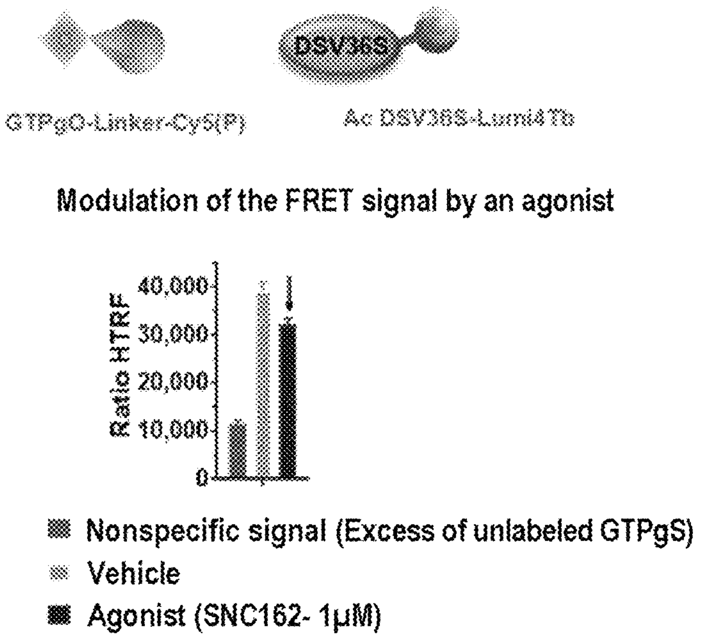
13B

[Fig. 14A-14B]
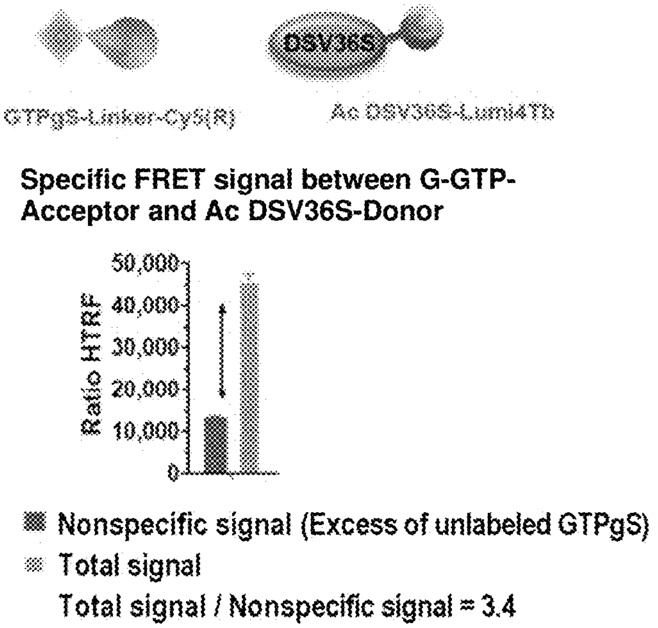
14A
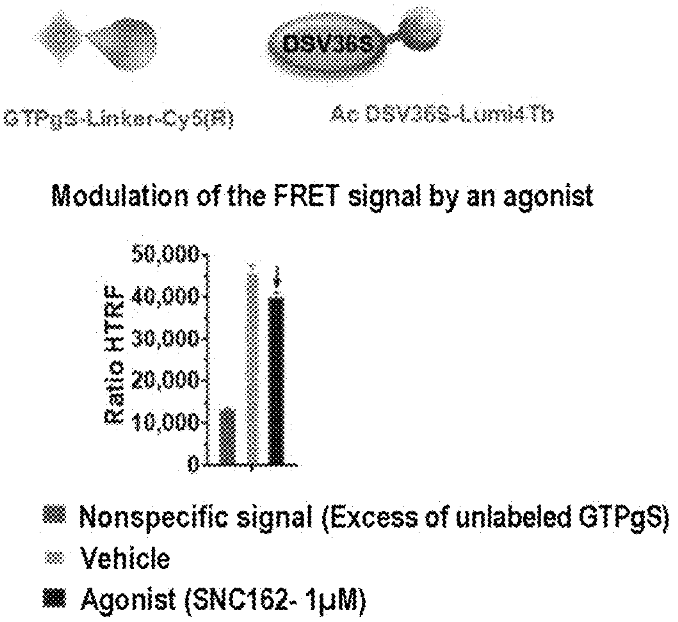
14B

[Fig. 15A-15B]
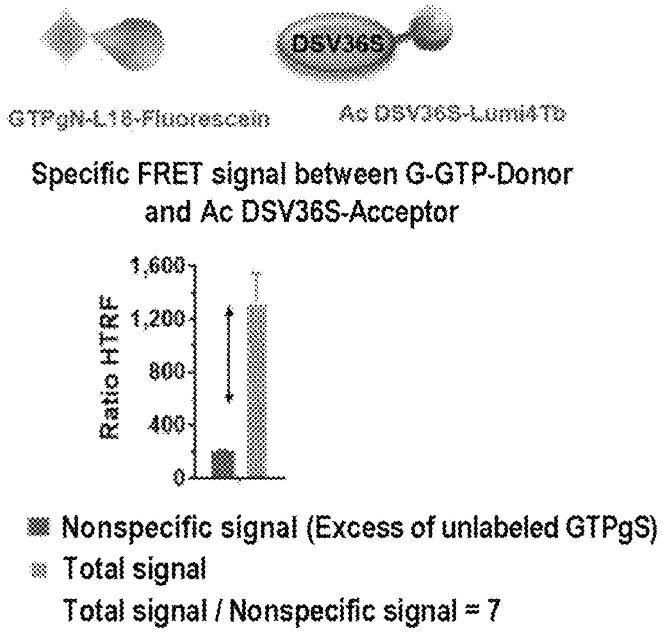
15A
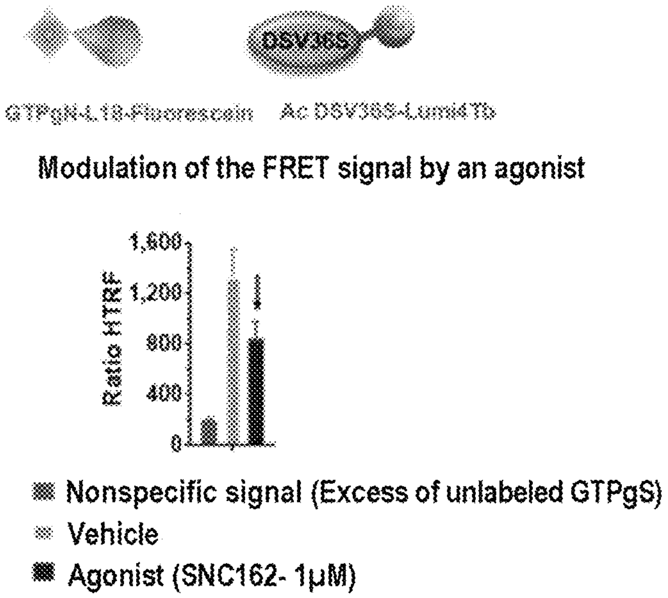
15B

[Fig. 16A-16B]
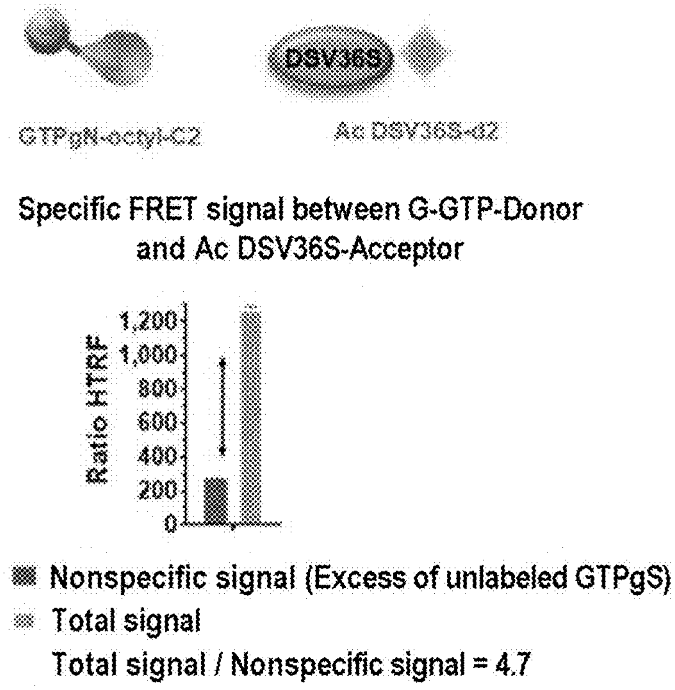
16A
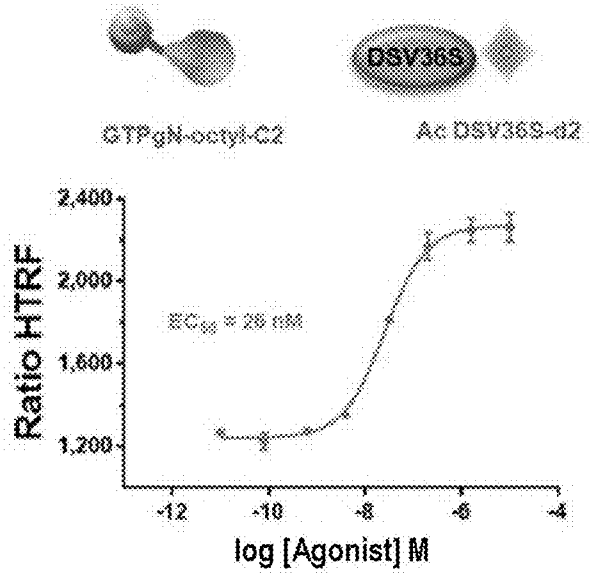
16B

[Fig. 17A-17B]
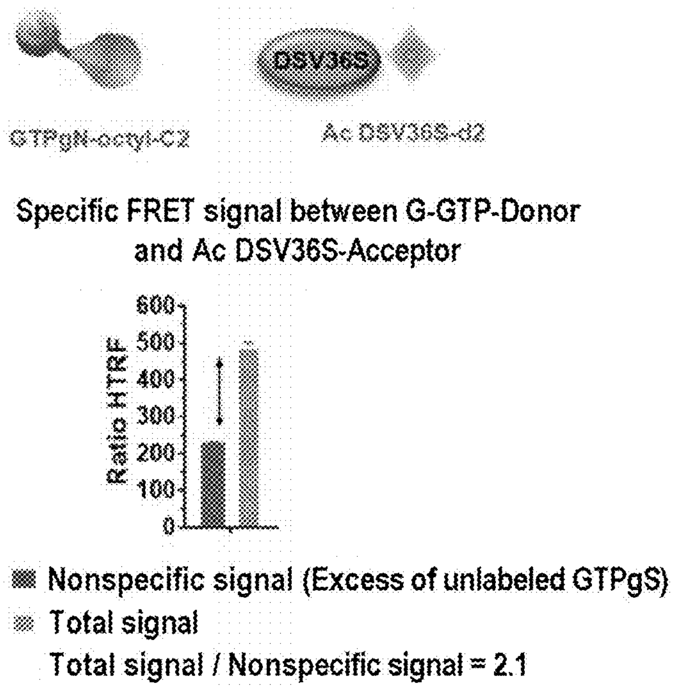
17A
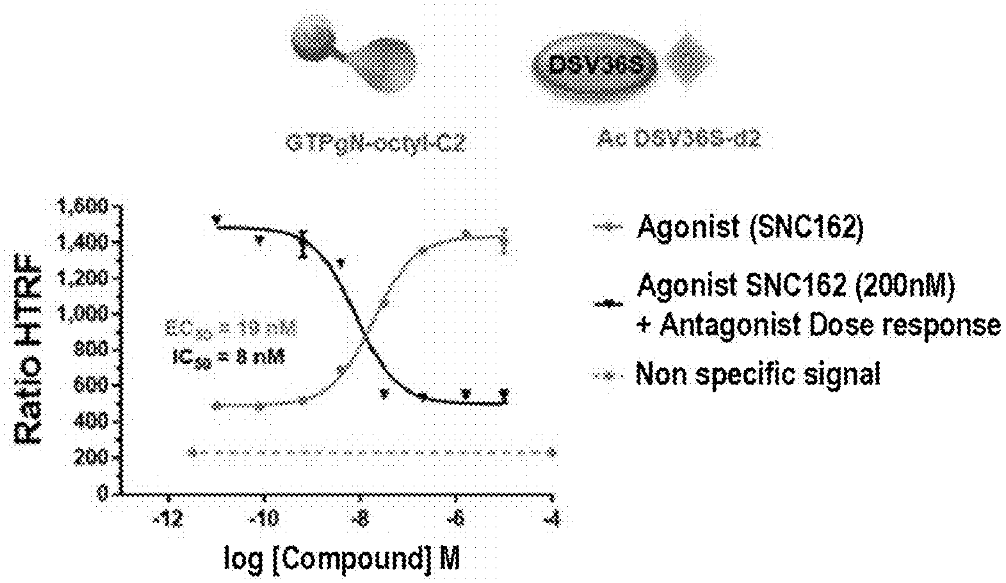
17B

[Fig. 18A-18B]
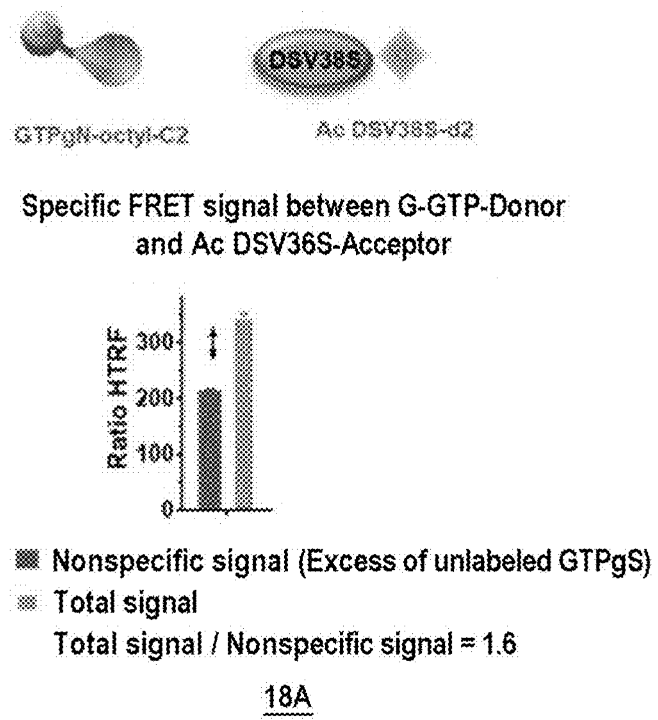
18A
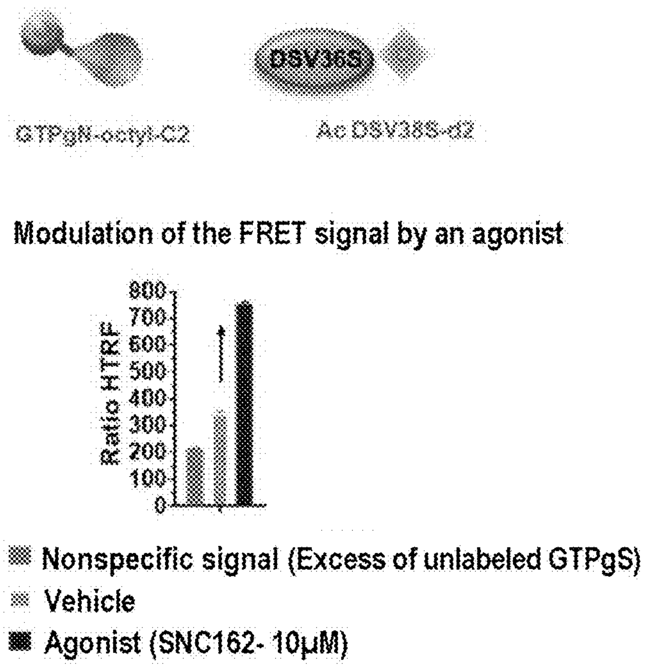
18B

[Fig. 19A-19B]
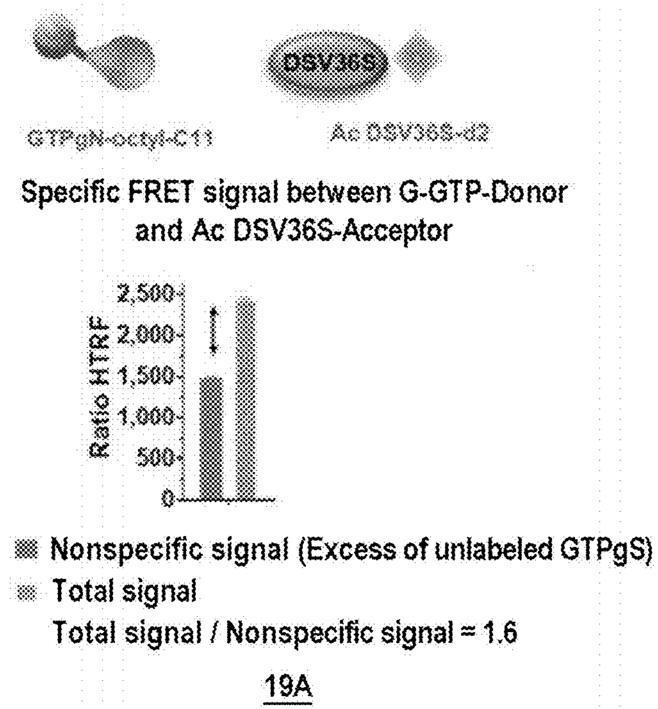
19A
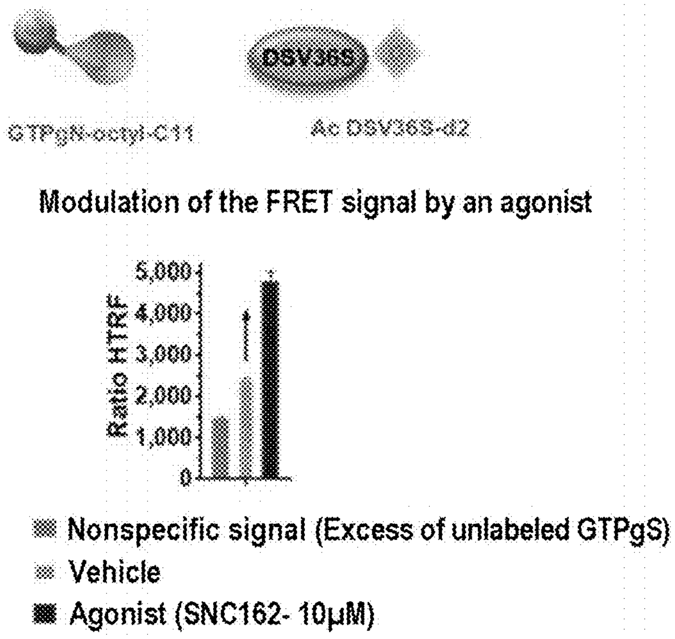
19B

[Fig. 20A-20B]
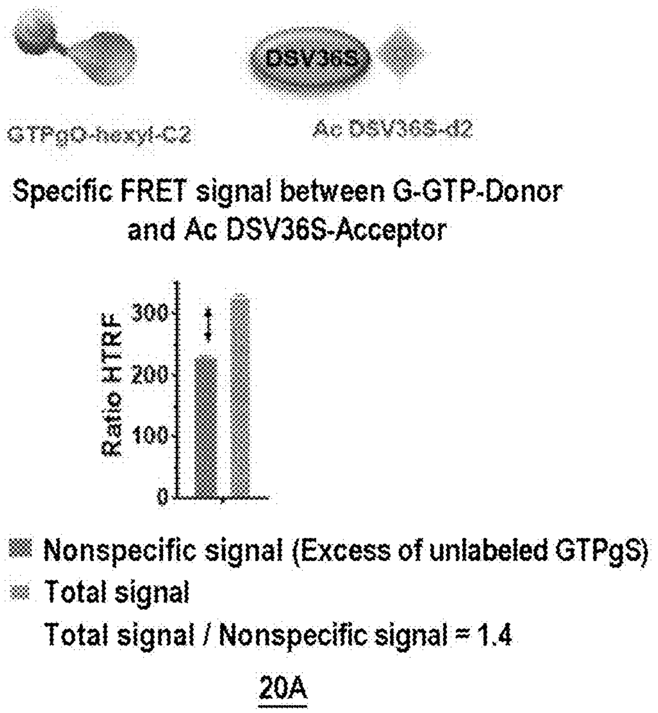
20A
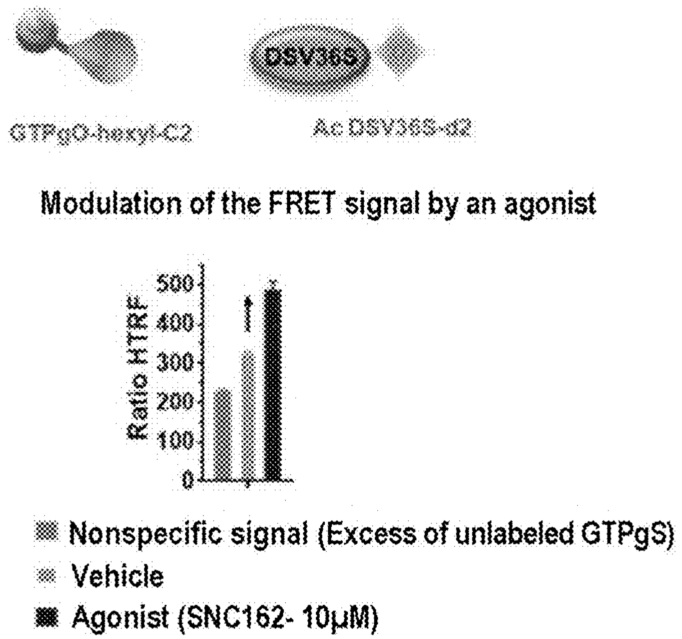
20B

[Fig. 21A-21B]
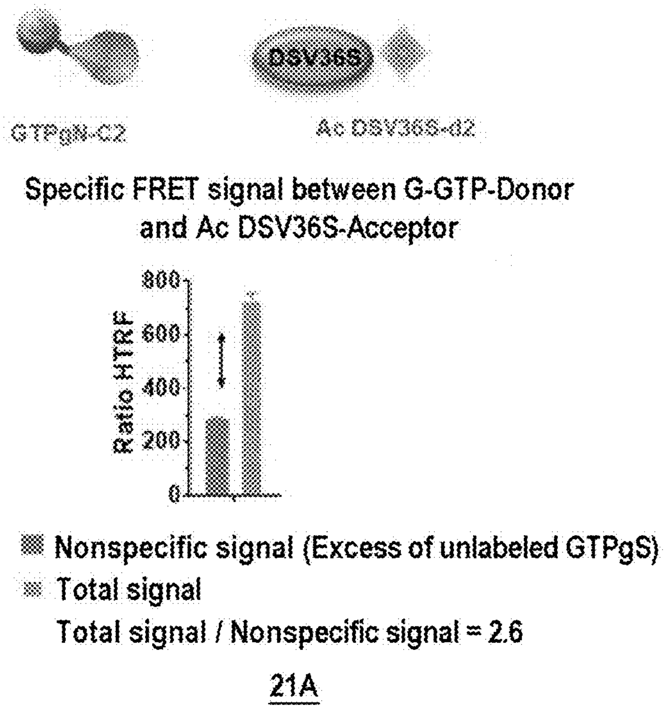
21A
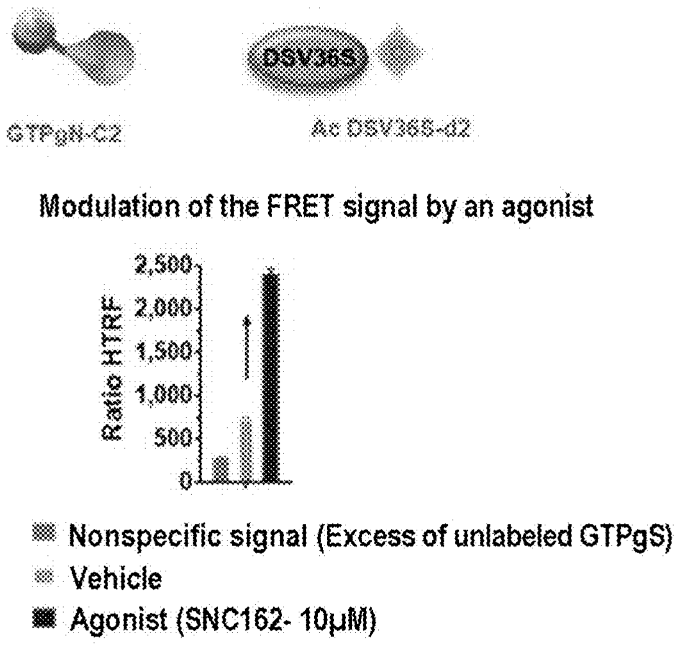
21B

[Fig. 22A-22B]
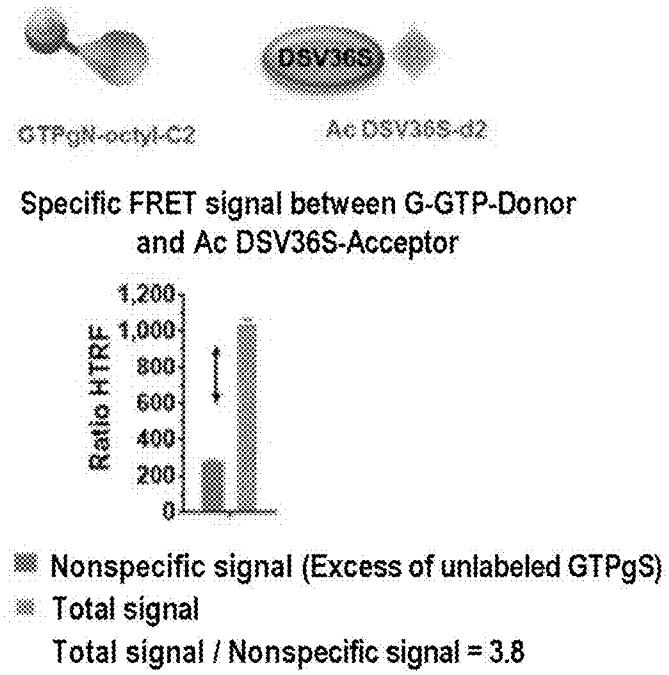
22A
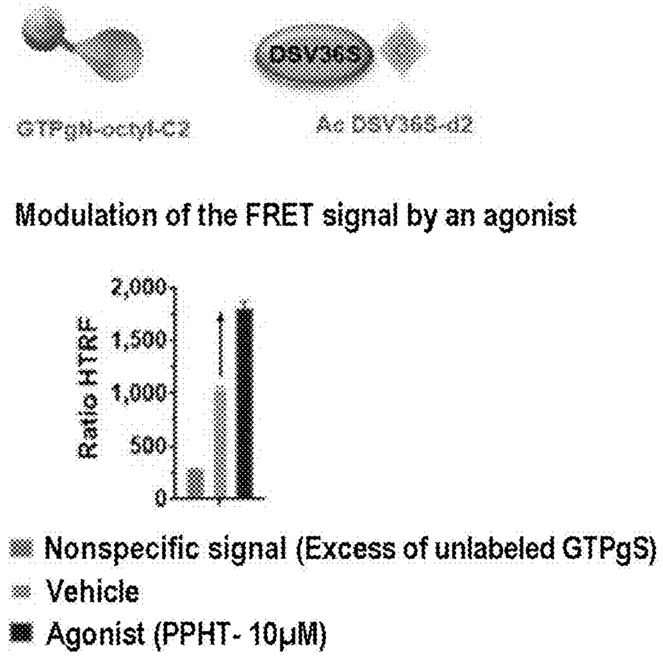
22B

[Fig. 23A-23B]
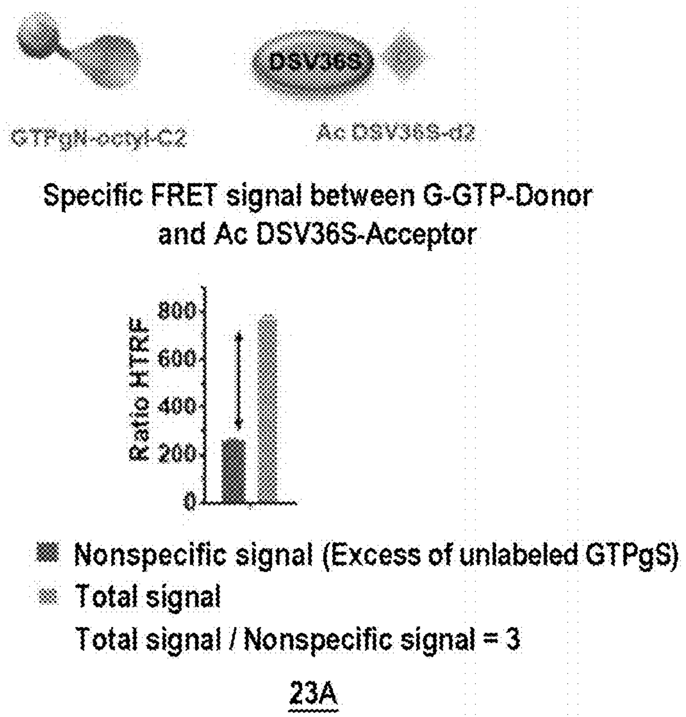
23A
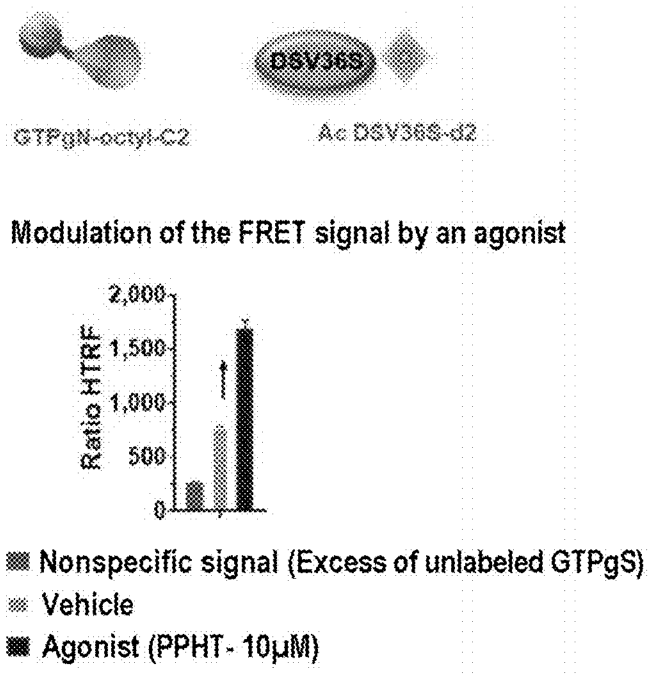
23B

[Fig. 24A-24B]
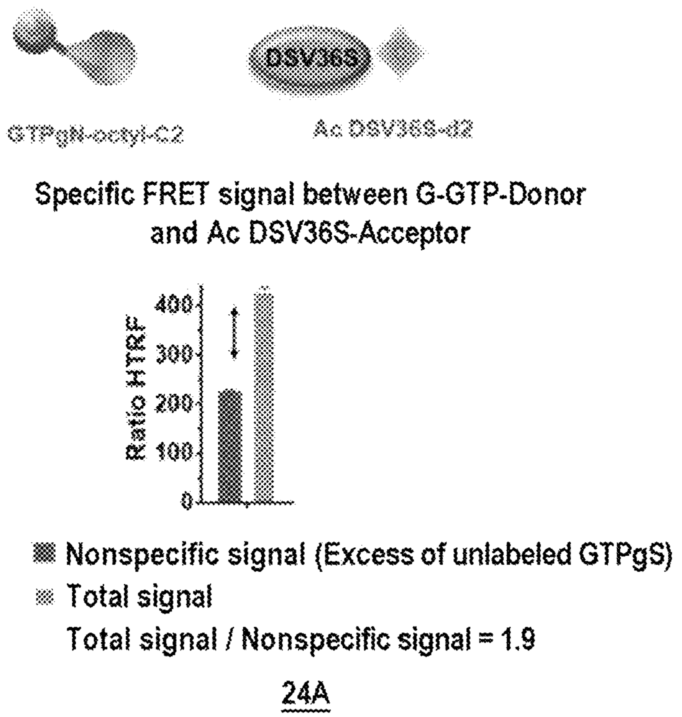
24A
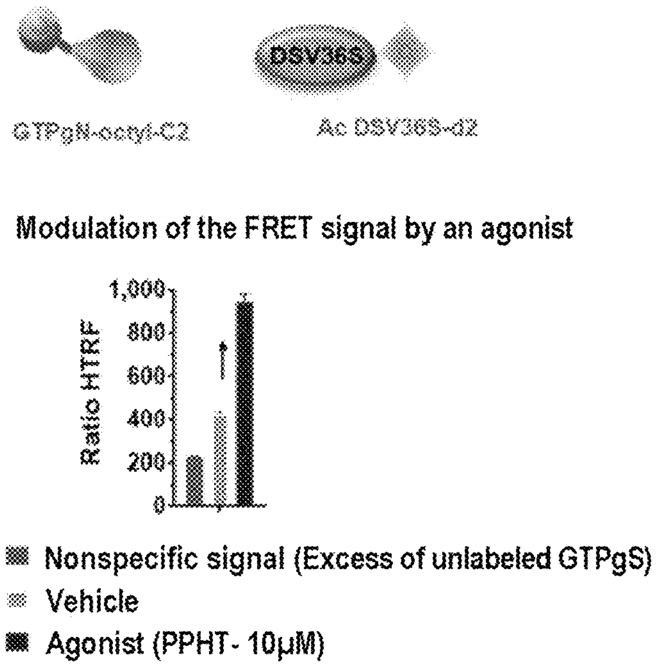
24B

[Fig. 25A-25B]
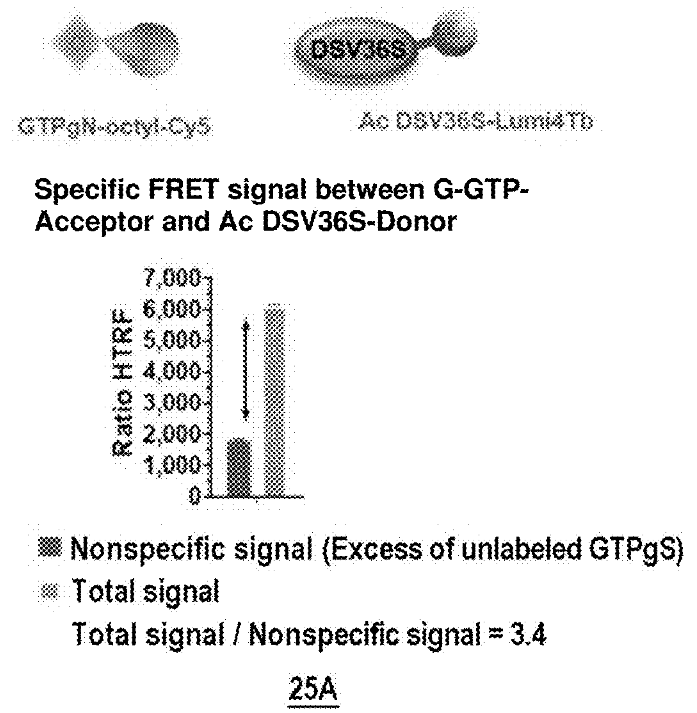
25A
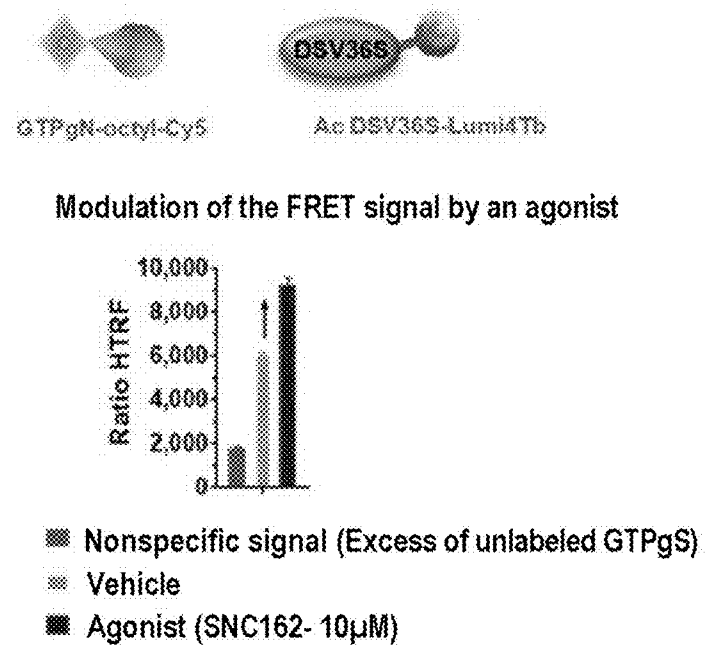
25B

[Fig. 26A-26B]
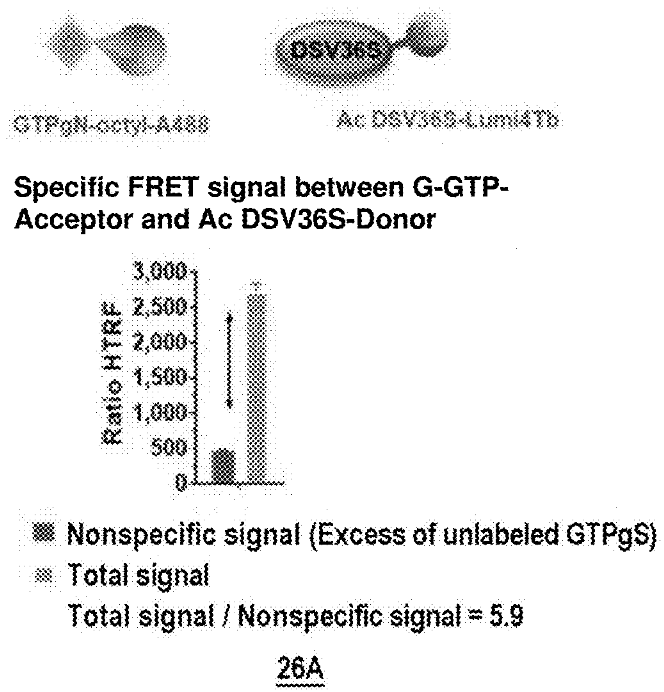
26A
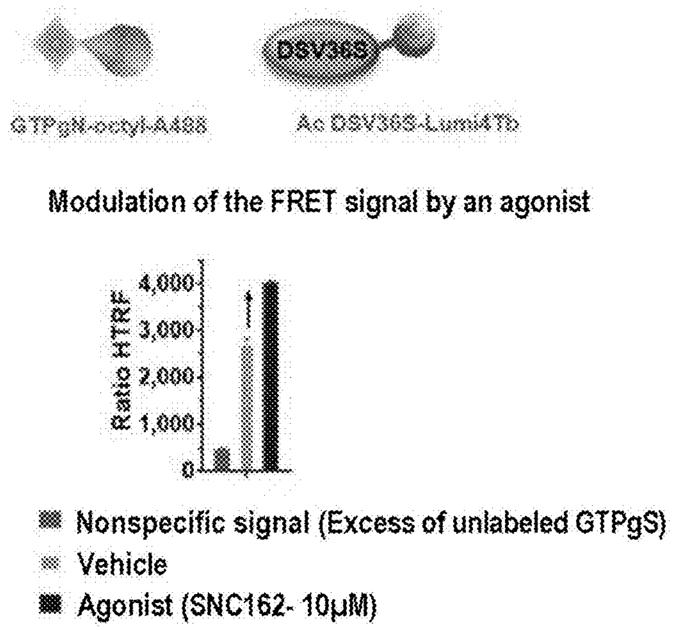
26B

[Fig. 27A-27B]
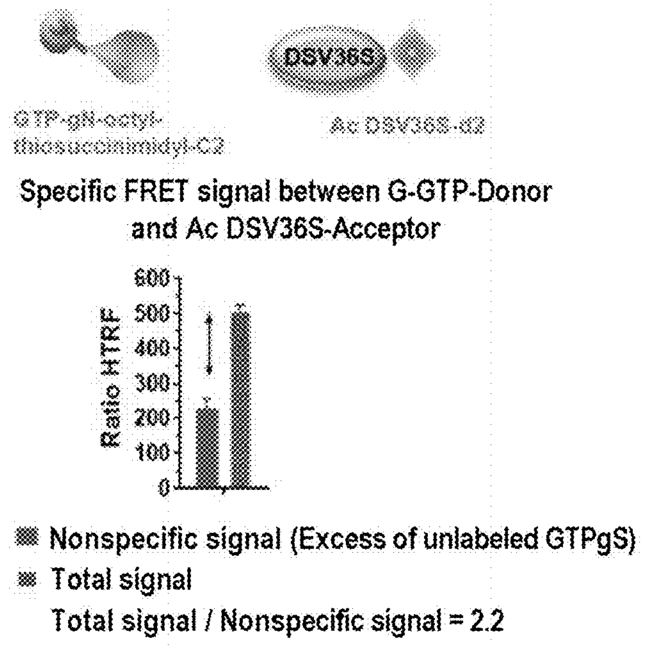
27A
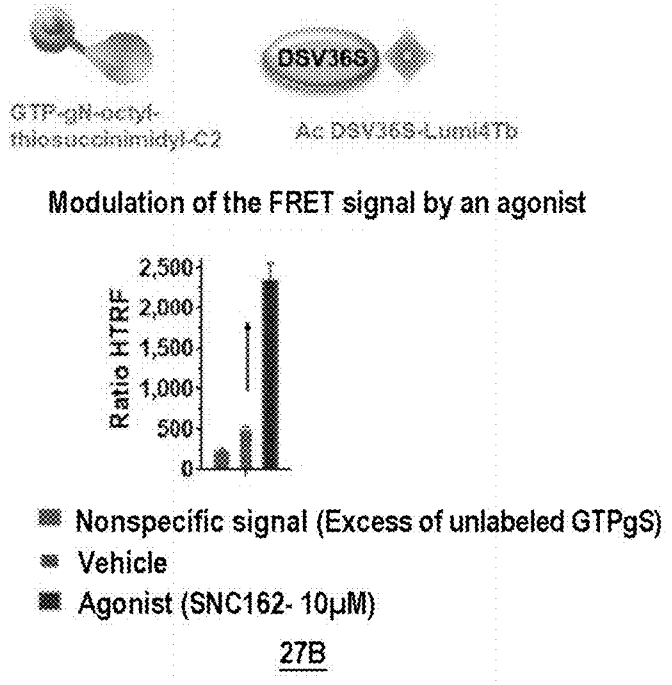
27B

SEQUENCE LISTING

<160> NUMBER OF SEQ ID NOS: 16

<210> SEQ ID NO 1
<211> LENGTH: 19
<212> TYPE: PRT
<213> ORGANISM: Artificial Sequence
<220> FEATURE:
<223> OTHER INFORMATION: Peptide KB1753

<400> SEQUENCE: 1

```
Ser Ser Arg Gly Tyr Tyr His Gly Ile Trp Val Gly Glu Glu Gly Arg
1               5                   10                  15

Leu Ser Arg
```

<210> SEQ ID NO 2
<211> LENGTH: 8
<212> TYPE: PRT
<213> ORGANISM: Artificial Sequence
<220> FEATURE:
<223> OTHER INFORMATION: VH-CDR1

<400> SEQUENCE: 2

```
Gly Phe Asn Ile Lys Asp Tyr Tyr
1               5
```

<210> SEQ ID NO 3
<211> LENGTH: 8
<212> TYPE: PRT
<213> ORGANISM: Artificial Sequence
<220> FEATURE:
<223> OTHER INFORMATION: VH-CDR2

<400> SEQUENCE: 3

```
Ile Asp Pro Glu Asn Gly Asn Thr
1               5
```

<210> SEQ ID NO 4
<211> LENGTH: 14

<212> TYPE: PRT
<213> ORGANISM: Artificial Sequence
<220> FEATURE:
<223> OTHER INFORMATION: VH-CDR3

<400> SEQUENCE: 4

```
Thr Arg Gly Gly Gly Tyr Tyr Ser Asp Trp Tyr Phe Asp Val
1               5                   10
```

<210> SEQ ID NO 5
<211> LENGTH: 5
<212> TYPE: PRT
<213> ORGANISM: Artificial Sequence
<220> FEATURE:
<223> OTHER INFORMATION: VL-CDR1

<400> SEQUENCE: 5

```
Ser Ser Val Ser Tyr
1               5
```

<210> SEQ ID NO 6
<211> LENGTH: 10
<212> TYPE: PRT
<213> ORGANISM: Artificial Sequence
<220> FEATURE:
<223> OTHER INFORMATION: VL-CDR3

<400> SEQUENCE: 6

```
Gln Gln Trp Ser Ser Asn Pro Pro Ile Thr
1               5                   10
```

<210> SEQ ID NO 7
<211> LENGTH: 25
<212> TYPE: PRT
<213> ORGANISM: Artificial Sequence
<220> FEATURE:
<223> OTHER INFORMATION: VH-FR1

<400> SEQUENCE: 7

```
Glu Val Gln Leu Gln Gln Ser Gly Ala Glu Leu Val Arg Pro Gly Ala
1               5                   10                  15

Leu Val Lys Leu Ser Cys Lys Ala Ser
            20                  25
```

<210> SEQ ID NO 8
<211> LENGTH: 17
<212> TYPE: PRT
<213> ORGANISM: Artificial Sequence
<220> FEATURE:
<223> OTHER INFORMATION: VH-FR2

<400> SEQUENCE: 8

```
Met His Trp Val Lys Gln Arg Pro Glu Gln Gly Leu Glu Trp Ile Gly
1               5                   10                  15

Trp
```

<210> SEQ ID NO 9
<211> LENGTH: 38
<212> TYPE: PRT
<213> ORGANISM: Artificial Sequence
<220> FEATURE:
<223> OTHER INFORMATION: VH-FR3

<400> SEQUENCE: 9

```
Ile Tyr Asp Pro Lys Phe Gln Gly Lys Ala Ser Ile Thr Ala Asp Thr
1               5                   10                  15
```

```
Ser Ser Asn Thr Ala Tyr Leu Gln Leu Ser Ser Leu Thr Ser Glu Asp
            20                  25                  30

Thr Ala Val Tyr Tyr Cys
        35


<210> SEQ ID NO 10
<211> LENGTH: 11
<212> TYPE: PRT
<213> ORGANISM: Artificial Sequence
<220> FEATURE:
<223> OTHER INFORMATION: VH-FR4

<400> SEQUENCE: 10

Trp Gly Ala Gly Thr Thr Val Thr Val Ser Ser
1               5                   10


<210> SEQ ID NO 11
<211> LENGTH: 26
<212> TYPE: PRT
<213> ORGANISM: Artificial Sequence
<220> FEATURE:
<223> OTHER INFORMATION: VL-FR1

<400> SEQUENCE: 11

Gln Ile Val Leu Thr Gln Ser Pro Ala Ile Met Ser Ala Ser Pro Gly
1               5                   10                  15

Glu Lys Val Thr Met Thr Cys Ser Ala Ser
            20                  25


<210> SEQ ID NO 12
<211> LENGTH: 17
<212> TYPE: PRT
<213> ORGANISM: Artificial Sequence
<220> FEATURE:
<223> OTHER INFORMATION: VL-FR2

<400> SEQUENCE: 12

Met His Trp Tyr Gln Gln Lys Ser Gly Thr Ser Pro Lys Arg Trp Ile
1               5                   10                  15

Tyr


<210> SEQ ID NO 13
<211> LENGTH: 36
<212> TYPE: PRT
<213> ORGANISM: Artificial Sequence
<220> FEATURE:
<223> OTHER INFORMATION: VL-FR3

<400> SEQUENCE: 13

Lys Leu Ala Ser Gly Val Pro Ala Arg Phe Ser Gly Ser Gly Ser Gly
1               5                   10                  15

Thr Ser Tyr Ser Leu Thr Ile Ser Ser Met Glu Ala Glu Asp Ala Ala
            20                  25                  30

Thr Tyr Tyr Cys
        35


<210> SEQ ID NO 14
<211> LENGTH: 10
<212> TYPE: PRT
<213> ORGANISM: Artificial Sequence
<220> FEATURE:
<223> OTHER INFORMATION: VL-FR4

<400> SEQUENCE: 14
```

```
Phe Gly Ala Gly Thr Lys Leu Glu Leu Lys
1               5                   10


<210> SEQ ID NO 15
<211> LENGTH: 121
<212> TYPE: PRT
<213> ORGANISM: Artificial Sequence
<220> FEATURE:
<223> OTHER INFORMATION: Heavy chain variable domain (VH)

<400> SEQUENCE: 15

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asn Thr Ile Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Arg Gly Gly Gly Tyr Tyr Ser Asp Trp Tyr Phe Asp Val Trp Gly
            100                 105                 110

Ala Gly Thr Thr Val Thr Val Ser Ser
        115                 120


<210> SEQ ID NO 16
<211> LENGTH: 107
<212> TYPE: PRT
<213> ORGANISM: Artificial Sequence
<220> FEATURE:
<223> OTHER INFORMATION: Light chain variable domain (VL)

<400> SEQUENCE: 16

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Ile
                85                  90                  95

Thr Phe Gly Ala Gly Thr Lys Leu Glu Leu Lys
            100                 105
```

METHOD FOR MEASURING THE MODULATION OF THE ACTIVATION OF A G PROTEIN-COUPLED RECEPTOR WITH GTP ANALOGUES

CROSS REFERENCE TO RELATED APPLICATIONS

This application is the National Phase of PCT International Application No. PCT/FR2020/050151, filed on Jan. 30, 2020, which claims priority to French Patent Application No. 1900880, filed on Jan. 30, 2019, the entire disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on 26 Jul. 2021, is named 0177_0184_sequence_listing.txt and is 7 Kilobytes in size.

TECHNICAL FIELD

The invention relates to a new method for measuring the modulation of the activation of a G protein-coupled receptor (GPCR), for example a method for determining the ability of a molecule to modulate the activation of a GPCR. The method according to the invention makes it possible in particular to detect the appearance or disappearance of a full G protein bound to a GTP analogue in a GPCR preparation.

PRIOR ART

The G protein-coupled receptors (GPCR) are a family of membrane receptors in mammals and in the entire animal kingdom. The G-proteins are heterotrimeric proteins (3 subunits: alpha, beta and gamma) that are activated by GPCRs. Via the GPCRs, the G-proteins have a role of transduction of a signal from outside a cell to the interior of the cell (i.e. cellular response to an external stimulus). Their mechanism of action commonly described is presented in FIG. 1 and is summarized hereunder:

- in its inactive state, state of rest, the alpha subunit of the G protein is bound to the nucleotide GDP (full G protein bound to GDP);
- after activation of the GPCR, the latter binds to the alpha subunit of the G protein and triggers a process of activation of the G protein consisting of two steps: 1) departure of GDP from the G protein to give an empty G protein, and formation of an inactive GPCR/empty-G-protein complex, and 2) fixation of GTP, which leads to the formation of an active G protein, in the GTP form (full G protein bound to GTP). In the first step, the G protein bound to the receptor is in a form called "empty form". This state is described in the literature as being transient since it is described that the nucleotide GTP binds quickly to the alpha subunit of the G protein. Moreover, the beta/gamma subunits of the activated G protein dissociate from the alpha subunit;
- the alpha subunit of the full G protein bound to GTP then binds to the effectors, activating them. The effectors in their turn activate signaling pathways, leading to a cellular response;
- the GTP is then hydrolyzed to GDP by the alpha subunit of the G protein and the alpha subunit reassociates with the beta/gamma subunits, reforming the full G protein bound to GDP (inactive state).

There are several subtypes of alpha G-proteins having different selectivity profiles for the different effectors and thus inducing the activation of preferential signaling pathways.

The GPCRs are associated with many important physiological functions and are regarded as one of the preferred therapeutic targets for a large number of pathologies. Thus, a great many in vitro screening assays have been developed for identifying molecules capable of modulating the GPCRs. The assays that have been developed exploit various mechanisms of activation of the G-proteins and employ various technologies (Zhang et al.; Tools for GPCR Drug Discovery; Acta Pharmacologica Sinica, 2012, 33, 372).

We may mention in particular affinity assays that use radiolabeled ligands for measuring the affinity of the ligand for GPCR, scintillation proximity assays that use scintillation beads on which GPCRs have been fixed, or functional assays using weakly or nonhydrolyzable GTP such as GTPγS. However, these assays are difficult to carry out and sometimes require membrane filtration steps which may limit their use as assays for high-throughput screening (HTS).

Other assays have been developed for detecting activation of GPCRs. These assays are based in particular on energy transfer techniques (Resonance Energy Transfer, RET), such as FRET (Fluorescence Resonance Energy Transfer) (Clinical Chemistry, 1995, 41, 1391) or BRET (Bioluminescence Resonance Energy Transfer) (Proceedings of the National Academy of Sciences, 1999, 96(1), 151). These two techniques employ concepts of molecules capable of donating energy (called donors) or of accepting energy (called acceptors) (Physical Chemistry Chemical Physics, 2007, 9, 5847). We may mention for example the energy transfer techniques detecting the interaction between a GPCR and the G protein using either a donor fused to the GPCR and an acceptor fused to the G protein (WO 2006/086883 and WO 2003/008435) or an acceptor fused to the alpha subunit of the G protein and a donor fused to the beta and/or gamma subunit of the G protein (Bunemann et al. Proc. Natl. Acad. Sci., 2003, 26, 16077-16082). These techniques are, however, restrictive since they require preparation of fusion proteins and they do not make it possible to study the GPCRs and the G-proteins expressed endogenously by the cells (i.e. not modified and not over-expressed). Moreover, in order to discriminate the different subtypes of alpha G-proteins that can be activated by the receptor, these techniques require the preparation of multiple membrane samples (a specific preparation for each subtype of alpha G-protein).

Energy transfer techniques have also been used for developing assays that aim to visualize the modulation of the (active) GTP form of the G protein or the (inactive) GDP form of the G protein. We may firstly mention for example the use of a format with the G protein fused to a biotin label thus bound to a donor that is itself coupled to a streptavidin protein and an acceptor bound to a nonhydrolyzable or slowly hydrolyzable GTP analogue (WO 2006/035208). Moreover, another format uses biotinylated BioKey® peptides (KaroBio) discriminating the GTP form from the GDP form and which are bound to a donor by a streptavidin protein coupled to the donor. The acceptor is bound to the GPCR, which is fused with a 6HIS label, using an anti 6HIS antibody (WO 2004/035614). These techniques are also restricting since they too require preparation of fusion proteins and they do not make it possible to study the GPCRs and the G-proteins expressed endogenously by the cells. Similarly, in order to discriminate the different subtypes of alpha G-proteins that can be activated by the receptor, these techniques require preparation of multiple membrane samples.

There is therefore a real need for a sensitive, reliable method allowing easy determination of modulation of the activation of a GPCR, for example for easily determining the ability of a molecule to modulate the activation of a GPCR, and/or for determining what subtype of G protein is activated by the GPCR.

SUMMARY OF THE INVENTION

The present invention aims to propose a new method for in vitro screening of molecules capable of modulating GPCRs. This new method is based in particular on the capacity to discriminate (i) a full form of alpha G-protein bound to a nonhydrolyzable or slowly hydrolyzable GTP labeled with a member of a pair of RET partners and an empty form of G protein or (ii) a full form of alpha G-protein bound to a nonhydrolyzable or slowly hydrolyzable GTP labeled with a member of a pair of RET partners and a full form of alpha G-protein bound to GDP.

In particular, the advantages of the present invention are that 1) it uses a method of detection based on fluorescence, and therefore not radioactive; 2) it does not require a washing step and its application is thus simplified in particular for activities of high-throughput screening of compounds; 3) it makes it possible to work in particular on unmodified G-proteins and GPCRs; 4) it allows discrimination of different subtypes of alpha G-proteins activated by GPCR in one and the same membrane preparation comprising these different subtypes (discrimination being provided by using detection ligands that discriminate the subtypes of alpha G-proteins).

According to a first aspect, the invention relates to a method for determining the ability of a molecule to modulate the activation of a G protein-coupled receptor (GPCR), said method comprising the following steps:

a) introducing, in a first container:
   - a membrane preparation bearing one or more GPCRs and one or more alpha G-proteins,
   - a source of nonhydrolyzable or slowly hydrolyzable GTP labeled with a first member of a pair of RET partners,
   - a ligand of the alpha subunit of a G protein (alpha G-protein) labeled with a second member of the pair of RET partners, said ligand being capable of binding to the full alpha G-protein bound to the nonhydrolyzable or slowly hydrolyzable GTP labeled with the first member of a pair of RET partners,
   - optionally a GPCR agonist;

b) measuring the RET signal emitted in the first container;

c) introducing (i) in a second container, the same reagents as in step a) and the molecule to be assayed or (ii) in the first container, the molecule to be assayed;

d) measuring the RET signal emitted in the second container or in the first container obtained in step c);

e) comparing the signals obtained in steps b) and d), a modulation of the signal obtained in step d) relative to that obtained in step b) indicating that the molecule to be tested is capable of modulating the activation of the GPCR.

BRIEF DESCRIPTION OF THE FIGURES

FIG. 1 shows the mechanism of action of activation of a GPCR and of the G protein.

FIGS. 2A to 2D illustrate 4 assay formats according to the invention.

FIGS. 3A and 3B illustrate an activation test according to format 1A on Delta Opioid GPCR with the detection pair: GTPgN-octyl-C2+DSV36S-d2.

FIGS. 4A and 4B illustrate an activation test according to format 1A on Delta Opioid GPCR with the detection pair: GTPgN-octyl-C11+DSV36S-d2.

FIGS. 5A and 5B illustrate an activation test according to format 1A on Delta Opioid GPCR with the detection pair: GTPgO-hexyl-C2+DSV36S-d2.

FIGS. 6A and 6B illustrate an activation test according to format 1A on Delta Opioid GPCR with the detection pair: GTPgN-C2+DSV36S-d2.

FIGS. 7A and 7B illustrate an activation test according to format 1A on Delta Opioid GPCR with the detection pair: GTPgN-C3+DSV36S-d2.

FIG. 8 illustrates a binding assay on Delta Opioid GPCR with the detection pair: GTPgN-octyl-C3+DSV36S-d2.

FIG. 9 illustrates a binding assay according to format 1A on Delta Opioid GPCR with the detection pair: GTPgO-hexyl-C3+DSV36S-d2.

FIGS. 10A and 10B illustrate the effect of the concentration of membrane and of GTP-donor on an activation test according to format 1A on Delta Opioid GPCR with the detection pair: GTPgN-octyl-C2+DSV36S-d2.

FIGS. 11A and 11B illustrate an activation test according to format 1A on GPCR Dopamine D2 with the detection pair: GTPgN-octyl-C2+DSV36S-d2.

FIGS. 12A and 12B illustrate an activation test according to format 1A on GPCR Dopamine D2 with the detection pair: GTPgN-octyl-C11+DSV36S-d2.

FIGS. 13A and 13B illustrate an activation test according to format 1B on Delta Opioid GPCR with the detection pair: GTPgO-Linker-Cy5(P)+DSV36S-Lumi4Tb.

FIGS. 14A and 14B illustrate an activation test according to format 1B on Delta Opioid GPCR with the detection pair: GTPgS-Linker-Cy5(R)+DSV36S-Lumi4Tb.

FIGS. 15A and 15B illustrate an activation test according to format 1B on Delta Opioid GPCR with the detection pair: GTPgN-L18-Fluorescein+DSV36S-Lumi4Tb.

FIGS. 16A and 16B illustrate an activation test according to format 2A on Delta Opioid GPCR with the detection pair: GTPgN-octyl-C2+DSV36S-d2.

FIGS. 17A and 17B illustrate an activation test according to format 2A on Delta Opioid GPCR with the detection pair: GTPgN-octyl-C2+DSV36S-d2.

FIGS. 18A and 18B illustrate an activation test according to format 2A on Delta Opioid GPCR with the detection pair: GTPgN-octyl-C2+DSV38S-d2.

FIGS. 19A and 19B illustrate an activation test according to format 2A on Delta Opioid GPCR with the detection pair: GTPgN-octyl-C11+DSV36S-d2.

FIGS. 20A and 20B illustrate an activation test according to format 2A on Delta Opioid GPCR with the detection pair: GTPgO-hexyl-C2+DSV36S-d2.

FIGS. 21A and 21B illustrate an activation test according to format 2A on Delta Opioid GPCR with the detection pair: GTPgN-C2+DSV36S-d2.

FIGS. 22A, 22B illustrate an activation test according to format 2A on GPCR Dopamine D2S with the detection pair: GTPgN-octyl-C2+DSV36S-d2.

FIGS. 23A and 23B illustrate an activation test according to format 2A on GPCR Dopamine D2S with the detection pair: GTPgN-octyl-C2+DSV36S-d2.

FIGS. 24A and 24B illustrate an activation test according to format 2A on GPCR Dopamine D2S with the detection pair: GTPgN-octyl-C2+DSV36S-d2.

FIGS. 25A and 25B illustrate an activation test according to format 2B on Delta Opioid GPCR with the detection pair: GTPgN-octyl-Cy5+DSV36S-Lumi4Tb.

FIGS. 26A and 26B illustrate an activation test according to format 2B on Delta Opioid GPCR with the detection pair: GTPgN-octyl-AF488+DSV36S-Lumi4Tb.

FIGS. 27A and 27B illustrate an activation test according to format 2A on Delta Opioid GPCR with the detection pair: GTP-gN-octyl-thiosuccinimidyl-C2+DSV36S-d2.

DETAILED DESCRIPTION

Definitions

In the sense of the invention, the term "G protein" denotes a heterotrimeric protein made up of three subunits called alpha G-protein, beta G-protein and gamma G-protein.

In the sense of the invention, the term "alpha G-protein" or "G-alpha" denotes the alpha subunit of the G protein. The alpha G-protein has two domains, the GTPase domain, and the alpha helix domain. There are at least 20 different alpha G-proteins, which may be classified among the following main families of proteins: G-alphas (known to activate adenylate cyclase in order to increase the synthesis of cAMP), G-alphai (known to inhibit adenylate cyclase), G-alphaolf (associated with the olfactory receptors), G-alphat (known for transduction of the visual signals in the retina in conjunction with the rhodopsin), G-alphaq (known to stimulate phospholipase C) or the family G-alpha12/13 (known to regulate the cytoskeleton, the cellular junctions, and other processes connected with movement of the cell). In a preferred embodiment of the invention, the alpha G-protein is selected from protein G-alphai1, G-alphai2, G-alphai3, G-alphao1, G-alphao2, G-alphaq, G-alpha12, G-alpha13, G-alphas, G-alphaz, G-alphat1, G-alphat2, G-alpha11, G-alpha14, G-alpha15, G-alpha16 and G-alphagus, and is preferably selected from protein G-alphai1, G-alphai2 and G-alphai 3.

In the sense of the invention, the term "full alpha G-protein" denotes an alpha G-protein bound to GTP or to nonhydrolyzable or slowly hydrolyzable GTP (labeled according to the invention or unlabeled) or to GDP. It is then called "full alpha G-protein bound to GTP", "full alpha G-protein bound to nonhydrolyzable or slowly hydrolyzable GTP" or "full alpha G-protein bound to GDP". The full alpha G-protein (bound to GDP or to GTP) is shown in FIG. 1. In the context of the present invention, a nonhydrolyzable or slowly hydrolyzable GTP is used, labeled with a first member of a pair of RET partners that is capable of binding to the alpha G-protein, which makes it possible to obtain a full alpha G-protein bound to the nonhydrolyzable or slowly hydrolyzable GTP labeled with a first member of a pair of RET partners.

The term "GDP" denotes guanosine diphosphate.

The term "GTP" denotes guanosine triphosphate.

The term "nonhydrolyzable or slowly hydrolyzable GTP" denotes a GTP analogue that is not hydrolyzed or is little hydrolyzed to GDP. We may mention for example GTP-gammaS (CAS No. 37589-80-3), GppNHp (CAS No. 148892-91-5) or GppCp (CAS No. 10470-57-2).

The terms "nonhydrolyzable or slowly hydrolyzable GTP labeled with a member of a pair of RET partners" or "nonhydrolyzable or slowly hydrolyzable labeled GTP" or "labeled GTP analogue" denote either a nonhydrolyzable or slowly hydrolyzable donor GTP labeled with a member of a pair of RET partners ("GTP-donor"), or a nonhydrolyzable or slowly hydrolyzable acceptor GTP labeled with a member of a pair of RET partners ("GTP-acceptor").

In the sense of the invention, the term "empty alpha G-protein" denotes an alpha G-protein that is not bound to GTP or to GDP or to nonhydrolyzable or slowly hydrolyzable GTP (modified according to the invention or unmodified), in particular an alpha G-protein that is not bound to nonhydrolyzable or slowly hydrolyzable GTP labeled with a member of a pair of RET partners. The empty alpha G-protein is described in the literature as a transient state between the full form bound to GDP and the full form bound to GTP or to nonhydrolyzable or slowly hydrolyzable GTP. The empty alpha G-protein is shown in FIG. 1.

In the sense of the invention, the term "membrane preparation" denotes a preparation comprising cell membranes or fragments of cell membranes or artificial systems imitating cell membranes which bear (or which express on their surface) one or more GPCRs and one or more alpha G-proteins. Thus, the term "membrane preparation" includes whole cells, permeabilized whole cells, lysed cells, purified cell membranes and GPCR/alpha G-protein complexes purified and reconstituted in nanodisks (also called "nanoscale phospholipid bilayers") or mixtures of detergents which bear (or which express on their surface) one or more GPCRs and one or more alpha G-proteins.

The term "antibody", also called "immunoglobulin", denotes a heterotetramer consisting of two heavy chains of about 50-70 kDa each (called H chains) and two light chains of about 25 kDa each (called L chains), bound to one another by intrachain and interchain disulfide bridges. Each chain consists of, in N-terminal position, a variable region or domain, called VL for the light chain, VH for the heavy chain, and in C-terminal position, a constant region, consisting of a single domain called CL for light chain and three or four domains called CH1, CH2, CH3, CH4, for the heavy chain. Each variable domain generally comprises 4 "hinge regions" (called FR1, FR2, FR3, FR4) and 3 regions directly responsible for binding to the antigen, called "CDR" (called CDR1, CDR2, CDR3).

An "antibody" according to the invention may be of mammalian origin (e.g. human or mouse or camelid family), humanized, chimeric, recombinant. It is preferably a monoclonal antibody produced recombinantly by cells genetically modified according to the techniques familiar to a person skilled in the art. The antibody may be of any isotype, for example IgG, IgM, IgA, IgD or IgE, preferably IgG.

"Chimeric antibody" means an antibody for which the sequences of the variable regions of the light and heavy chains belong to a species different from that of the sequences of constant regions of the light and heavy chains. For the purposes of the invention, the sequences of the variable regions of the heavy and light chains are preferably of murine origin whereas the sequences of the constant regions of the heavy and light chains belong to a nonmurine species. In this respect, for the constant regions, all the species of nonmurine mammals are usable, and in particular human, monkey, suidae, bovines, equines, felines, canines, or birds, this list not being exhaustive. Preferably, the chimeric antibodies according to the invention contain sequences of constant regions of heavy and light chains of human origin and the sequences of variable regions of heavy and light chains of murine origin.

"Humanized antibody" means an antibody for which some or all of the sequences of the regions involved in antigen recognition (the hypervariable regions or CDR:

Complementarity Determining Region) and sometimes certain amino acids of the FR regions (Framework regions) are of nonhuman origin whereas the sequences of the constant regions and of the variable regions not involved in antigen recognition are of human origin.

"Human antibody" means an antibody containing only human sequences, both for the variable and constant regions of the light chains and for the variable and constant regions of the heavy chains.

"Antibody fragment" means any part of an immunoglobulin obtained by enzymatic digestion or obtained by bioproduction comprising at least one disulfide bridge and that is capable of binding to the antigen recognized by the whole antibody, for example Fv, Fab, Fab', Fab'-SH, $F(ab')^2$, diabodies, linear antibodies (also called "Single Domain Antibodies" or sdAb, or nanobodies), antibodies with a single chain (e.g. the scFvs). Enzymatic digestion of the immunoglobulins by pepsin generates a fragment F(ab')2 and a fragment Fc split into several peptides. F(ab')2 is formed from two Fab' fragments bound by interchain disulfide bridges. The Fab parts are made up of the variable regions and the domains CH1 and CL. The Fab' fragment consists of the Fab region and a hinge region. Fab'-SH refers to a Fab' fragment in which the cysteine residue of the hinge region bears a free thiol group.

The term "affinity" refers to the strength of all of the noncovalent interactions between a molecule, for example an antibody or an antibody fragment, and the antigen that is recognized, for example an antigen such as the alpha G-protein. Affinity is generally represented by the dissociation constant (Kd). The dissociation constant (Kd) can be measured by methods that are well known, for example by FRET or SPR.

In the sense of the present invention, "identity" or "homology" is calculated by comparing two sequences aligned in a comparison window. Alignment of the sequences makes it possible to determine the number of positions (nucleotides or amino acids) in common for the two sequences in the comparison window. The number of positions in common is therefore divided by the total number of positions in the comparison window and multiplied by 100 to obtain the percentage identity. Determination of the percentage sequence identity can be carried out manually or using well-known software.

In a particular embodiment of the invention, identity or homology corresponds to at least one substitution, for example 1, 2, 3, 4, 5, 6, 7, 8, 9, 10 substitutions, of an amino acid residue, preferably at least one substitution of an amino acid residue carried out conservatively. "Substitution of an amino acid residue carried out conservatively" consists of replacing an amino acid residue with another amino acid residue, having a side chain possessing similar properties. The families of amino acids possessing side chains with similar properties are well known, we may mention for example basic side chains (e.g. lysine, arginine, histidine), acid side chains (e.g. aspartic acid, glutamic acid), polar and uncharged side chains (e.g. glycine, asparagine, glutamine, serine, threonine, tyrosine, cysteine), nonpolar side chains (e.g. glycine, cysteine, alanine, valine, leucine, isoleucine, proline, phenylalanine, methionine, tryptophan), beta-branched side chains (e.g. threonine, valine, isoleucine) and aromatic side chains (e.g. tyrosine, phenylalanine, tryptophan, histidine).

The homologous antibodies or antibody fragments or "variants of antibodies or of antibody fragments" (i.e. antibodies or antibody fragments having the same function) therefore possess certain amino acids that can be substituted with other amino acids at the level of the constant regions and/or variable regions, without losing the antigen binding capacity. It is preferable for this substitution to be carried out within the DNA sequence that codes for the antibody or antibody fragment, i.e. the substitution is conservative in nature. A person skilled in the art uses his general knowledge to determine the number of substitutions that can be carried out and their localization in order to be able to conserve the function of the antibody or antibody fragment. In order to determine the capacity of one or more variants of antibody or of antibody fragment to bind specifically to an antigen, several suitable methods, familiar to a person skilled in the art and described in the prior art, may be used. The antibodies or the antibody fragments may therefore be assayed by binding methods, for example such as the ELISA method, the method by affinity chromatography, etc. The variants of antibodies or of antibody fragments may be generated for example by the "phage display" method, making it possible to generate a phage library. A large number of methods are known for generating a "phage display" library and for targeting the variants of antibodies or of antibody fragments having the required functional characteristics.

Advantageously, the antibody or the antibody fragment used in the context of the present invention binds to the protein G alphai, G alphao and/or G alphaz, for example it binds to the protein G alphai1, the protein G alphai2 and/or the protein G alphai3. The alphai1 G protein of human origin bears the identifier UniProt P63096-1 for isoform 1 and the identifier UniProt P63096-2 for isoform 2. The gene coding for the alphai1 G protein of human origin is known by the name "GNAI1" (Gene ID: 2770, NCBI).

In the sense of the invention, the term "molecule capable of modulating the activation of the GPCR" denotes a molecule capable of activating or of inhibiting a GPCR, and therefore of inducing transduction or of preventing transduction of a signal from outside a cell to the interior of the cell via the GPCR. It may be an agonist, an antagonist, an inverse agonist, a positive allosteric modulator or a negative allosteric modulator.

In the sense of the invention, the term "molecule to be tested" is a molecule likely to modulate the activation of the GPCR.

In the present description, the term "molecule", not further specified, denotes both the terms "molecule capable of modulating the activation of the GPCR" and "molecule to be tested".

The term "RET" (from the English "Resonance Energy Transfer") denotes the energy transfer techniques.

The term "FRET" (from the English "Fluorescence Resonance Energy Transfer") denotes energy transfer between two fluorescent molecules. FRET is defined as a nonradiative energy transfer resulting from a dipole-dipole interaction between an energy donor and an energy acceptor. This physical phenomenon requires an energy compatibility between these molecules. This signifies that the emission spectrum of the donor must cover, at least partially, the absorption spectrum of the acceptor. In agreement with the Förster theory, FRET is a process that depends on the distance separating the two molecules, donor and acceptor: when these molecules are close to one another, a FRET signal will be emitted.

The term "BRET" ("Bioluminescence Resonance Energy Transfer") denotes energy transfer between a bioluminescent molecule and a fluorescent molecule.

In the sense of the invention, the term "ligand" denotes a molecule capable of binding to a target molecule. In the context of the invention, the target molecule is the full alpha G-protein bound to the nonhydrolyzable or slowly hydrolyzable GTP labeled with a first member of a pair of RET partners. In the context of the present invention, it is necessary for the ligand to be capable of binding to the full alpha G-protein bound to the nonhydrolyzable or slowly hydrolyzable GTP labeled with a first member of a pair of RET partners. However, the ligand is not necessarily specific to the full alpha G-protein bound to the nonhydrolyzable or slowly hydrolyzable GTP labeled with a first member of a pair of RET partners. Thus, the ligand used in the context of the invention may also be capable of binding to the alpha G-protein bound to GDP, to the alpha G-protein bound to GTP, to the alpha G-protein bound to the nonhydrolyzable or slowly hydrolyzable unlabeled GTP, or even to the empty alpha G-protein. The ligand may be of protein nature (e.g. a protein or a peptide) or of nucleotide nature (e.g. DNA or RNA). In the context of the invention, the ligand is advantageously selected from an antibody, an antibody fragment, a peptide or an aptamer, preferably an antibody or an antibody fragment. In the context of the present invention, the ligand may be labeled directly or indirectly by methods familiar to a person skilled in the art, for example as described hereunder, but preferably the ligand is labeled directly, by covalent bonding to a member of a pair of RET partners.

The term "pair of RET partners" denotes a pair consisting of an energy donor compound (hereinafter "donor compound") and of an energy acceptor compound (hereinafter "acceptor compound"); when they are close to one another and when they are excited at the excitation wavelength of the donor compound, these compounds emit a RET signal. It is known that for two compounds to be RET partners, the emission spectrum of the donor compound must partially cover the excitation spectrum of the acceptor compound. For example, we speak of "pairs of FRET partners" when using a fluorescent donor compound and an acceptor compound or "pair of BRET partners" when using a bioluminescent donor compound and an acceptor compound.

The term "RET signal" denotes any measurable signal representative of a RET between a donor compound and an acceptor compound. For example, a FRET signal may therefore be a change in the intensity or the luminescence lifetime of the fluorescent donor compound or of the acceptor compound when the latter is fluorescent.

The term "container" denotes a well of a plate, a test tube or any other container suitable for mixing a membrane preparation with the reagents necessary for carrying out the method according to the invention.

The invention relates to a method for determining the ability of a molecule to modulate the activation of a G protein-coupled receptor (GPCR), said method comprising the following steps:

a) introducing, in a first container:
  - a membrane preparation bearing one or more GPCRs and one or more alpha G-proteins,
  - a source of nonhydrolyzable or slowly hydrolyzable GTP labeled with a first member of a pair of RET partners,
  - a ligand of the alpha subunit of a G protein (alpha G-protein) labeled with a second member of the pair of RET partners, said ligand being capable of binding to the full alpha G-protein bound to the nonhydrolyzable or slowly hydrolyzable GTP labeled with the first member of a pair of RET partners,
  - optionally a GPCR agonist;

b) measuring the RET signal emitted in the first container;

c) introducing (i) in a second container, the same reagents as in step a) and the molecule to be assayed or (ii) in the first container, the molecule to be assayed;

d) measuring the RET signal emitted in the second container or in the first container obtained in step c);

e) comparing the signals obtained in steps b) and d), a modulation of the signal obtained in step d) relative to that obtained in step b) indicating that the molecule to be tested is capable of modulating the activation of the GPCR.

It is not necessary to add a source of GTP, other than the nonhydrolyzable or slowly hydrolyzable labeled GTP, when carrying out the method according to the invention. Moreover, advantageously, no other source of GTP than the nonhydrolyzable or slowly hydrolyzable labeled GTP is added when carrying out the method according to the invention.

It is also unnecessary to add a source of GDP when carrying out the method according to the invention. However, a small amount of GDP may be tolerated when carrying out the method according to the invention, for example in step a). In formats 1A and 1B (FIGS. 2A and 2B), advantageously, no source of GDP is added when carrying out the method according to the invention. In formats 2A and 2B (FIGS. 2C and 2D), addition of GDP may allow better discrimination of the signal between a condition not containing an agonist and a condition containing an agonist.

Step a)

Step a) consists of introducing, in a first container, the following three or four elements:
- a membrane preparation bearing one or more GPCRs and one or more alpha G-proteins,
- a source of nonhydrolyzable or slowly hydrolyzable GTP labeled with a first member of a pair of RET partners,
- a ligand of the alpha subunit of a G protein (alpha G-protein) labeled with a second member of the pair of RET partners, said ligand being capable of binding to the full alpha G-protein bound to the nonhydrolyzable or slowly hydrolyzable GTP labeled with the first member of a pair of RET partners, and
- optionally a GPCR agonist.

Advantageously, the nonhydrolyzable or slowly hydrolyzable GTP is selected from GTPgammaS (GTPγS or GTPgS), GppNHp and GppCp. The GTPgammaS has to be labeled at a position other than the third phosphate (gamma phosphate). The three or four elements may be introduced into the container sequentially in any order, or simultaneously or quasi-simultaneously. Mixing the 3 elements makes it possible to obtain a reaction solution suitable for carrying out a RET. Other elements may be added to the container in order to adapt the solution for carrying out the RET. For example, coelenterazine h (benzyl-coelenterazine) or bisdeoxycoelenterazine (DeepBlueC™) or didehydrocoelenterazine (coelenterazine-400a) or D-luciferin may be added.

In a first particular embodiment, the ligand of the alpha G-protein binds specifically to the SwitchII domain of the alpha G-protein, in particular to the peptide 215-294 of the alpha G-protein. For example, the alpha G-protein is selected from G-alphai1, G-alphai2 and G-alphai3 and the ligand of the alpha G-protein is a peptide KB1753 of sequence Ser-Ser-Arg-Gly-Tyr-Tyr-His-Gly-Ile-Trp-Val-Gly-Glu-Glu-Gly-Arg-Leu-Ser-Arg (SEQ ID No: 1).

In a second particular embodiment, the alpha G-protein is selected from G-alphai1, G-alphai2 and G-alphai3 and the ligand of the alpha G-protein competes to bind to said alpha G-protein with the peptide KB1753 (SEQ ID No: 1). The capacity of the ligand for competing to bind to said alpha G-protein with the peptide KB1753 (SEQ ID No: 1) can be tested by a competitive method.

A "competitive method" consists of testing a ligand of the alpha G-protein for its ability to block the binding between the peptide KB1753 (SEQ ID No: 1) and the alpha G-protein, or to compete with the peptide KB1753 (SEQ ID No: 1) to bind to the alpha G-protein. In other words, a ligand of the alpha G-protein that competes with the peptide KB1753 (SEQ ID No: 1) to bind to the alpha G-protein binds to the same epitope as the peptide KB1753 (SEQ ID No: 1) or to an epitope that is close enough to the epitope recognized by the peptide KB1753 (SEQ ID No: 1) to prevent binding of the ligand of the alpha G-protein for reasons of steric hindrance. Many types of competitive methods may be used for determining whether a ligand of the alpha G-protein competes with the peptide KB1753 (SEQ ID No: 1), for example by ELISA assay. For example, the ELISA competitive method involves the use of a purified alpha G-protein bound to a solid surface or to cells, a ligand of the alpha G-protein to be assayed that binds to the alpha G-protein and the labeled peptide KB1753. Usually, the reference peptide KB1753 (SEQ ID No: 1) is used at a nonsaturating concentration (relative to its dissociation constant Kd for the alpha G-protein) and the signal is measured in the absence or in the presence of increasing concentrations of the ligand of the alpha G-protein to be assayed. When a ligand of the alpha G-protein of interest is present in excess, it may block specific binding of the peptide KB1753 (SEQ ID No: 1) to the alpha G-protein by at least 40-45%, 45-50%, 50-55%, 55-60%, 60-65%, 65-70%, 70-75% or 75% or more. In certain cases, binding is blocked by at least 80 to 85%, 85 to 90%, 90 to 95%, 95 to 97% or 97% or more.

Another example of a competitive method may use TR-FRET. For example, TR-FRET involves the use of a purified and tagged alpha G-protein, an anti-Tag ligand (advantageously an antibody) labeled with the first member of the pair of TR-FRET partners (advantageously the donor) capable of binding, on the tag of the alpha G-protein, the peptide KB1753 (SEQ ID NO: 1) labeled with the second member of the pair of TR-FRET partners (advantageously the acceptor by a method of indirect labeling with a biotin on the peptide and the streptavidin-acceptor) and a ligand of the alpha G-protein to be assayed. Usually, the peptide KB1753 (SEQ ID NO: 1) is used at a nonsaturating concentration (relative to its dissociation constant Kd for the alpha G-protein) and the TR-FRET signal is measured in the absence or in the presence of increasing concentrations of the ligand of the alpha G-protein to be assayed. When a ligand of the alpha G-protein of interest is assayed, it may block the specific bond of the peptide KB1753 (SEQ ID No: 1) to the alpha G-protein by at least 40-45%, 45-50%, 50-55%, 55-60%, 60-65%, 65-70%, 70-75% or 75% or more. In certain cases, binding is blocked by at least 80 to 85%, 85 to 90%, 90 to 95%, 95 to 97% or 97% or more. If the ligand of the alpha G-protein tested inhibits the binding of the peptide KB1753 (SEQ ID No: 1), the orthosteric character of the inhibition (as opposed to allosteric inhibition) may be confirmed by Schild-Plot experiments, which consist of measuring the dissociation constant (Kd) of the labeled peptide KB1753 (SEQ ID No: 1) for the alpha G-protein in the absence or in the presence of increasing concentrations of the ligand of the alpha G-protein. If Kd varies in a linear and nonsaturable manner when the concentration of ligand of the alpha G-protein increases, inhibition is orthosteric (i.e. the peptide KB1753 (SEQ ID No: 1) and the ligand of the alpha G-protein binds on the same epitope of the alpha G-protein). If Kd varies in a nonlinear and saturable manner when the concentration of ligand of the alpha G-protein increases, inhibition is allosteric (i.e. the peptide KB1753 (SEQ ID No: 1) and the ligand does not bind on the same epitope of the alpha G-protein).

The ligand of the alpha G-protein may be an antibody or an antibody fragment.

Thus, in a third particular embodiment, the ligand of the alpha G-protein is an antibody or an antibody fragment capable of binding to the alpha G-protein, which comprises:

- a variable domain of a heavy chain comprising a CDR1 of amino acid sequence SEQ ID NO: 2, a CDR2 of amino acid sequence SEQ ID NO: 3, and a CDR3 of amino acid sequence SEQ ID NO: 4, and
- a variable domain of a light chain comprising a CDR1 of amino acid sequence SEQ ID NO: 5, a CDR2 of amino acid sequence DTS (i.e. the three amino acids "Asp Thr Ser", i.e. the three amino acids aspartic acid, threonine, serine), and a CDR3 of amino acid sequence SEQ ID NO: 6.

The variable domain of the heavy chain of the antibody or antibody fragment capable of binding to the alpha G-protein may comprise:

- an FR1 having at least 80% homology, preferably at least 90% homology, for example at least 95% homology, at least 96%, at least 97%, at least 98%, at least 99% or even 100% homology with the amino acid sequence SEQ ID NO: 7,
- an FR2 having at least 80% homology, preferably at least 90% homology, for example at least 95% homology, at least 96%, at least 97%, at least 98%, at least 99% or even 100% homology with the amino acid sequence SEQ ID NO: 8,
- an FR3 having at least 80% homology, preferably at least 90% homology, for example at least 95% homology, at least 96%, at least 97%, at least 98%, at least 99% or even 100% homology with the amino acid sequence SEQ ID NO: 9, and/or
- an FR4 having at least 80% homology, preferably at least 90% homology, for example at least 95% homology, at least 96%, at least 97%, at least 98%, at least 99% or even 100% homology with the amino acid sequence SEQ ID NO: 10.

The variable domain of the light chain of the antibody or antibody fragment capable of binding to the alpha G-protein may comprise:

- an FR1 having at least 80% homology, preferably at least 90% homology, for example at least 95% homology, at least 96%, at least 97%, at least 98%, at least 99% or even 100% homology with the amino acid sequence SEQ ID NO: 11,
- an FR2 having at least 80% homology, preferably at least 90% homology, for example at least 95% homology, at least 96%, at least 97%, at least 98%, at least 99% or even 100% homology with the amino acid sequence SEQ ID NO: 12,
- an FR3 having at least 80% homology, preferably at least 90% homology, for example at least 95% homology, at least 96%, at least 97%, at least 98%, at least 99% or even 100% homology with the amino acid sequence SEQ ID NO: 13, and/or
- an FR4 having at least 80% homology, preferably at least 90% homology, for example at least 95% homology, at least 96%, at least 97%, at least 98%, at least 99% or even 100% homology with the amino acid sequence SEQ ID NO: 14.

In a particular embodiment of the antibody or antibody fragment capable of binding to the alpha G-protein:

the variable domain of the heavy chain comprises:
- an FR1 of amino acid sequence SEQ ID NO: 7 (i.e. 100% homology with the amino acid sequence SEQ ID NO: 7),
- an FR2 of amino acid sequence SEQ ID NO: 8,
- an FR3 of amino acid sequence SEQ ID NO: 9, and
- an FR4 of amino acid sequence SEQ ID NO: 10; and the variable domain of the light chain comprises:
- an FR1 of amino acid sequence SEQ ID NO: 11,
- an FR2 of amino acid sequence SEQ ID NO: 12,
- an FR3 of amino acid sequence SEQ ID NO: 13, and
- an FR4 of amino acid sequence SEQ ID NO: 14.

In a particular embodiment of the antibody or antibody fragment capable of binding to the alpha G-protein, the variable domain of the heavy chain may have at least 80% homology, preferably at least 90% homology, for example at least 95% homology, at least 96%, at least 97%, at least 98%, at least 99% or 100% homology with the amino acid sequence SEQ ID NO: 15, and the variable domain of the light chain may have at least 80% homology, preferably at least 90% homology, for example at least 95% homology, at least 96%, at least 97%, at least 98%, at least 99% or 100% homology with the amino acid sequence SEQ ID NO: 16.

Thus, the ligand of the alpha G-protein may be an antibody or antibody fragment in which:
- the variable domain of the heavy chain has at least 80% homology, preferably at least 90% homology, for example at least 95% homology, at least 96%, at least 97%, at least 98%, at least 99% or 100% homology with the amino acid sequence SEQ ID NO: 15;
- the variable domain of the light chain has at least 80% homology, preferably at least 90% homology, for example at least 95% homology, at least 96%, at least 97%, at least 98%, at least 99% or 100% homology with the amino acid sequence SEQ ID NO: 16; and
- CDR1 of the variable domain of the heavy chain consists of amino acid sequence SEQ ID NO: 2, CDR2 of the variable domain of the heavy chain consists of amino acid sequence SEQ ID NO: 3, CDR3 of the variable domain of the heavy chain consists of amino acid sequence SEQ ID NO: 4, CDR1 of the variable domain of the light chain consists of amino acid sequence SEQ ID NO: 5, CDR2 of the variable domain of the light chain consists of amino acid sequence DTS, and CDR3 of the variable domain of the light chain consists of amino acid sequence SEQ ID NO: 6.

Advantageously, the ligand of the alpha G-protein is an antibody an antibody or antibody fragment in which the variable domain of the heavy chain consists of amino acid sequence SEQ ID NO: 15 (i.e. the variable domain of the heavy chain has 100% homology with the amino acid sequence SEQ ID NO: 15) and the variable domain of the light chain consists of amino acid sequence SEQ ID NO: 16.

The antibody described in the examples under the reference DSV36S (DVS antibody available from Cisbio Bioassays on request) comprises a variable domain of the heavy chain that consists of amino acid sequence SEQ ID NO: 15 and a variable domain of the light chain that consists of amino acid sequence SEQ ID NO: 16.

The antibody or antibody fragment capable of binding to the alpha G-protein according to the third particular embodiment described above is called "reference antibody or antibody fragment" hereunder in the fourth particular embodiment.

In a fourth particular embodiment, the ligand of the alpha G-protein is an antibody or an antibody fragment that competes to bind to the alpha G-protein with the reference antibody or antibody fragment, "competing antibody or antibody fragment" hereunder.

The ability of an antibody or an antibody fragment to compete with the reference antibody or antibody fragment to bind to the alpha G-protein may be tested by a competitive method. A "competitive method" consists of testing an antibody (or an antibody fragment) for its ability to block the binding between a reference antibody or antibody fragment and an antigen or to compete with a reference antibody or antibody fragment for binding to the antigen. In other words, an antibody that competes with the reference antibody or antibody fragment binds to the same epitope as the reference antibody or antibody fragment or to an epitope that is close enough to the epitope recognized by the reference antibody or antibody fragment to prevent binding of the reference antibody or antibody fragment for reasons of steric hindrance.

A great many types of competitive methods may be used for determining whether an antibody or an antibody fragment completes with a reference antibody or antibody fragment, for example: by competitive ELISA assay, by the direct or indirect sandwich method, by direct or indirect solid-phase radioimmunoassay (RIA), by direct or indirect solid-phase enzymatic immunoassay (EIA), etc. For example, the competitive ELISA method involves the use of a purified antigen bound to a solid surface or to cells, the antibody to be tested, which binds to the unlabeled antigen and a reference labeled antibody or antibody fragment. Usually, the reference antibody or antibody fragment is present in nonsaturating concentration (relative to its dissociation constant Kd for the alpha G-protein) and the signal is measured at increasing concentrations of the antibody or antibody fragment being tested. When an antibody is present in excess, it may block or inhibit (for example reduce) the specific binding of a reference antibody or antibody fragment to an antigen by at least 40-45%, 45-50%, 50-55%, 55-60%, 60-65%, 65-70%, 70-75% or 75% or more. In certain cases, binding is inhibited by at least 80 to 85%, 85 to 90%, 90 to 95%, 95 to 97% or 97% or more.

The competing antibodies or antibody fragments used in the method according to the invention may, for example, be obtained with the reference antibody or antibody fragment by carrying out the protocol described in Example 26. The antibody described in the examples under the reference DSV38S (DVS antibody available from Cisbio Bioassays on request) is a competing antibody that may be used in the method according to the invention.

The reference antibodies or antibody fragments and the competing antibodies or antibody fragments as defined above are called jointly "antibody or antibody fragments used in the method according to the invention" hereinafter.

The antibody or antibody fragment used in the method according to the invention may bind to the alpha G-protein in an isolated form and/or present in a membrane environment, for example it may bind to an alpha G-protein present in a preparation from membranes bearing one or more GPCRs and one or more alpha G-proteins. It is not necessary for the alpha G-protein to be complexed with the GPCR for the antibody according to the invention to be able to bind to the alpha G-protein.

The antibody or antibody fragment used in the method according to the invention may bind to the alpha G-protein with a dissociation constant (Kd) measured in FRET less than or equal to 20 nM. A dissociation constant below 20 nM is preferable for proper execution of a RET. Advantageously, the antibody or antibody fragment used in the method according to the invention may bind to the alpha G-protein with a dissociation constant (Kd) measured in FRET less than or equal to 20 nM, for example an affinity constant less than or equal to 10 nM or else less than or equal to 5 nM, for example from 0 to 20 nM (0 being excluded), from 0 to 10 nM (0 being excluded), from 0 to 5 nM (0 being excluded). A method for measuring Kd of an antibody or an antibody fragment according to the invention in FRET is described in Example 27.

The antibody or antibody fragment used in the method according to the invention is particularly advantageous in carrying out the method according to the invention.

For example, antibodies or antibody fragments used in the method according to the invention may be obtained by carrying out the protocol described in Example 26.

The inventors have also shown that the antibodies or antibody fragments used in the method according to the invention bind to the SwitchII domain of the alpha G-protein, and more particularly to the peptide 215-294 of the alpha G-protein.

The first container may optionally contain a GPCR agonist. GPCR agonists are described widely in the literature, for example in Table 1 of application WO2011/018586.

Step b)

Step b) consists of measuring the RET signal emitted in the first container, i.e. the container obtained in step a). The measured signal corresponds to the signal obtained in the container in the absence of the molecule to be assayed. Measurement may be done by conventional methods familiar to a person skilled in the art and do not pose any particular problem. Generally an apparatus is used that makes it possible to detect and measure the RET signal, for example such as the PHERAstar FS microplate reader (BMG Labtech) in the TR-FRET or bioluminescence reading mode.

Step c)

In one embodiment, step c) consists of introducing, into a second container, the same reagents as in step a) and the molecule to be assayed. Advantageously, the second container is prepared in the same way as the first container, the only difference being the presence of the molecule to be assayed in the second container. This embodiment is advantageous as it makes it possible to measure the RET signal emitted in the first container and in the second container simultaneously. This embodiment also makes it possible to perform simultaneous measurement of the RET signal emitted in one or more second containers. Thus, this embodiment is particularly advantageous since it makes it possible to test several different molecules in parallel.

In another embodiment, step c) consists of putting the molecule to be assayed in the first container. This embodiment has the advantage of only using one container for carrying out the method according to the invention.

Step d)

Step d) consists of measuring the RET signal emitted in the second container or in the first container obtained in step c). The measured signal corresponds to the signal obtained in the container in the presence of the molecule to be assayed. As in step b), measurement may be done by conventional methods familiar to a person skilled in the art and do not pose any particular problem. Generally an apparatus is used that makes it possible to detect and measure the RET signal, for example such as the PHERAstar FS microplate reader (BMG Labtech) in the TR-FRET or bioluminescence reading mode.

Step e)

Step e) consists of comparing the signals obtained in steps b) and d), a modulation of the signal obtained in step d) relative to that obtained in step b) indicating that the molecule to be tested is capable of modulating the activation of the GPCR. The modulation of the signal may be either an increase in the signal or a decrease in the signal.

A person skilled in the art can easily compare the signals in steps b) and d) and define a threshold allowing him to qualify the modulation, for example a difference between the signals greater than 5%, greater than 10%, greater than 15%, greater than 20% or greater than 25%. For example, the ratio between the signals in steps b) and d) may be calculated. In general, for a given pair of RET partners, the greater the difference between the signals, the greater will be the ratio between the signals, and the modulation of the activation of the GPCR (e.g. activation or inhibition) will be greater. The difference between the signals is, however, liable to vary as a function of the pair of RET partners used for carrying out the method according to the invention. The level of modulation of the activation of the GPCR makes it possible to identify molecules that are more or less agonists, antagonists, positive allosteric modulating or negative allosteric modulating inverse agonists.

In a first particular embodiment, the first container does not contain a GPCR agonist and in step e) a decrease in the signal obtained in step d) relative to that obtained in step b) indicates that the molecule to be tested is a GPCR agonist.

In a second particular embodiment, the first container comprises a GPCR agonist and in step e):

- an increase in the signal obtained in step d) relative to that obtained in step b) indicating that the molecule to be tested is an antagonist or a negative allosteric modulator of the GPCR;
- a decrease in the signal obtained in step d) relative to that obtained in step b) indicating that the molecule to be tested is an agonist or a positive allosteric modulator of the GPCR.

In a third particular embodiment, the first container does not comprise a GPCR agonist and in step e) an increase in the signal obtained in step d) relative to that obtained in step b) indicates that the molecule to be tested is a GPCR agonist.

In a fourth particular embodiment, the first container comprises a GPCR agonist and in step e):

- a decrease in the signal obtained in step d) relative to that obtained in step b) indicating that the molecule to be tested is an antagonist or a negative allosteric modulator of the GPCR;
- an increase in the signal obtained in step d) relative to that obtained in step b) indicating that the molecule to be tested is an agonist or a positive allosteric modulator of the GPCR.

Labeling of the Ligand with a Member of a Pair of RET Partners

The ligand may be labeled directly or indirectly.

Direct labeling of the ligand with a member of a pair of RET partners, for example a fluorescent compound when carrying out a FRET, may be carried out by the conventional methods known by a person skilled in the art, based on the presence of reactive groups on the ligand. For example, when the ligand is an antibody or an antibody fragment, the following reactive groups may be used: terminal amino group, carboxylate groups of aspartic and glutamic acids, the amine groups of lysines, the guanidine groups of arginines, the thiol groups of cysteines, the phenol groups of tyrosines, the indole rings of tryptophans, the thioether groups of methionines, the imidazole groups of histidines.

The reactive groups may form a covalent bond with a reactive group borne by the ligand. The suitable reactive groups, borne by the ligand, are familiar to a person skilled in the art, for example a donor compound or an acceptor compound functionalized with a maleimide group will be for example capable of bonding covalently to the thiol groups borne by the cysteines borne by a protein or a peptide, for example an antibody or an antibody fragment. Similarly, a donor/acceptor compound bearing an N-hydroxysuccinimide ester will be capable of binding covalently to an amine present in a protein or a peptide.

The ligand may also be labeled with a fluorescent or bioluminescent compound indirectly, for example by introducing, into the measurement medium, an antibody or an antibody fragment that is itself bound covalently to an acceptor/donor compound, this second antibody or antibody fragment recognizing the ligand specifically.

Another very conventional means of indirect labeling consists of fixing biotin on the ligand to be labeled, and then incubating this biotinylated ligand in the presence of streptavidin labeled with an acceptor/donor compound. Suitable biotinylated ligands may be prepared by techniques familiar to a person skilled in the art; the company Cisbio Bioassays markets for example streptavidin labeled with a fluorophor with the trade name "d2" (ref. 610SADLA).

In the context of the invention, the ligand is labeled with (i) a fluorescent donor compound or luminescent donor compound, or (ii) a fluorescent acceptor compound or a nonfluorescent acceptor compound (quencher). Preferably, the ligand is labeled with a fluorescent acceptor compound or a nonfluorescent acceptor compound (quencher).

Labeling of the Nonhydrolyzable or Slowly Hydrolyzable GTP with a Member of a Pair of RET Partners The nonhydrolyzable or slowly hydrolyzable GTP may be labeled directly or indirectly. Preferably, the nonhydrolyzable or slowly hydrolyzable GTP is labeled directly.

Direct labeling of the nonhydrolyzable or slowly hydrolyzable GTP with a member of a pair of RET partners, for example a fluorescent compound when carrying out a FRET, may be carried out by the methods based on the presence of reactive groups on the nonhydrolyzable or slowly hydrolyzable GTP.

The reactive groups may form a covalent bond with a reactive group borne by a member of a pair of RET partners. The suitable reactive groups, borne by the member of a pair of RET partners, are familiar to a person skilled in the art, for example a donor compound or an acceptor compound functionalized with a maleimide group will be for example capable of bonding covalently to the thiol groups. Similarly, a donor/acceptor compound bearing an N-hydroxysuccinimide ester will be capable of bonding covalently to an amine.

In the context of the invention, the nonhydrolyzable or slowly hydrolyzable GTP is labeled with (i) a fluorescent donor compound, or (ii) a fluorescent acceptor compound or a nonfluorescent acceptor compound (quencher). Preferably, the nonhydrolyzable or slowly hydrolyzable GTP is labeled with a fluorescent donor compound.

In a particular embodiment, the nonhydrolyzable or slowly hydrolyzable GTP is labeled with a fluorescent donor compound and the ligand of the alpha G-protein is labeled with a fluorescent acceptor compound or a nonfluorescent acceptor compound (quencher). In another particular embodiment, the nonhydrolyzable or slowly hydrolyzable GTP is labeled with a fluorescent acceptor compound or a nonfluorescent acceptor compound (quencher) and the ligand of the alpha G-protein is labeled with a fluorescent donor compound or luminescent donor compound.

Labeling for Carrying Out a FRET

In a particular embodiment, the ligand and the nonhydrolyzable or slowly hydrolyzable GTP are each labeled with a member of a pair of FRET partners, i.e. a fluorescent energy-donating compound or a fluorescent energy-accepting compound.

Selection of the pair of FRET partners for obtaining a FRET signal is within the capability of a person skilled in the art. For example, donor-acceptor pairs usable for studying the FRET phenomena are in particular described in the work by Joseph R. Lakowicz (Principles of fluorescence spectroscopy, $2^{nd}$ edition 338), to which a person skilled in the art may refer.

Fluorescent Donor Compounds

The fluorescent energy-donating compounds that are long-lived (>0.1 ms, preferably in the range from 0.5 to 6 ms), in particular the lanthanide complexes i.e. the chelates, macrocycles or cryptates of rare earths are advantageous since they make it possible to perform time-resolved measurements, i.e. to measure TR-FRET (Time-Resolved FRET) signals, eliminating a large part of the background noise emitted by the measurement medium. For this reason and in general they are preferred for carrying out the method according to the invention. Advantageously, these compounds are lanthanide complexes. These complexes (such as chelates or cryptates) are particularly suitable as a member of the energy-donating FRET pair.

The complexes of europium (Eu3+), of terbium (Tb3+), of dysprosium (Dy3+), of samarium (Sm3+), of neodymium (Nd3+), of ytterbium (Yb3+) or of erbium (Er3+) are rare earth complexes that are also suitable for the purposes of the invention, the complexes of europium (Eu3+) and of terbium (Tb3+) being particularly preferred.

Numerous rare earth complexes have been described and several are currently marketed by the companies Perkin Elmer, Invitrogen and Cisbio Bioassays.

Examples of chelates or cryptates of rare earths suitable for the purposes of the invention are:

The cryptates of lanthanides, comprising one or more pyridine units. Such cryptates of rare earths are described for example in patents EP 0 180 492, EP 0 321 353, EP 0 601 113 and in international application WO 01/96 877. The cryptates of terbium (Tb3+) and of europium (Eu3+) are particularly suitable for the purposes of the present invention. Cryptates of lanthanides are marketed by the company Cisbio Bioassays. We may mention, as nonlimiting examples, the cryptates of europium with the following formulas (which may be coupled to the compound to be labeled via a reactive group, here for example an $NH_2$ group):

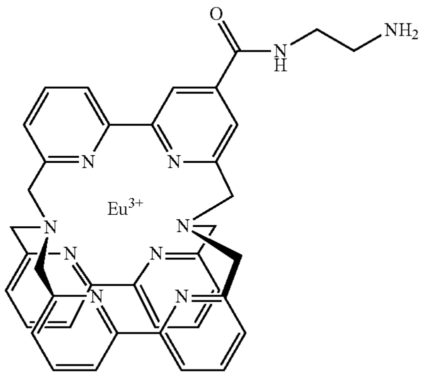

TrisBiPy-Eu

-continued

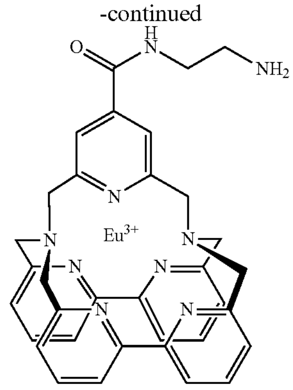

Py-BiPy-Eu

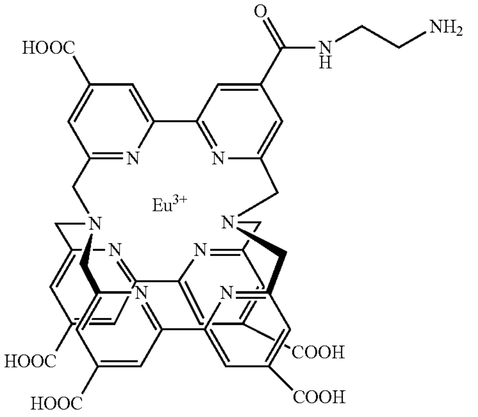

TrisBiPy-tetraacide-Eu

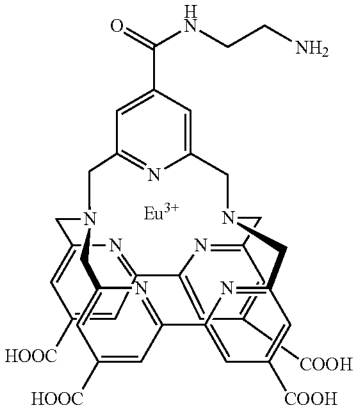

Py-BiPy-tetraacide-Eu

The chelates of lanthanides described in particular in U.S. Pat. Nos. 4,761,481, 5,032,677, 5,055,578, 5,106,957, 5,116,989, 4,761,481, 4,801,722, 4,794,191, 4,637, 988, 4,670,572, 4,837,169, 4,859,777. The patents EP 0 403 593, U.S. Pat. Nos. 5,324,825, 5,202,423, 5,316, 909 describe chelates consisting of a nonadentate ligand such as terpyridine. Chelates of lanthanides are marketed by the company Perkin Elmer.

Lanthanide complexes consisting of a chelating agent, such as tetraazacyclododecane, substituted with a chromophore comprising aromatic rings, such as those described by Poole R. et al. in Biomol. Chem, 2005, 3, 1013-1024 "Synthesis and characterisation of highly emissive and kinetically stable lanthanide complexes suitable for usage in cellulo", may also be used. The complexes described in application WO 2009/10580 may also be used.

The lanthanide cryptates described in patents EP 1 154 991 and EP 1 154 990 are also usable.

The terbium cryptate of the following formula (which may be coupled to a compound to be labeled via a reactive group, here for example an $NH_2$ group):

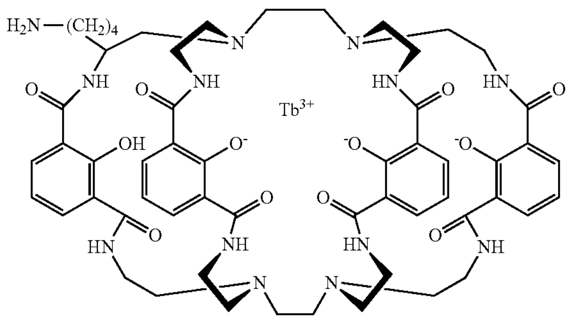

and the synthesis of which is described in international application WO 2008/063721 (compound 6a, page 89).

The terbium cryptate Lumi4-Tb from the company Lumiphore, marketed by Cisbio Bioassays.

The quantum dye from the company Research Organics, of the following formula (which may be coupled to the compound to be labeled via a reactive group, here NCS):

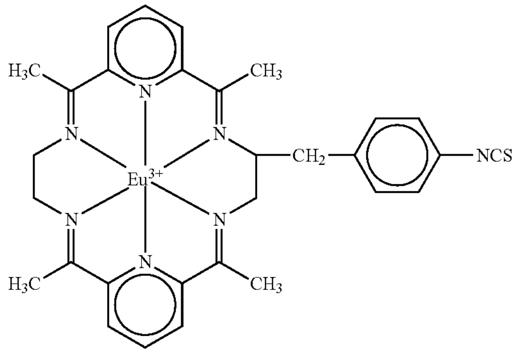

The ruthenium chelates, in particular the complexes consisting of a ruthenium ion and several bipyridines such as ruthenium(II) tris(2,2'-bipyridine).

The terbium chelate DTPA-cs124 Tb, marketed by the company Life Technologies of the following formula (which may be coupled to the compound to be labeled via a reactive group R) and whose synthesis is described in the American patent U.S. Pat. No. 5,622, 821.

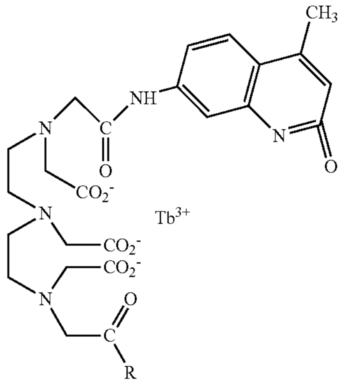

The terbium chelate of the following formula, and described by Latva et al. (Journal of Luminescence 1997, 75(2): 149-169):

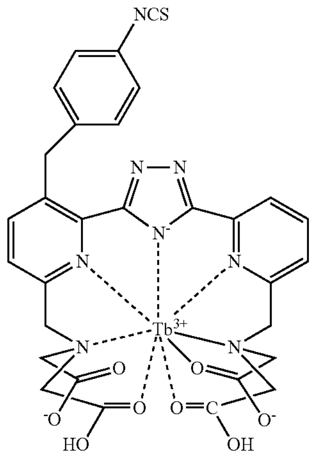

Tb-W14016

Advantageously, the fluorescent donor compound is a FRET partner selected from: a europium cryptate, a europium chelate, a terbium chelate, a terbium cryptate, a ruthenium chelate, a quantum dot, the allophycocyanins, rhodamines, cyanins, squaraines, coumarins, proflavins, acridines, fluoresceins, derivatives of boron-dipyrromethene and nitrobenzoxadiazole.

Particularly advantageously, the fluorescent donor compound is a FRET partner selected from: a europium cryptate; a europium chelate; a terbium chelate; a terbium cryptate; a ruthenium chelate; and a quantum dot; the chelates and the cryptates of europium and of terbium being particularly preferred.

Nonhydrolyzable or slowly hydrolyzable GTPs labeled with a fluorescent donor compound that may be used in the FRET method of the invention are represented by the following general formulas (1) and (2a, 2b, 2c):

1

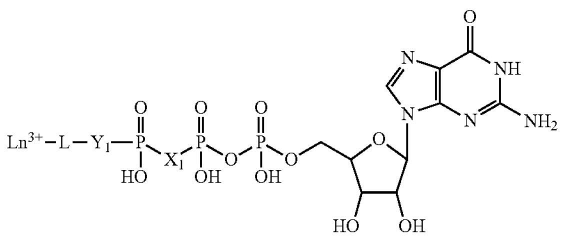

$Y_1$ = O, NH, $CH_2$
$X_1$ = O, NH, $CH_2$
L = linker divalent 2a-c

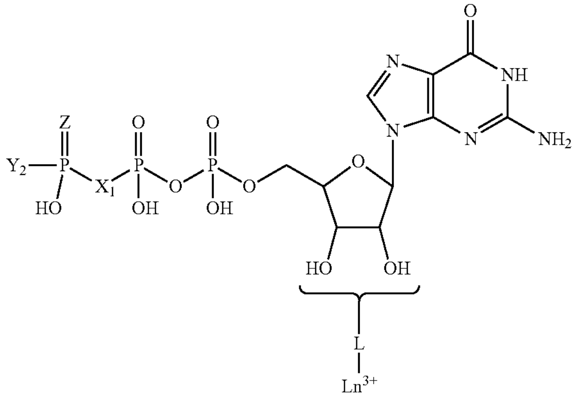

2a, Z = S, $Y_2$ = OH, $X_2$ = O;
2b, Z = O, $Y_2$ =OH, $X_2$ = NH
2c, Z = O, $Y_2$ = OH, $X_2$ = $CH_2$
L = linker divalent The labeling of the GTP analogues may be carried out at different positions of the GTP:

in the gamma position of the phosphate (O, NH, $CH_2$), or at positions 2' and 3' of the ribose In a particular embodiment, nonhydrolyzable or slowly hydrolyzable GTPs labeled with a fluorescent donor compound that may be used in the FRET method of the invention are represented by the general formula (I):

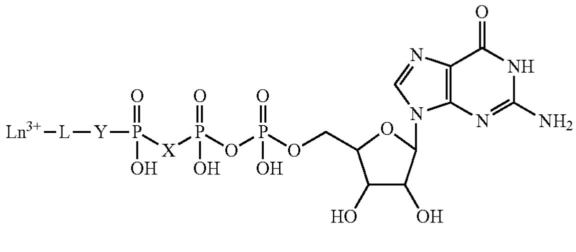

in which:

X=O, NH or $CH_2$;

Y=O, NH or $CH_2$;

L is a divalent linker;

$Ln^{3+}$ is a lanthanide complex optionally bearing a reactive group $G_3$.

“Lanthanide complex” means a chelate, a macrocycle, a cryptate or any organic species capable of complexing an atom of the lanthanide family, the lanthanide (Ln) being selected from: Eu, Sm, Tb, Gd, Dy, Nd, Er, preferably the lanthanide is Tb, Sm or Eu and even more preferably Eu or Tb.

The compounds for which Y=O are called GTP-gamma-O analogues. The compounds for which Y=NH are called GTP-gamma-N analogues. The compounds for which $Y=CH_2$ are called GTP-gamma-C analogues.

The divalent linker L is advantageously selected from:

a direct bond;

a linear or branched $C_1$-$C_{20}$, preferably $C_1$-$C_8$, alkylene group, optionally containing one or more double or triple bonds;

a $C_5$-$C_8$ cycloalkylene group; or a $C_6$-$C_{14}$ arylene group;

said alkylene, cycloalkylene or arylene groups optionally containing one or more heteroatoms, such as oxygen, nitrogen, sulfur, phosphorus or one or more carbamoyl or carboxamido groups, said alkylene, cycloalkylene or arylene groups optionally being substituted with 1 to 5, preferably 1 to 3, $C_1$-$C_8$ alkyl, $C_6$-$C_{14}$ aryl, sulfonate or oxo groups.

Even more advantageously, the divalent linker L is selected from the following groups:

$-(CH_2)_n-$ ;

$-(CH_2)_n-O-(CH_2)_m-O-(CH_2)_p-$ ;

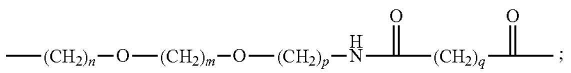

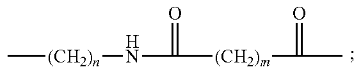

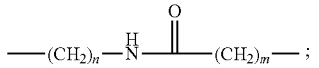

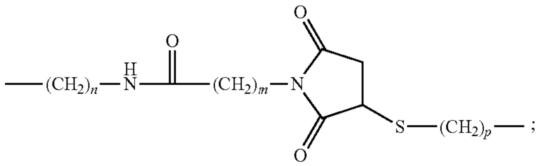

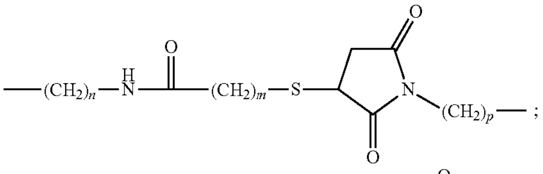

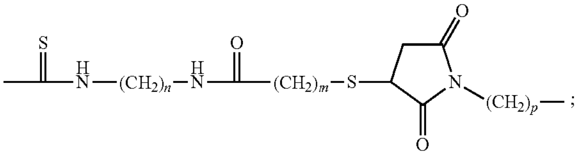

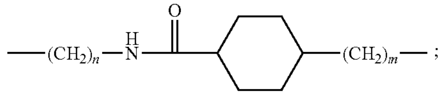

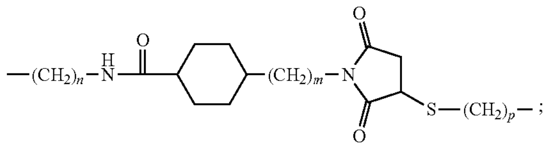

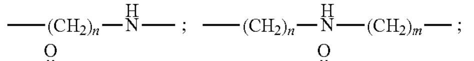

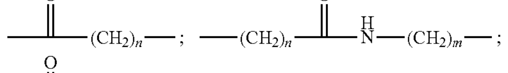

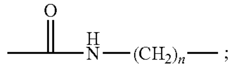

-continued

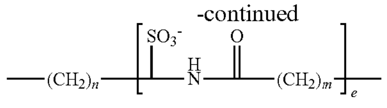

in which n, m, p, q are integers from 1 to 16, preferably from 1 to 5 and e is an integer from 1 to 6, preferably from 1 to 4.

Quite advantageously, the divalent linker L is selected from a direct bond, a linear or branched $C_1$-$C_8$ alkylene group or a group of formula:

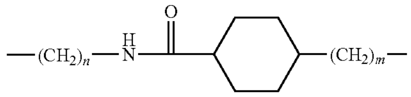

;

The divalent linker L is preferably selected from:

$-(CH_2)_n-$; $-(CH_2)_n-O-(CH_2)_m-O-(CH_2)_p-$;

the group $-(CH_2)_n-$ being quite particularly preferred.

The group L may also advantageously be a group of formula:

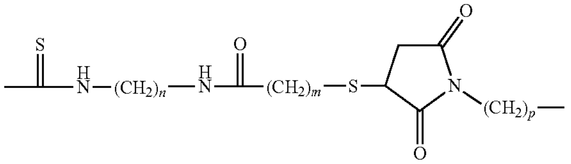

in which m, n and p are integers from 1 to 16, preferably from 1 to 5.

The reactive group $G_3$ is selected from one of the following groups: an acrylamide, an optionally activated amine (for example a cadaverine or an ethylenediamine), an activated ester, an aldehyde, an alkyl halide, an anhydride, an aniline, an azide, an aziridine, a carboxylic acid, a diazoalkane, a haloacetamide, a halotriazine, such as monochlorotriazine, dichlorotriazine, a hydrazine (including the hydrazides), an imido ester, an isocyanate, an isothiocyanate, a maleimide, a sulfonyl halide, a thiol, a ketone, an acid halide, a succinimidyl ester, a hydroxysuccinimidyl ester, a hydroxysulfosuccinimidyl ester, an azidonitrophenyl, an azidophenyl, a 3-(2-pyridyldithio)-propionamide, a glyoxal, a triazine, an acetylene group, and in particular a group selected from the groups with the formulas:

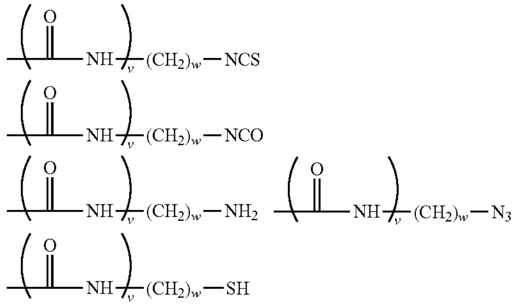

-continued

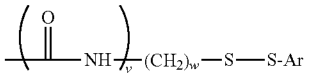

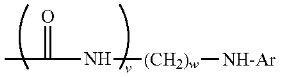

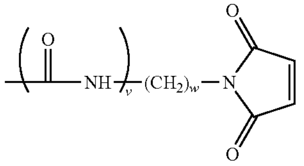

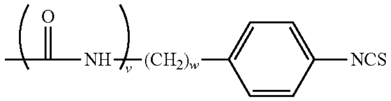

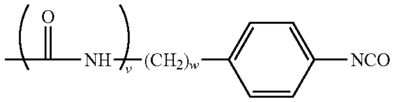

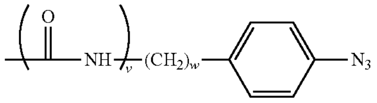

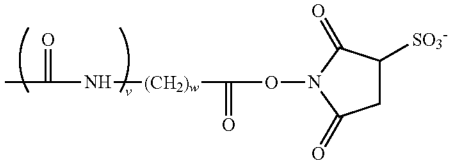

-continued

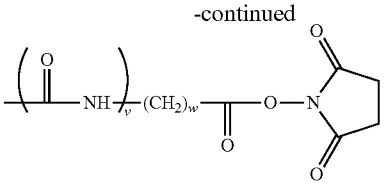

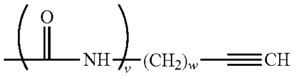

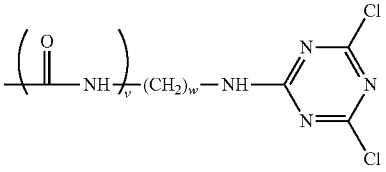

in which w varies from 0 to 8 and v is equal to 0 or 1, and Ar is a saturated or unsaturated heterocycle with 5 or 6 ring members, comprising 1 to 3 heteroatoms, optionally substituted with a halogen atom.

Preferably, the reactive group $G_3$ is selected from an amine (optionally protected in the form —NHBoc), a succinimidyl ester, a hydroxysuccinimidyl ester, a haloacetamide, a hydrazine, a halotriazine, an isothiocyanate, a maleimide group, or a carboxylic acid (optionally protected in the form of a group —$CO_2Me$, —$CO_2tBu$). In the latter case, the acid will have to be activated in the ester form so as to be able to react with a nucleophilic species. The lanthanide complex Ln3+ is selected advantageously from one of the complexes given hereunder:

C1

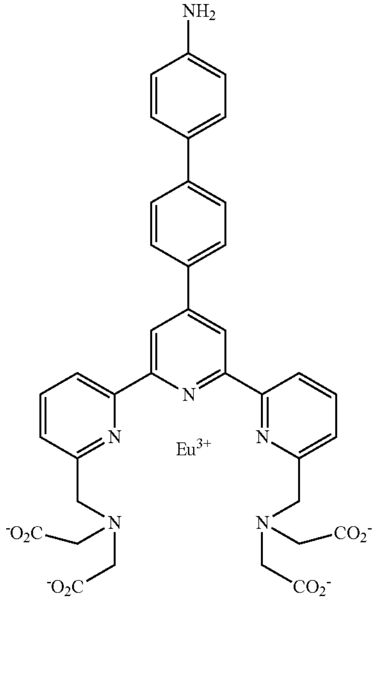

C2

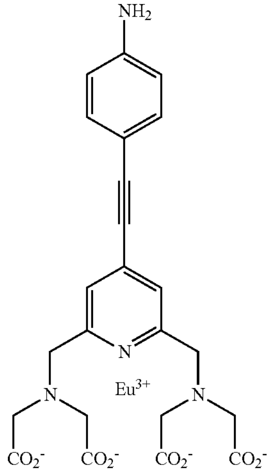

-continued
C3
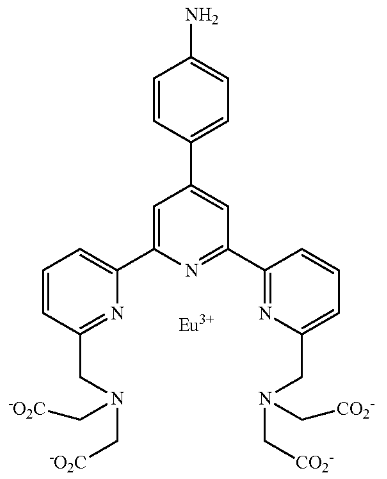
C4
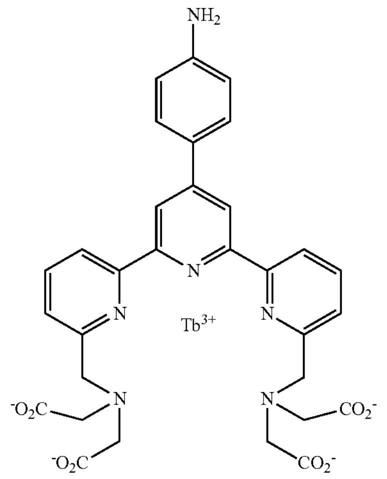
C5
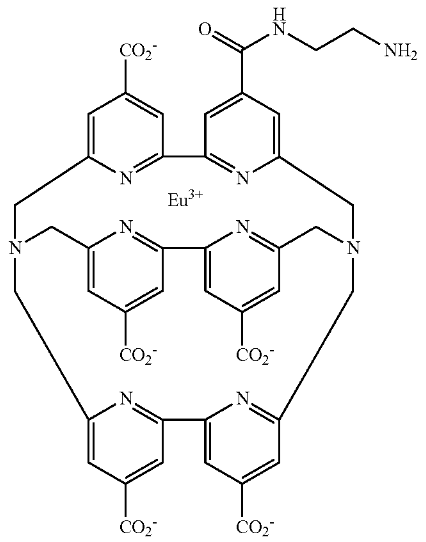
C6
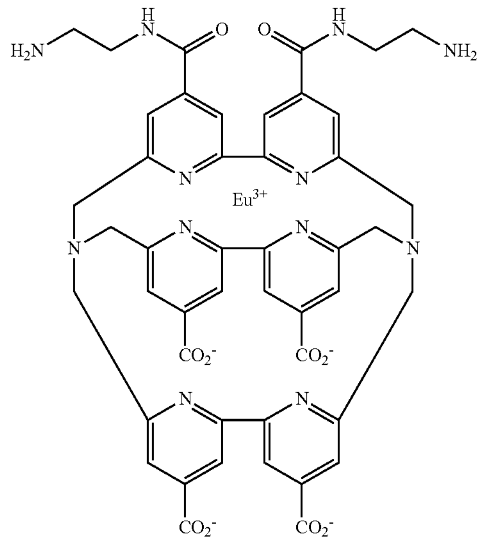
C7
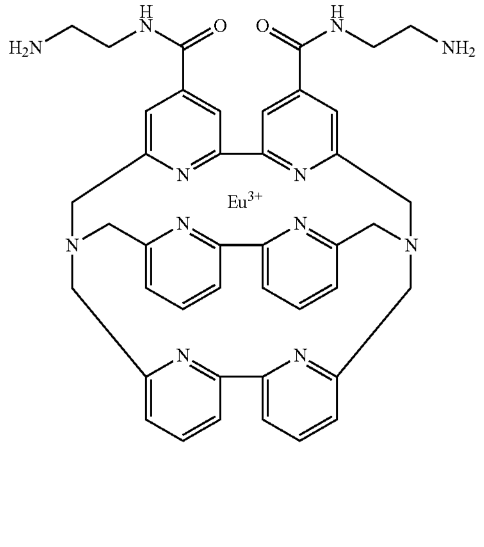
C8
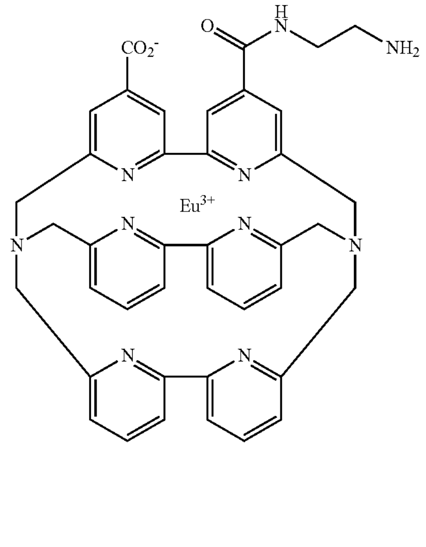

-continued
C9
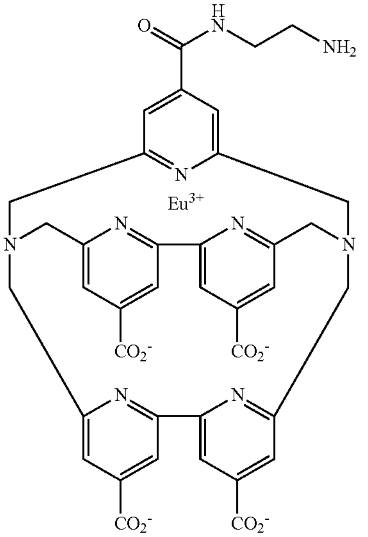
C10
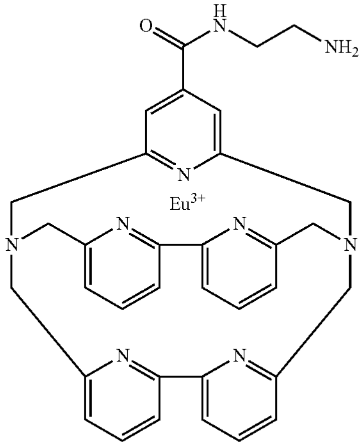
C11
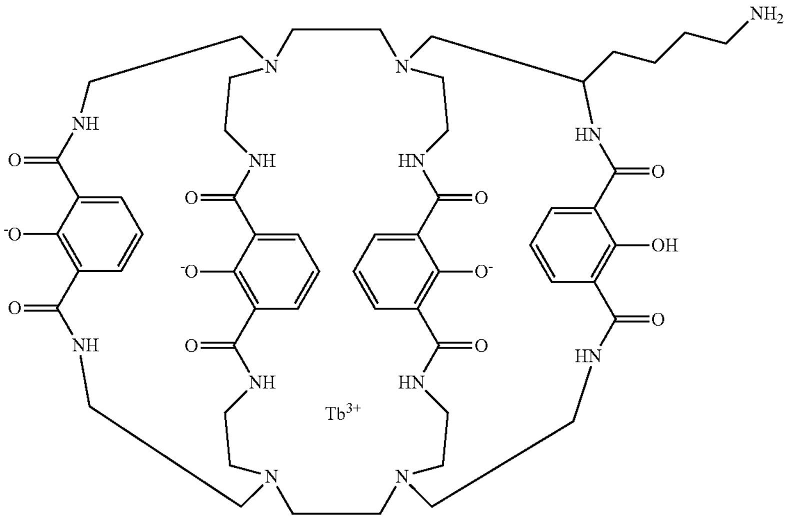

-continued
C12
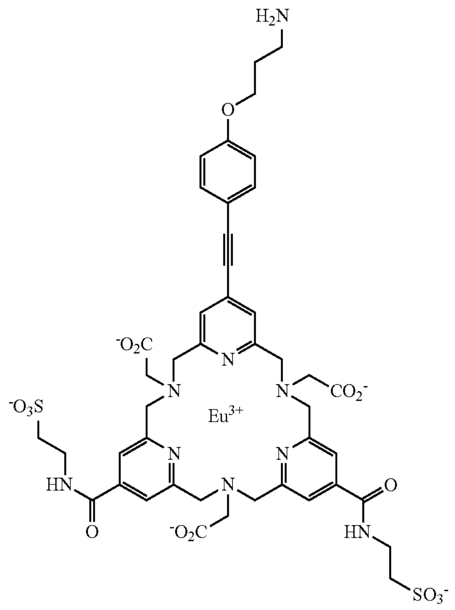
C13
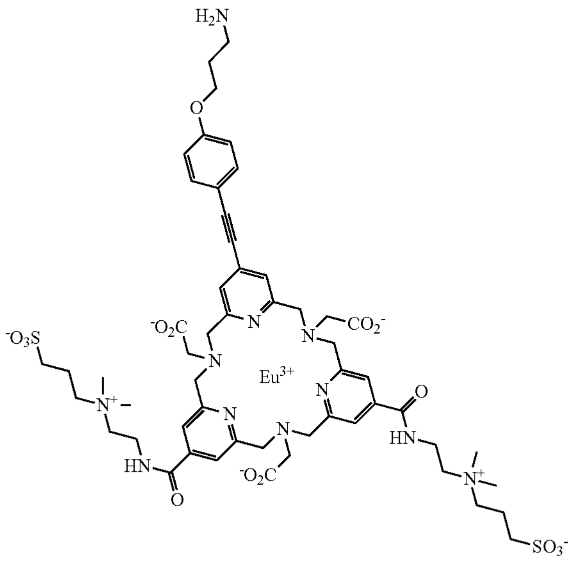
C14
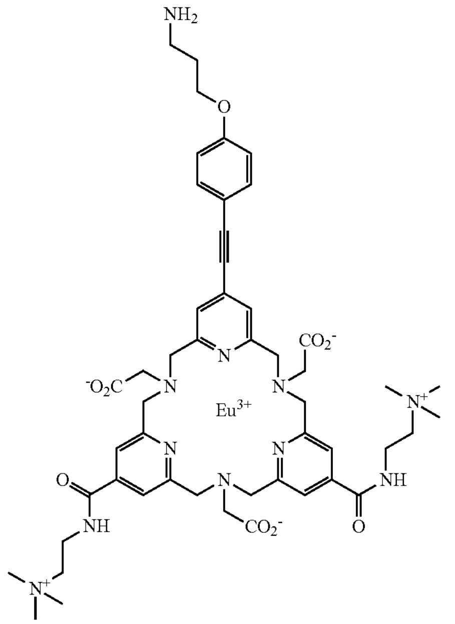
C15
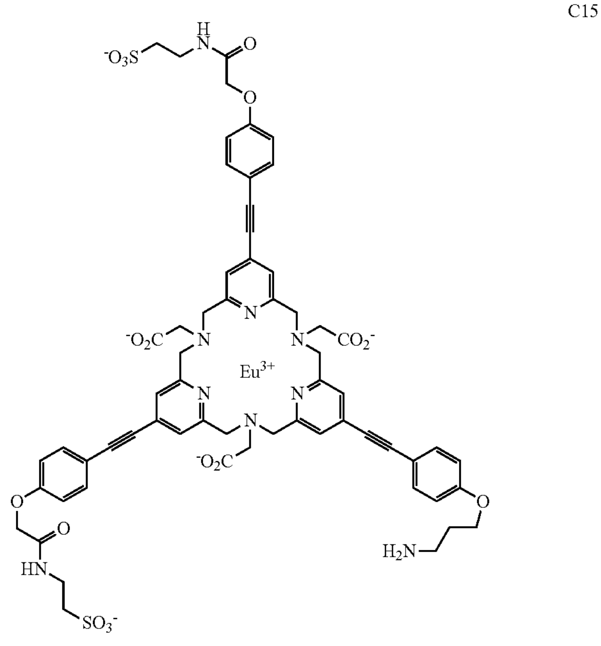

-continued
C16
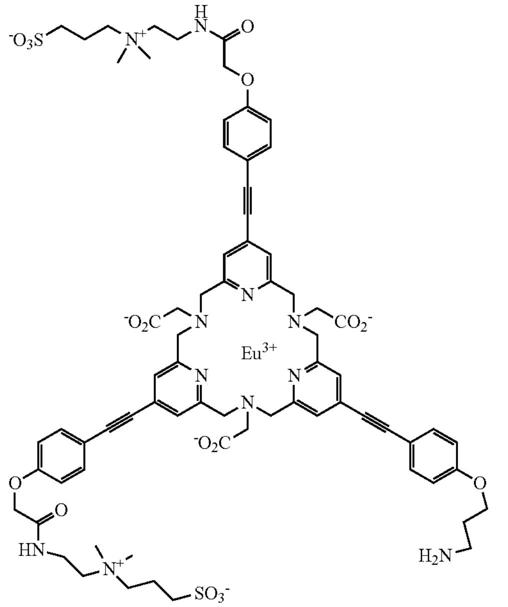
C17
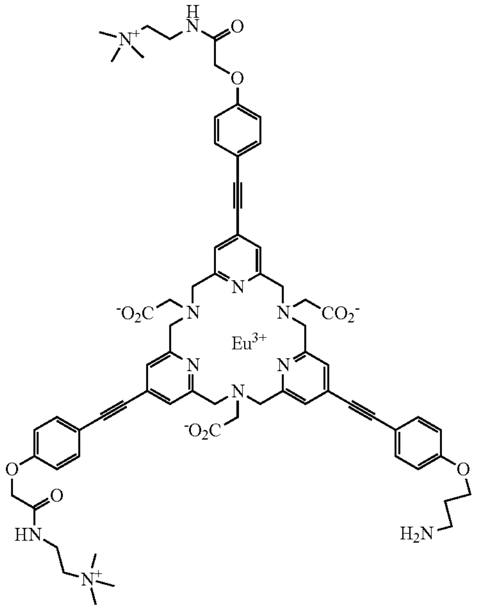
C18
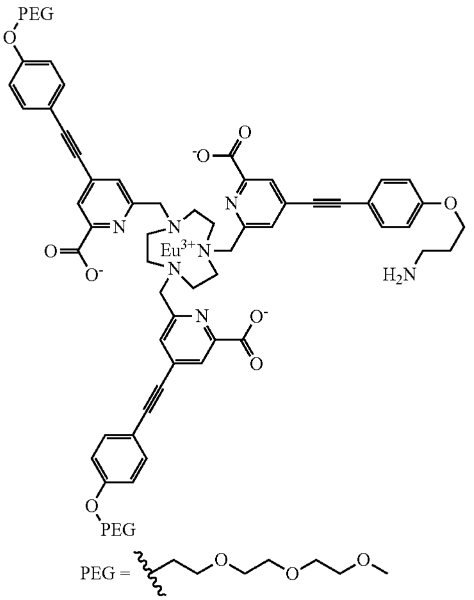
C19
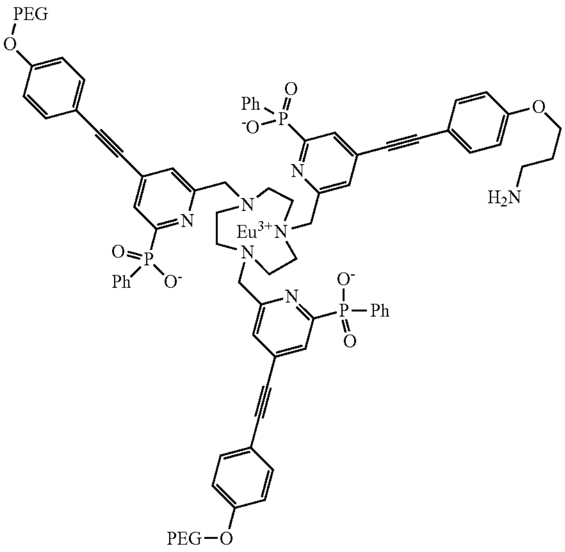

-continued
C20
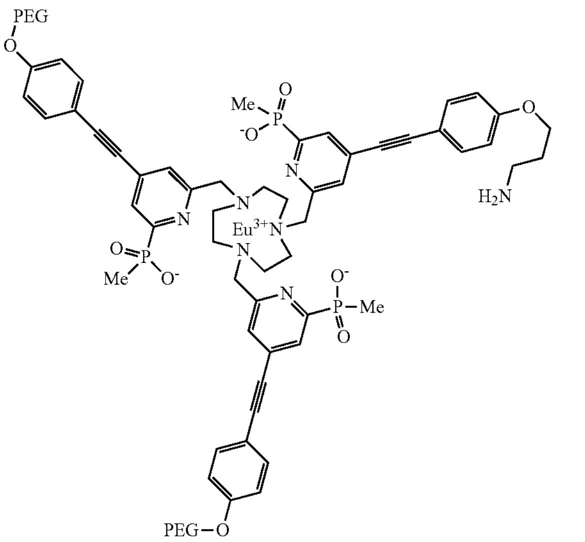
C21
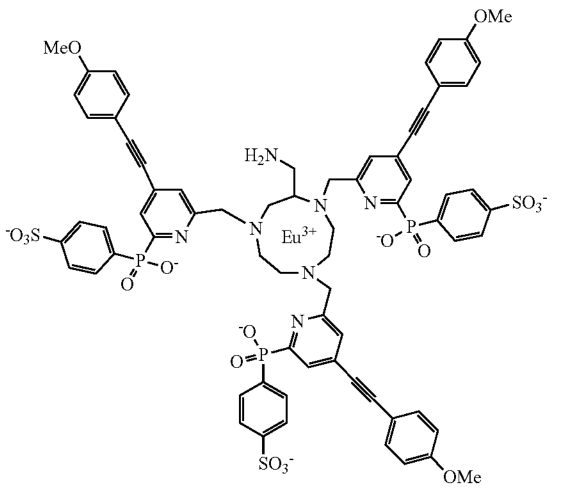
C22
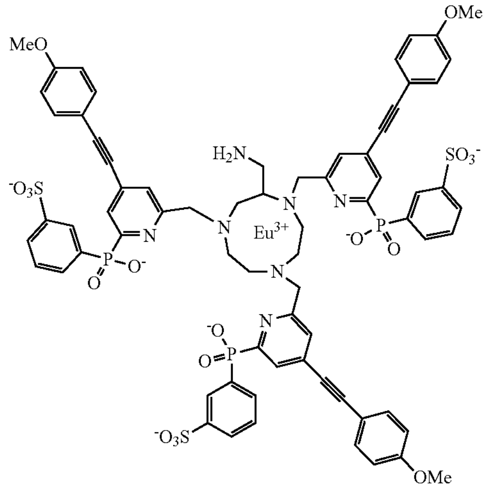
C23
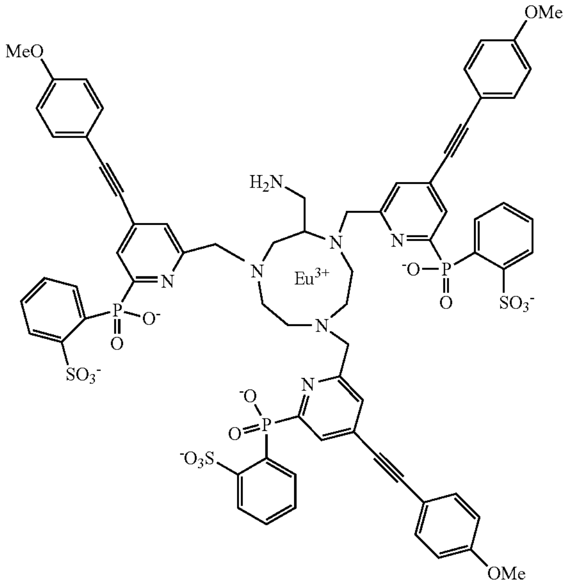

-continued
C24
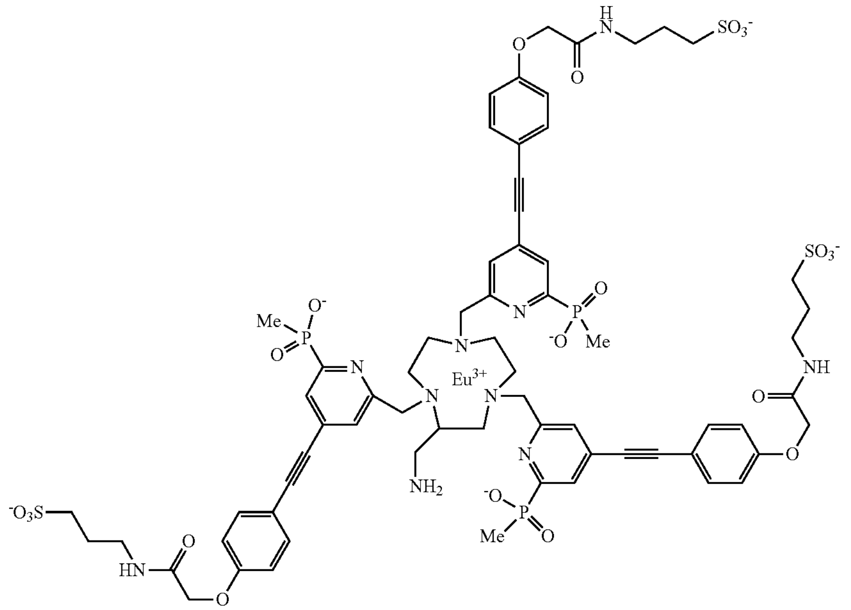
C25
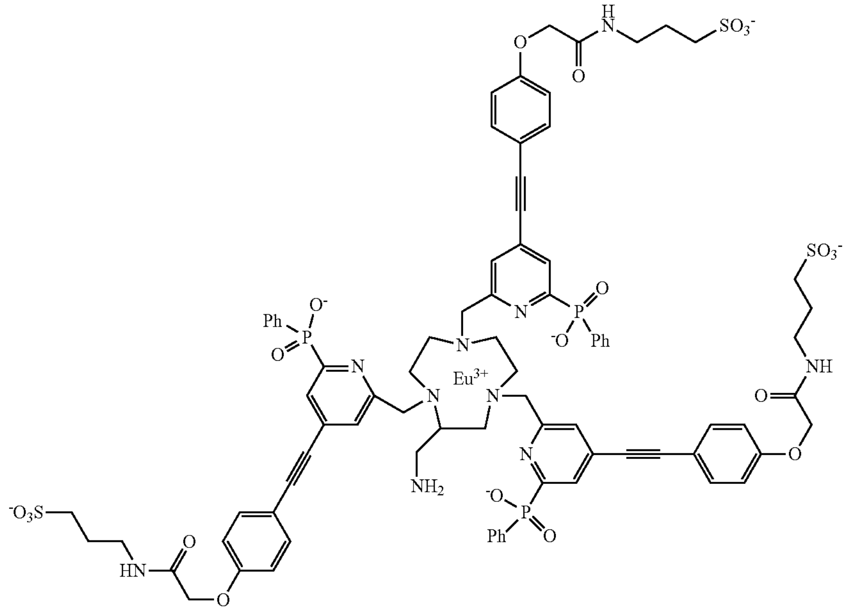

-continued
C26
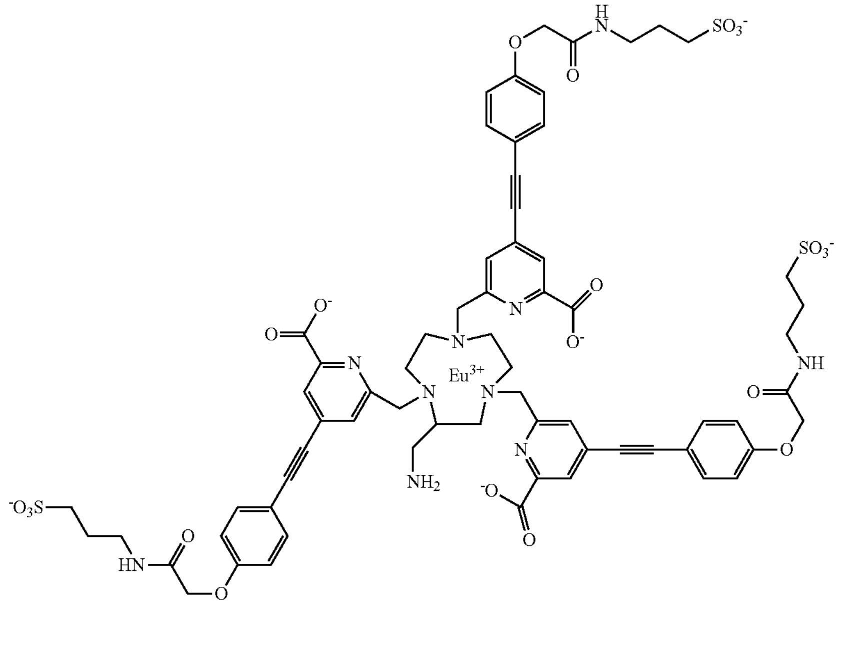
C27
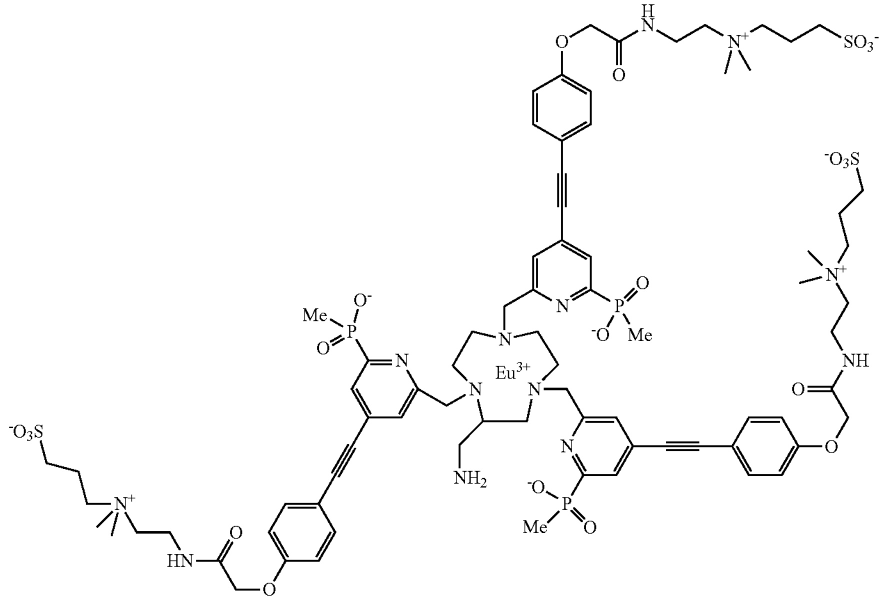

-continued
C28
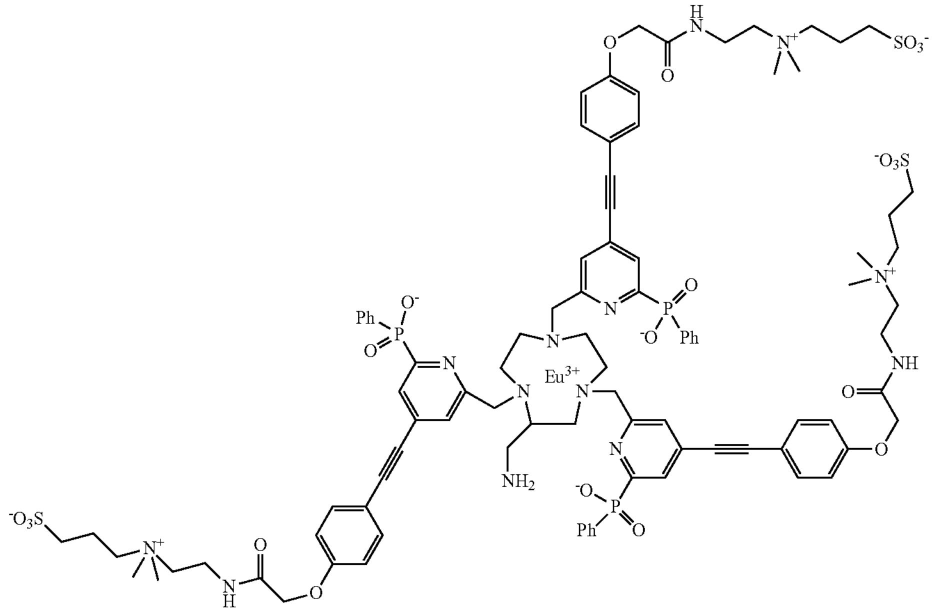
C29
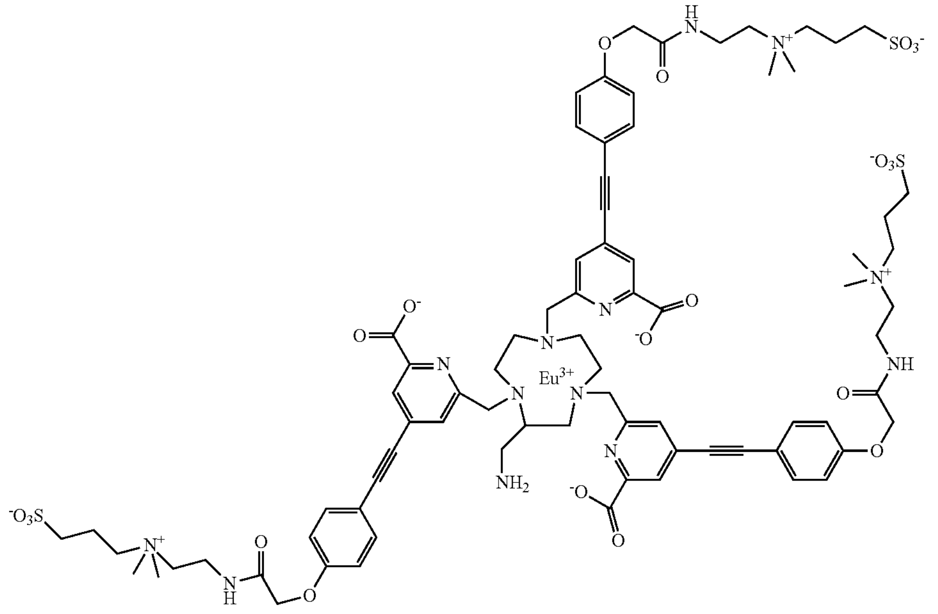

-continued
C30
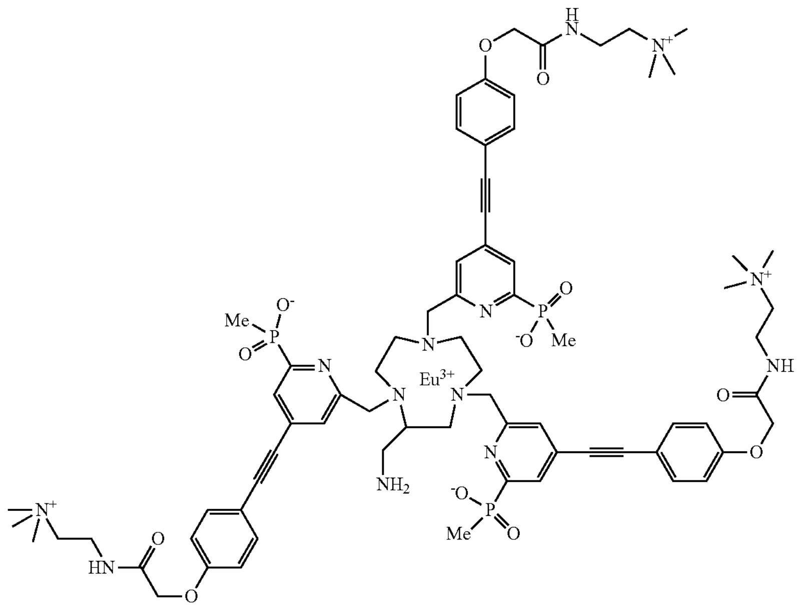
C31
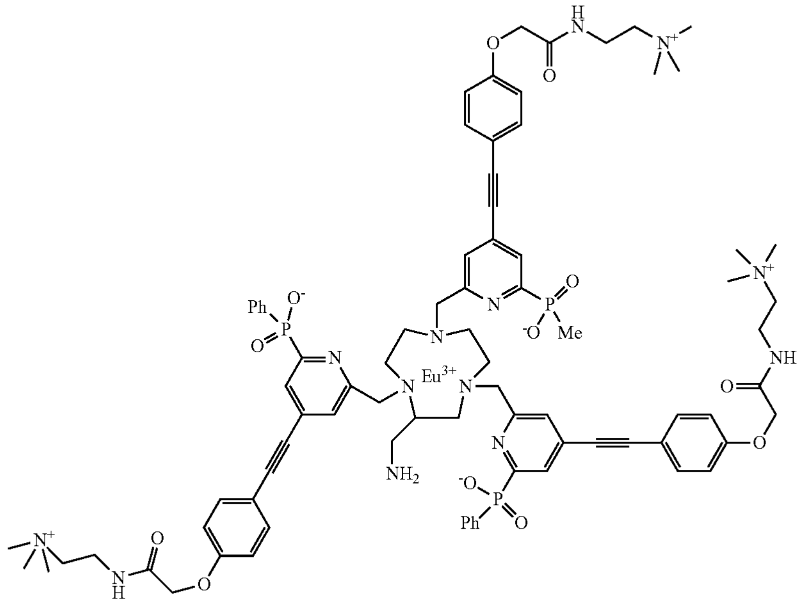

-continued
C32
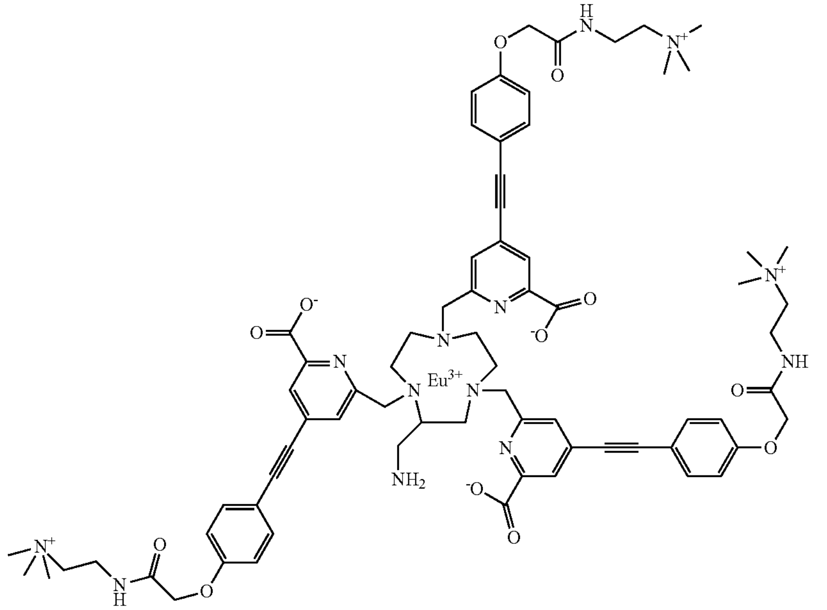
C33
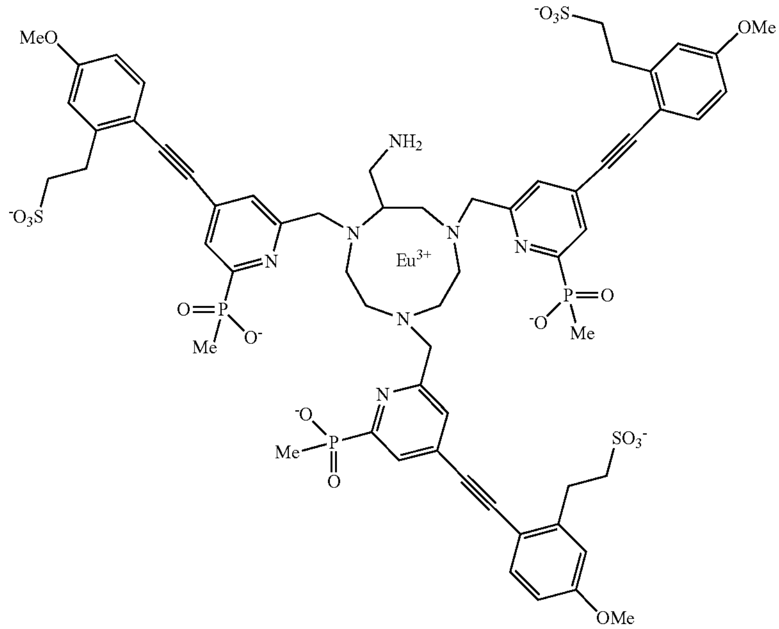

-continued
C34
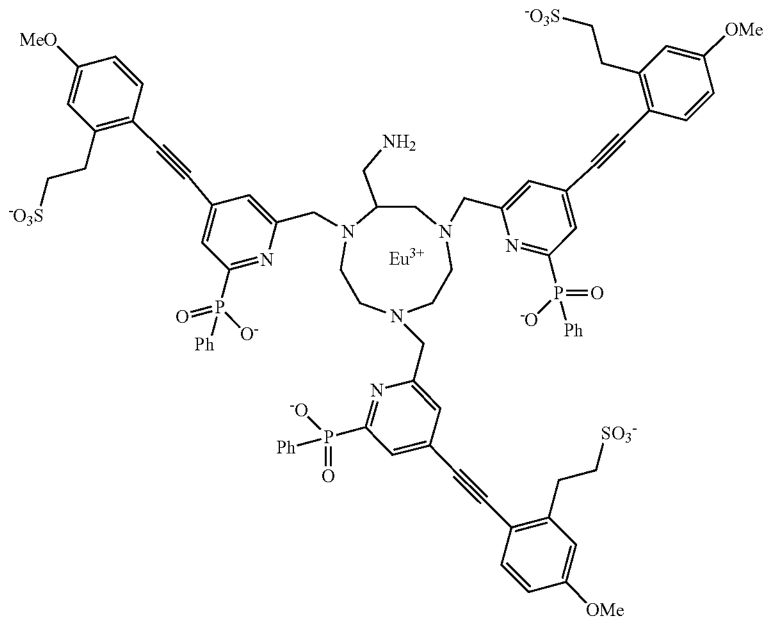
C35
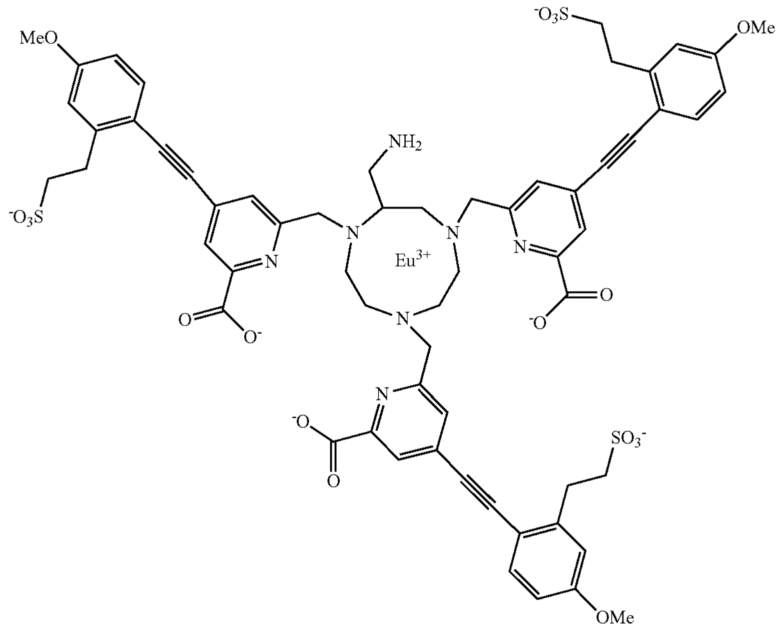

-continued
C36
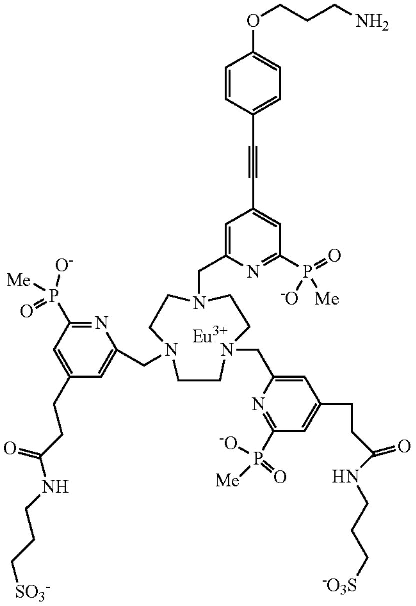
C37
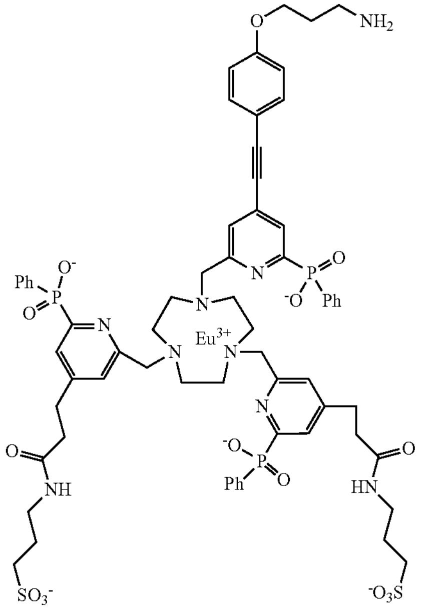
C38
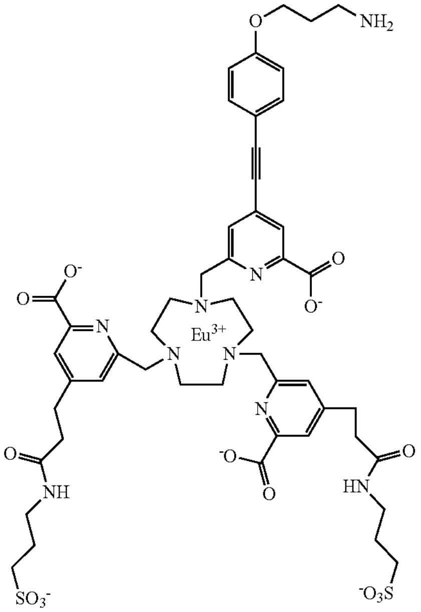
C39
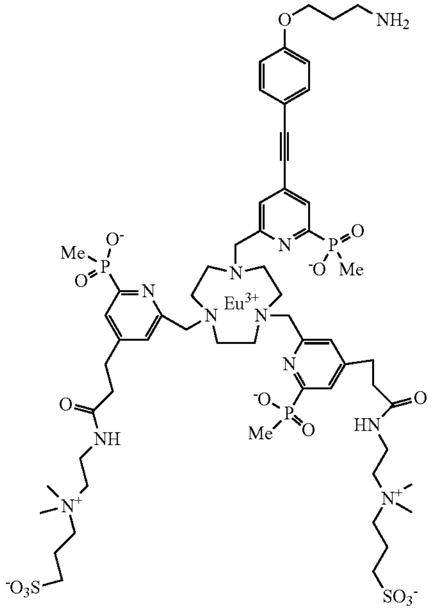

-continued
C40
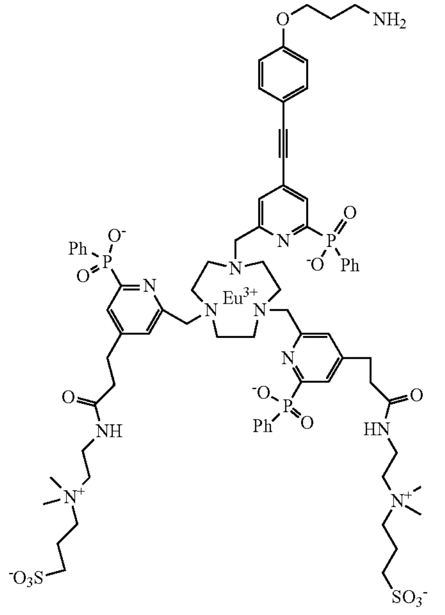
C41
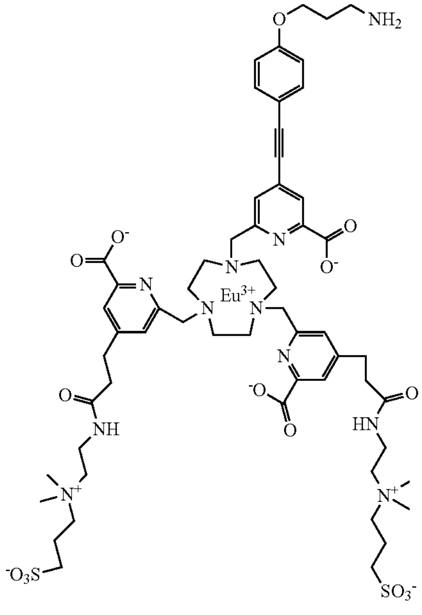
C42
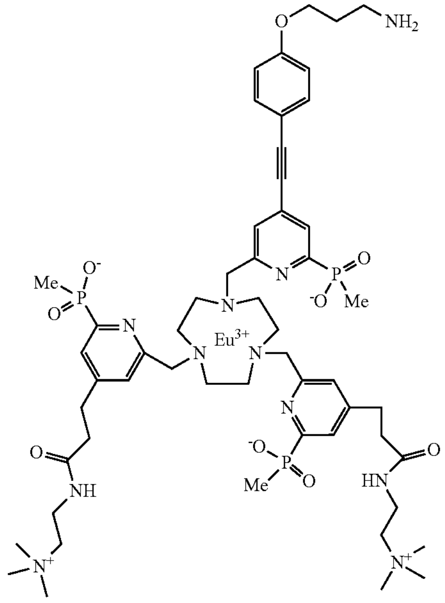
C43
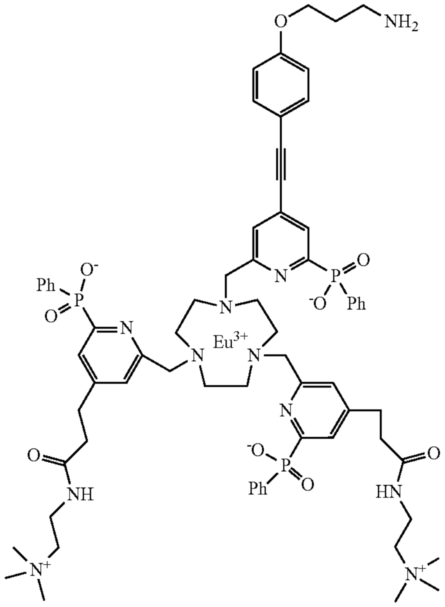

-continued
C44
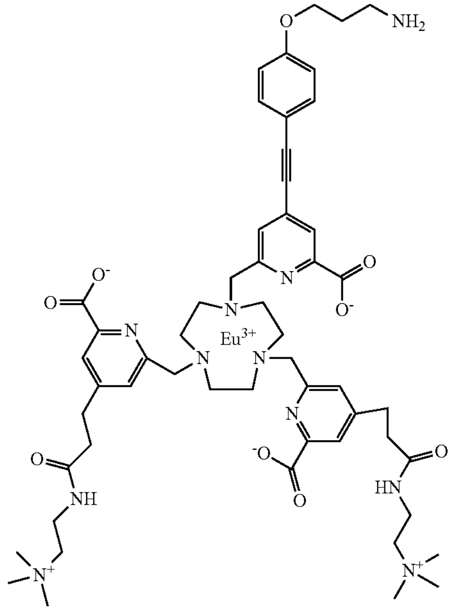
C45
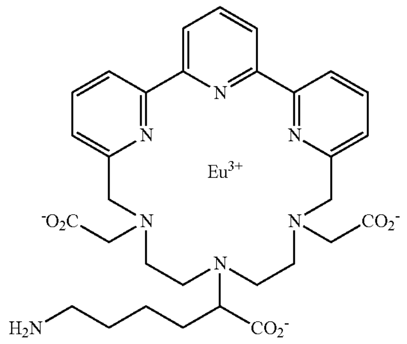
C46
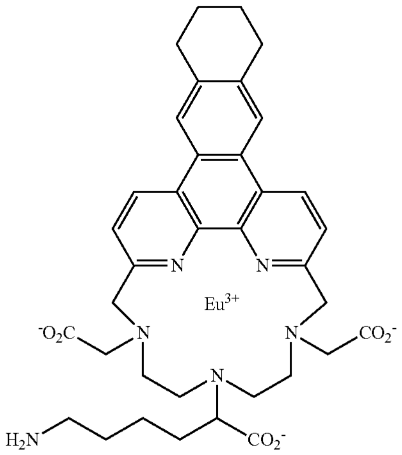
C47
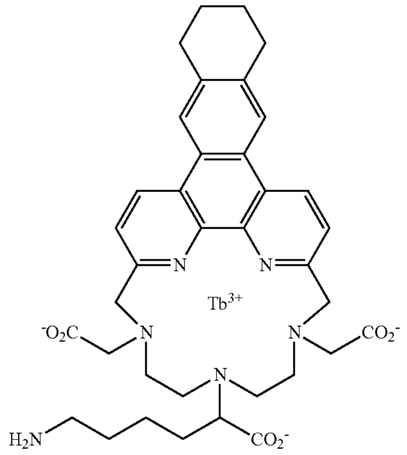
C48
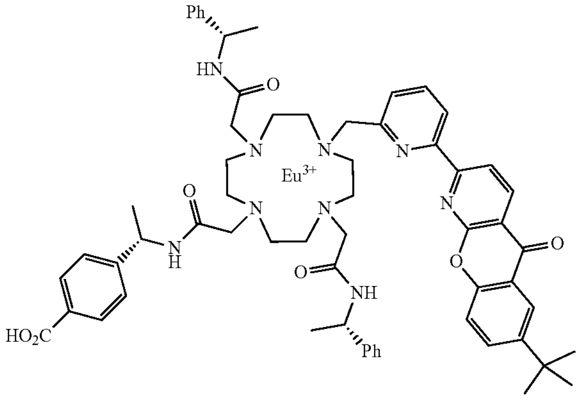

-continued
C49
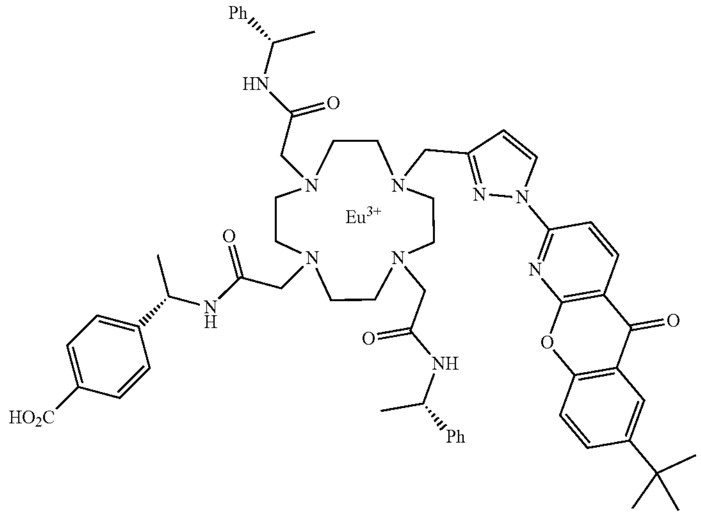
C50
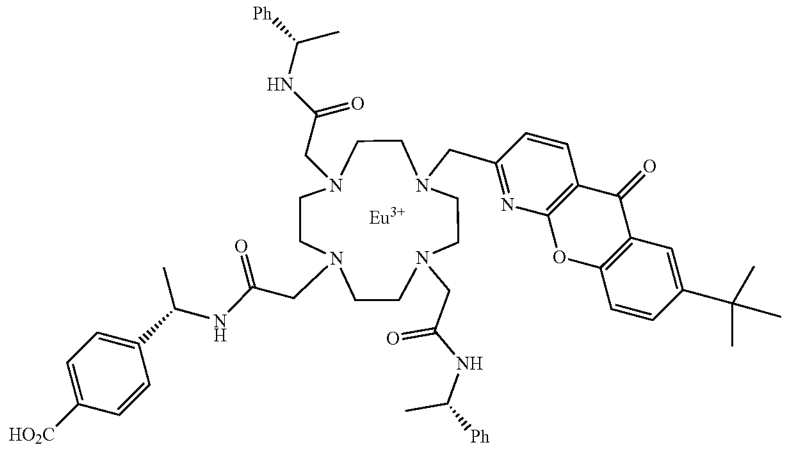
C51
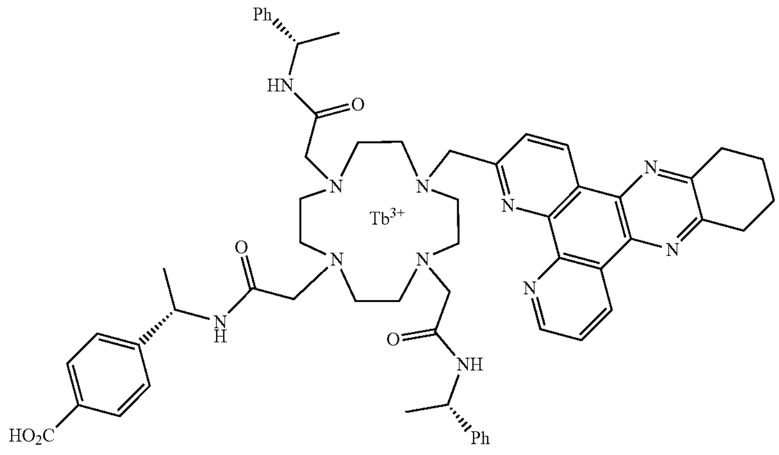

-continued
C52
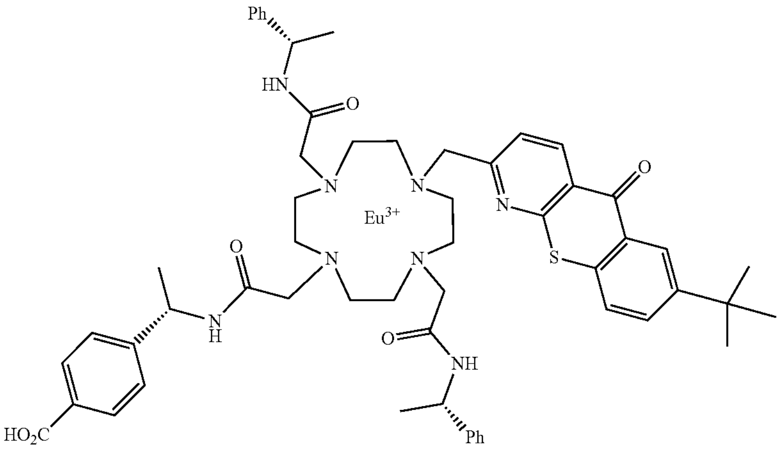
C53
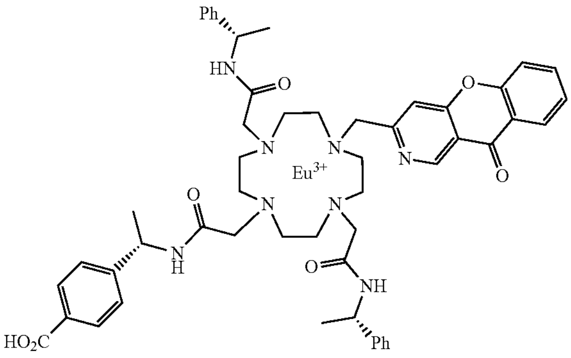
C54
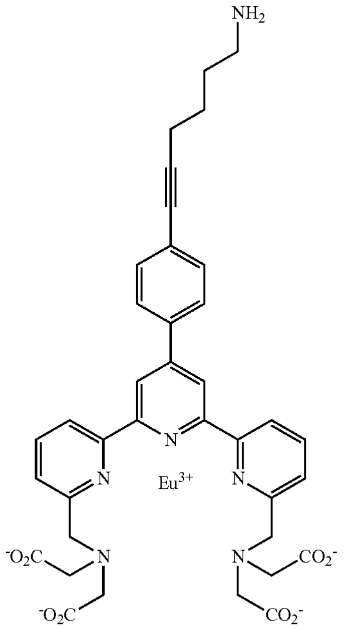
C55
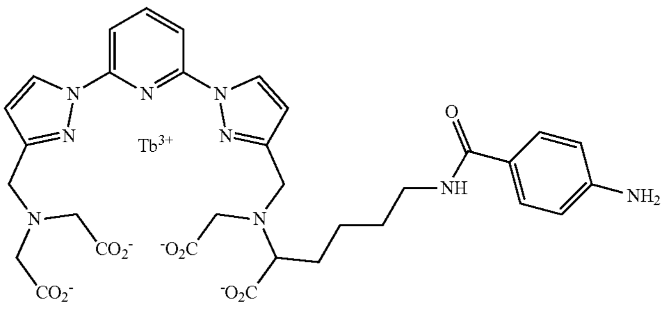

-continued
C56
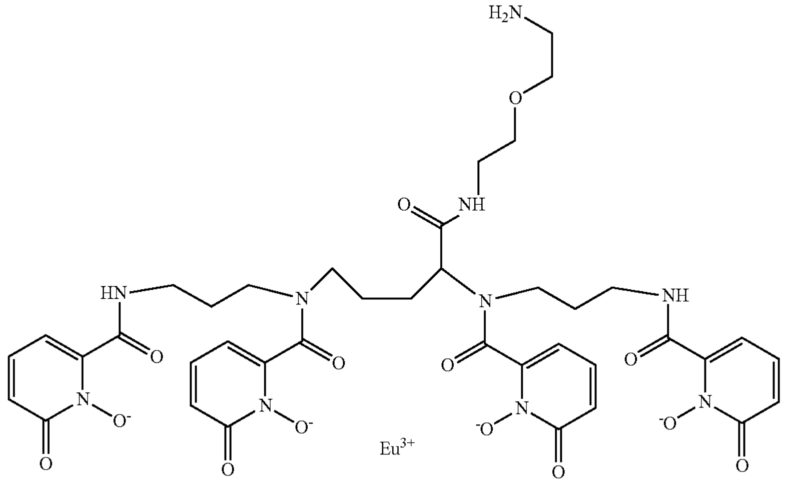
C57
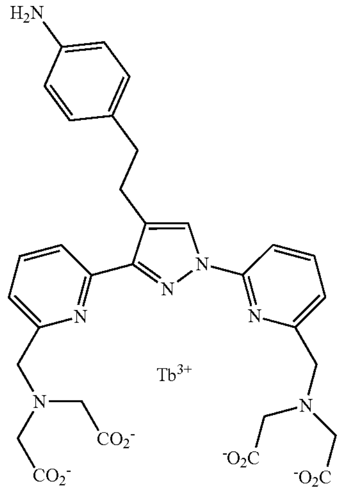
C58
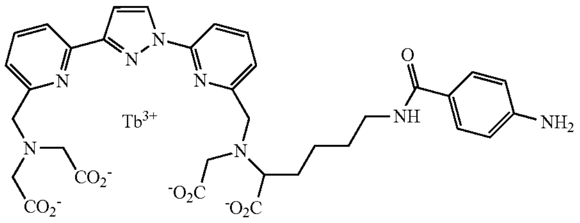
C59
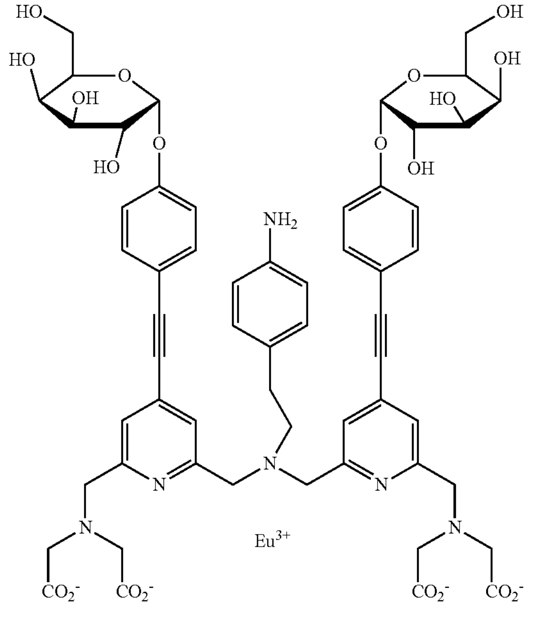
C60
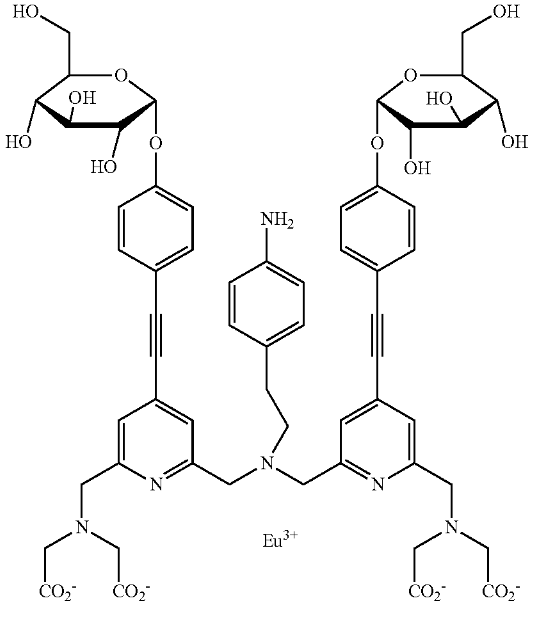

-continued
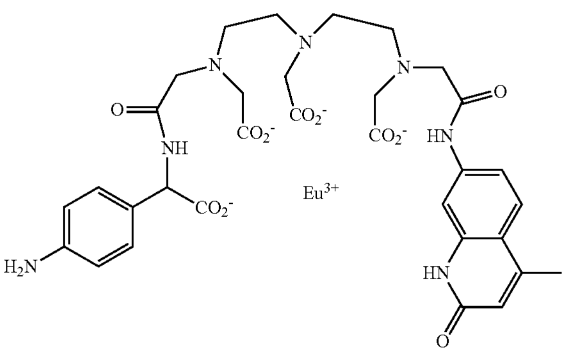
C61
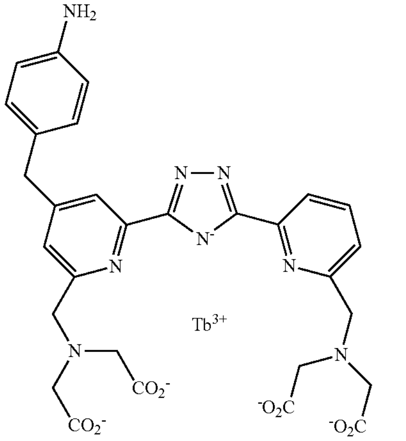
C62
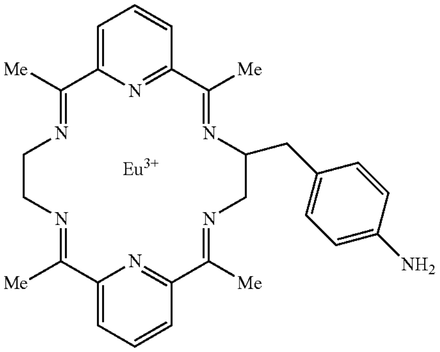
C63
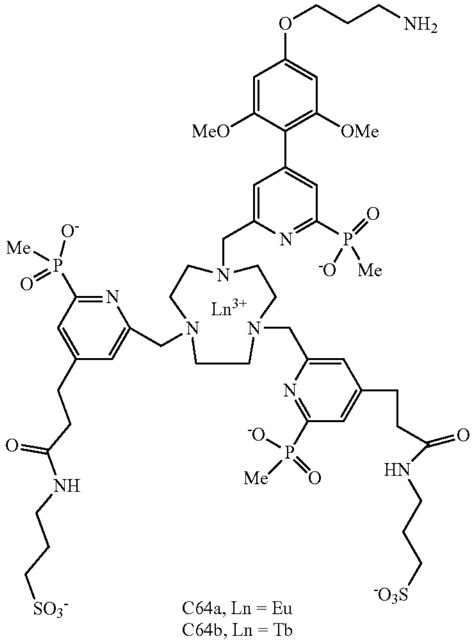
C64a, Ln = Eu
C64b, Ln = Tb -continued
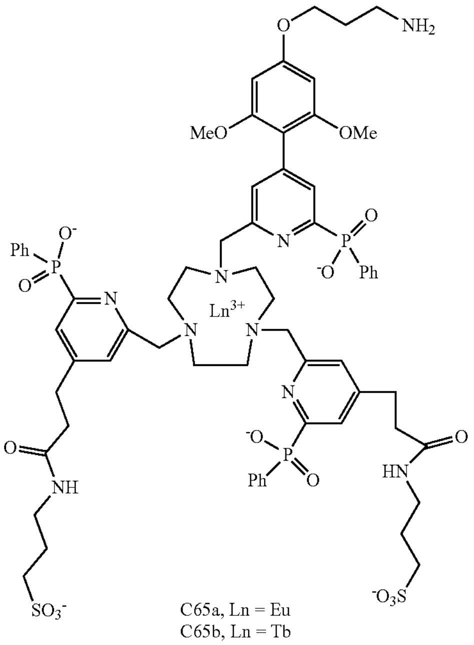
C65a, Ln = Eu
C65b, Ln = Tb
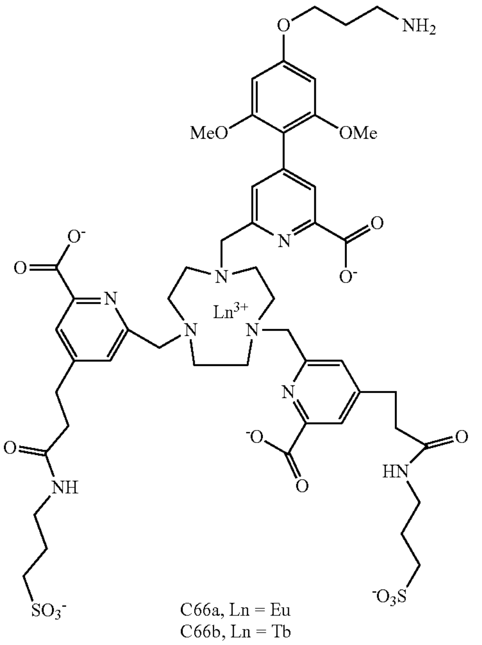
C66a, Ln = Eu
C66b, Ln = Tb
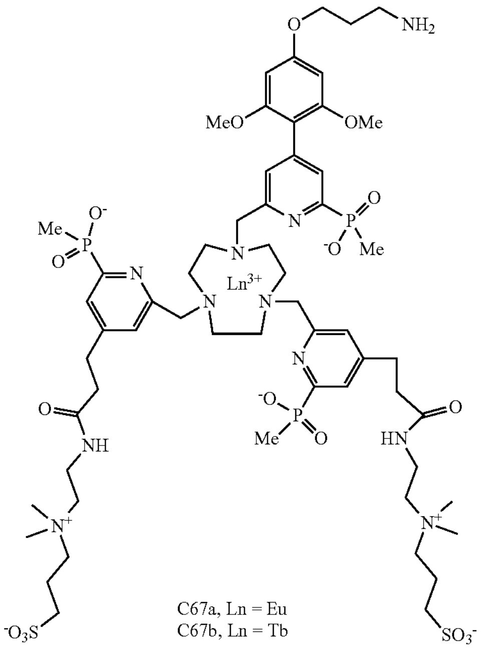
C67a, Ln = Eu
C67b, Ln = Tb
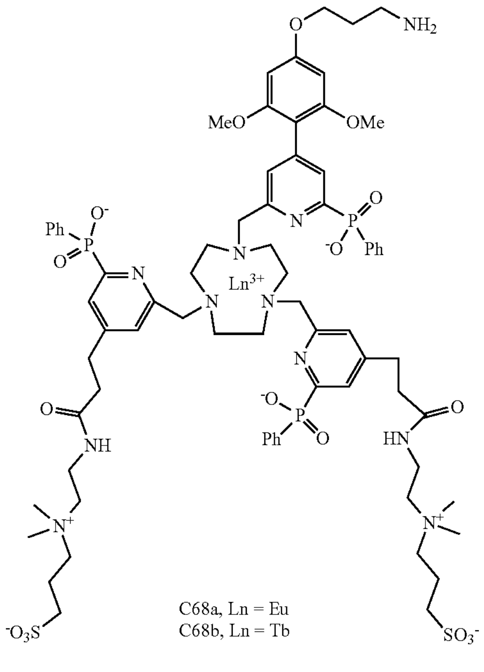
C68a, Ln = Eu
C68b, Ln = Tb -continued
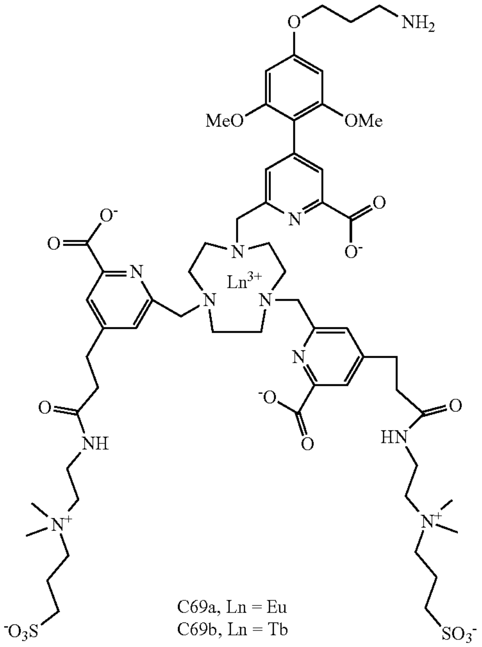
C69a, Ln = Eu
C69b, Ln = Tb
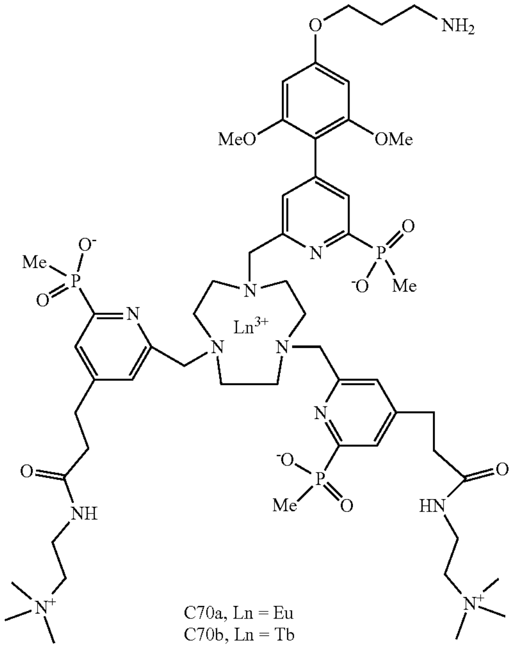
C70a, Ln = Eu
C70b, Ln = Tb
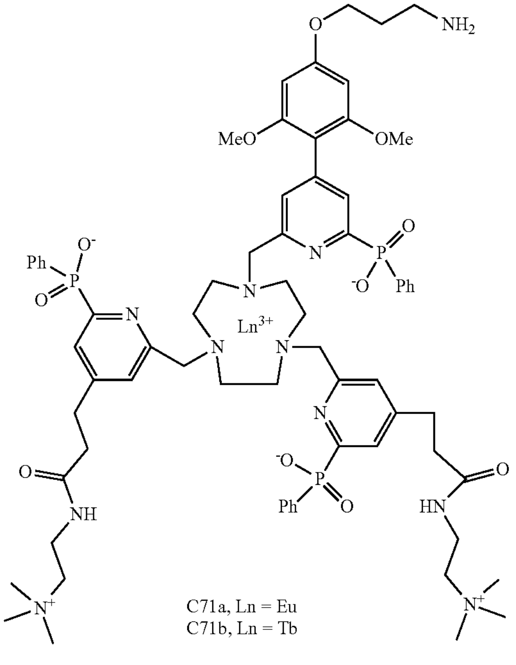
C71a, Ln = Eu
C71b, Ln = Tb
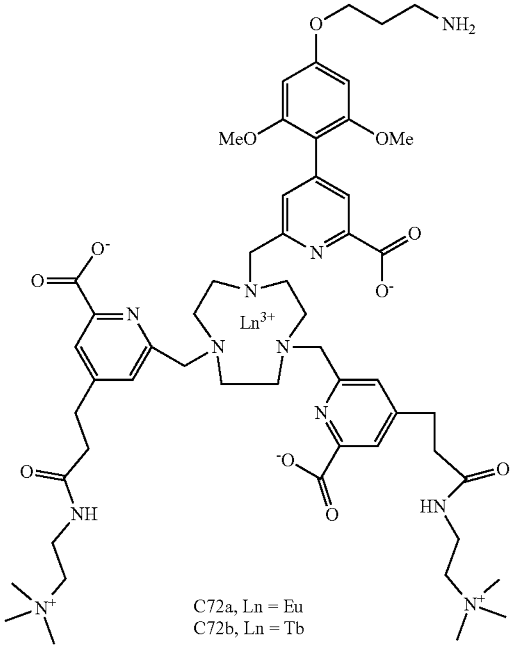
C72a, Ln = Eu
C72b, Ln = Tb -continued
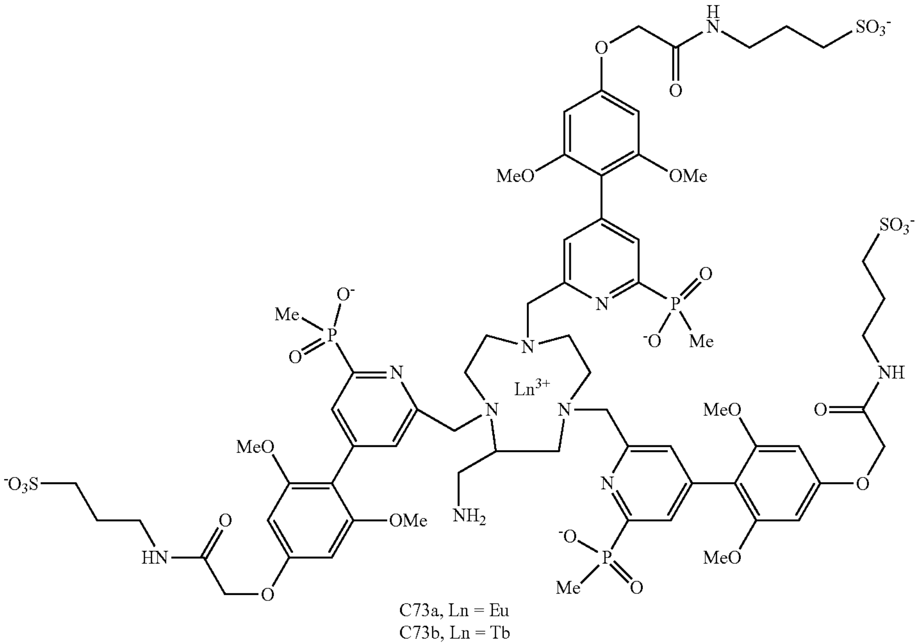
C73a, Ln = Eu
C73b, Ln = Tb
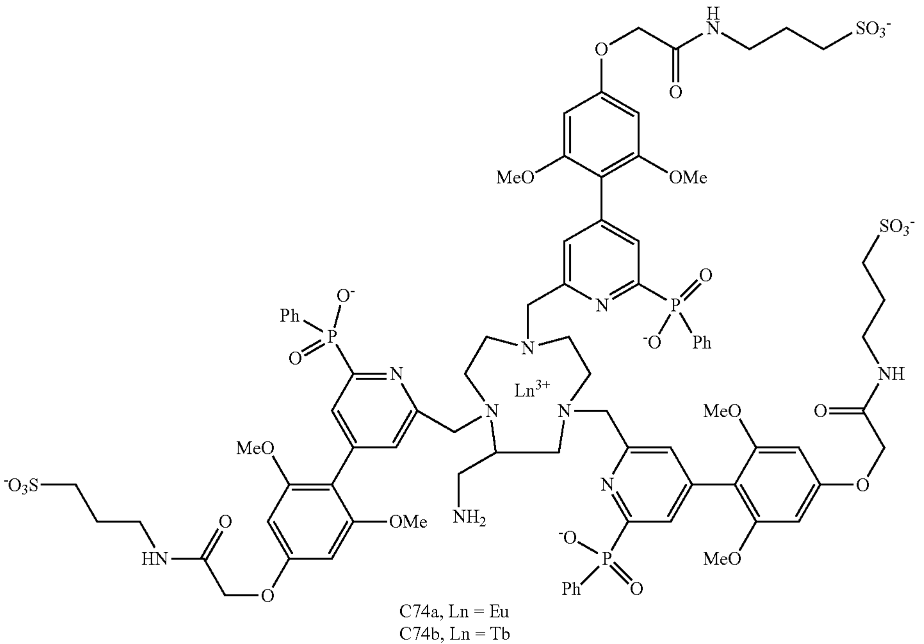
C74a, Ln = Eu
C74b, Ln = Tb -continued
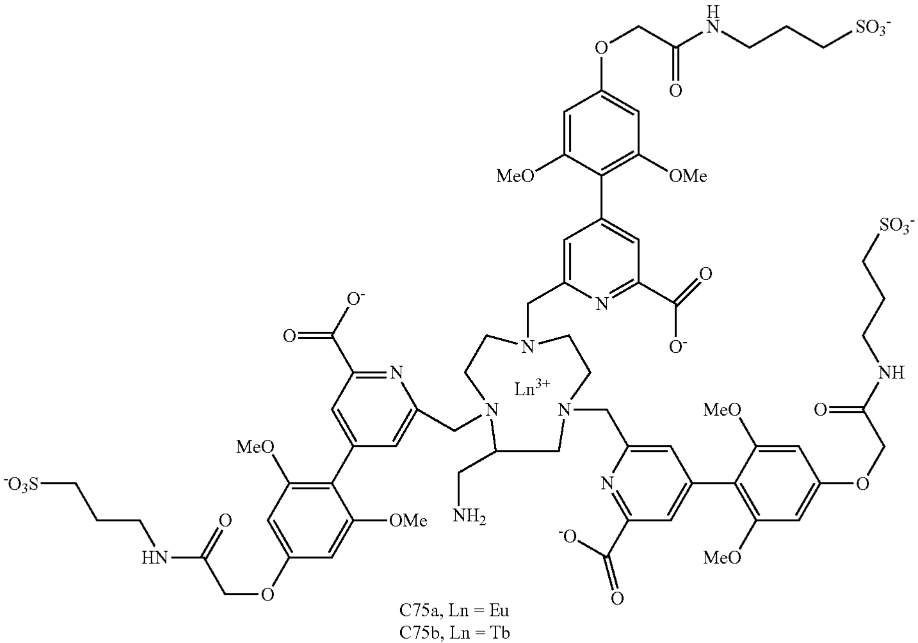
C75a, Ln = Eu
C75b, Ln = Tb
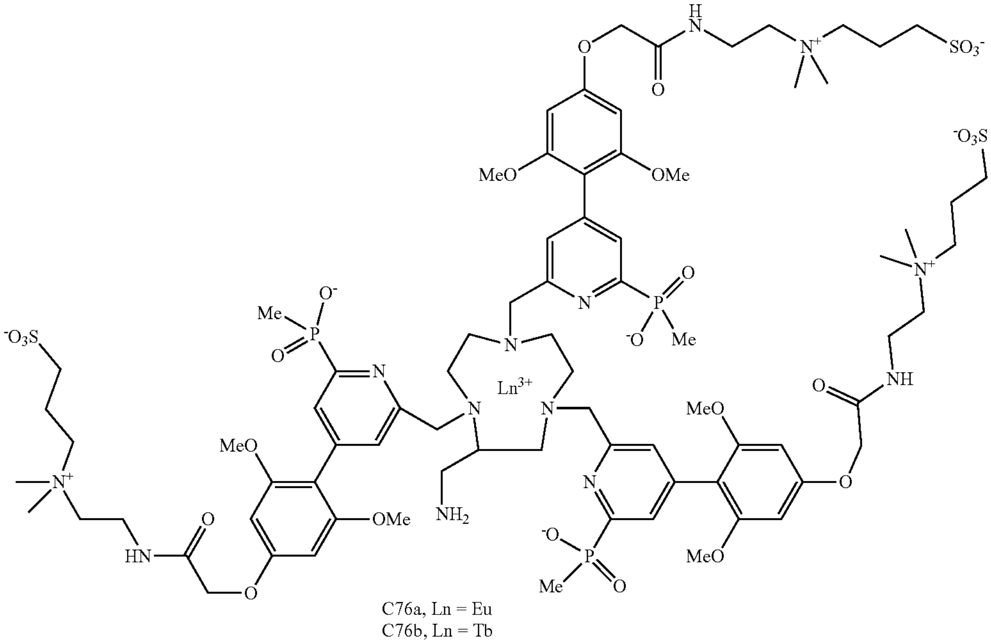
C76a, Ln = Eu
C76b, Ln = Tb -continued
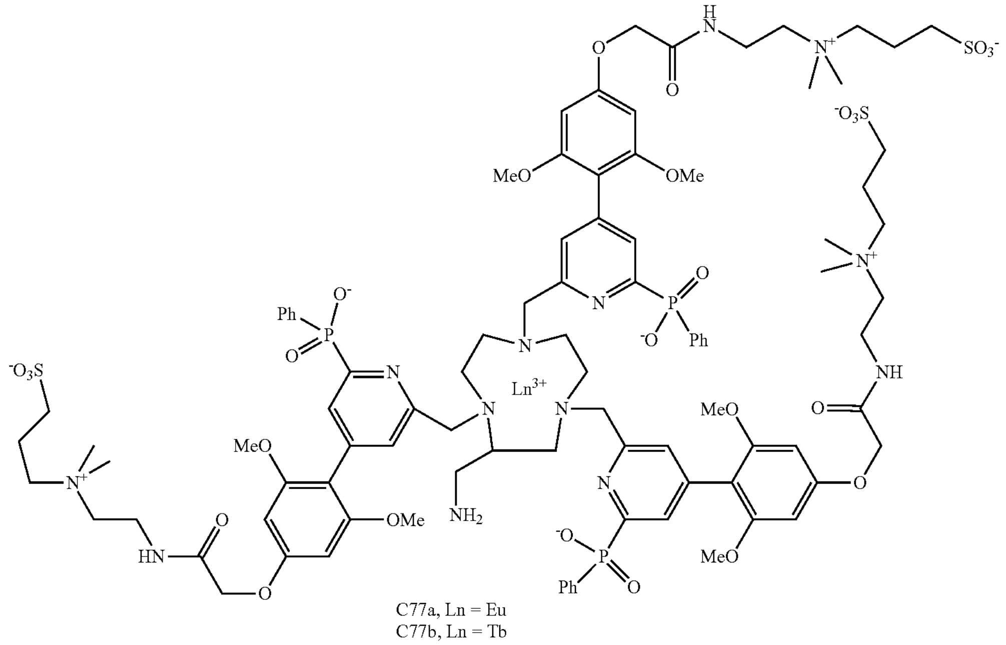
C77a, Ln = Eu
C77b, Ln = Tb
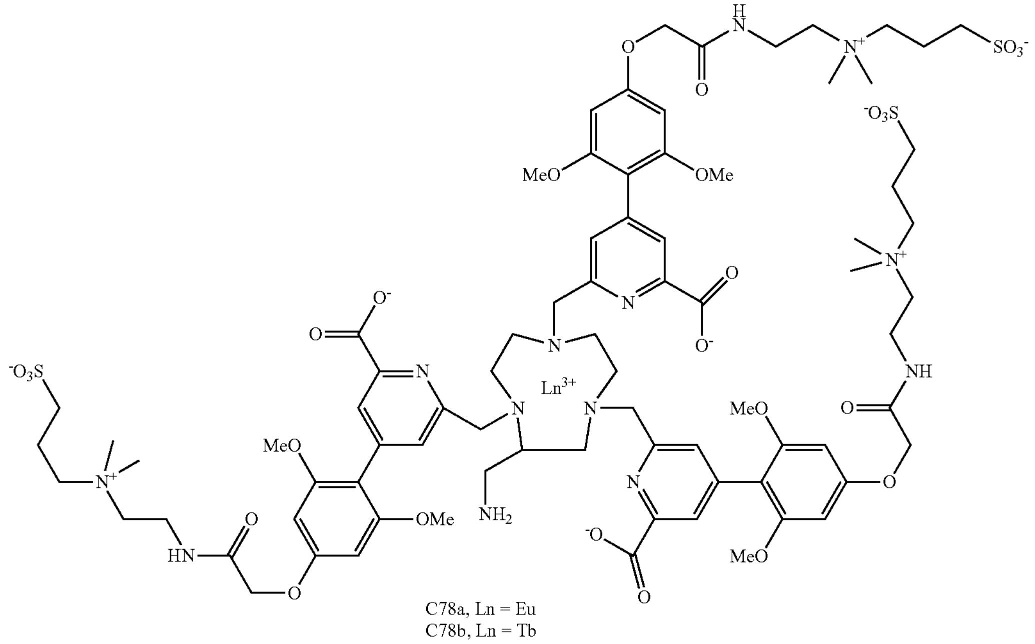
C78a, Ln = Eu
C78b, Ln = Tb -continued
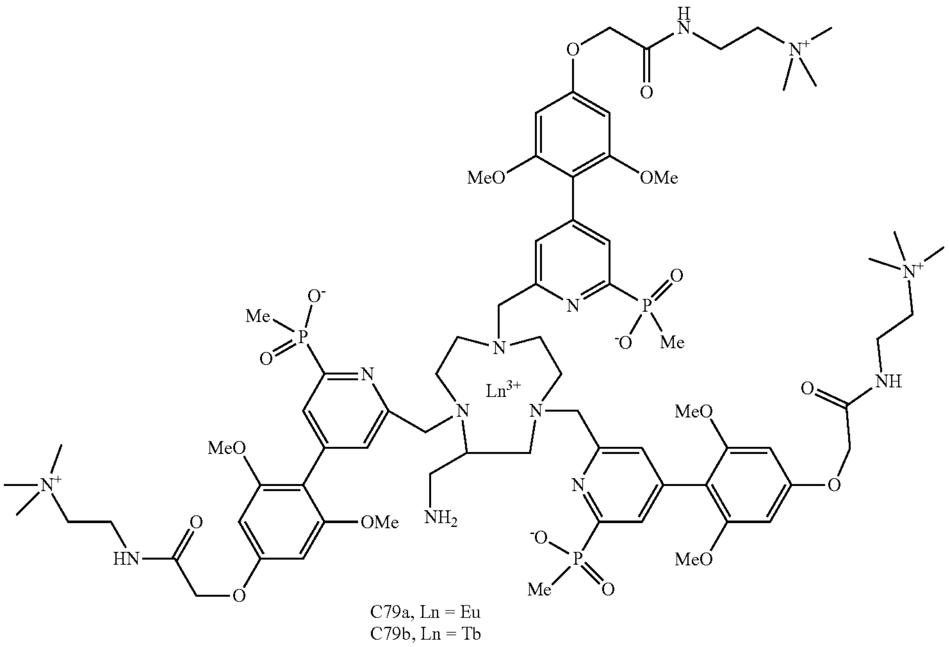
C79a, Ln = Eu
C79b, Ln = Tb
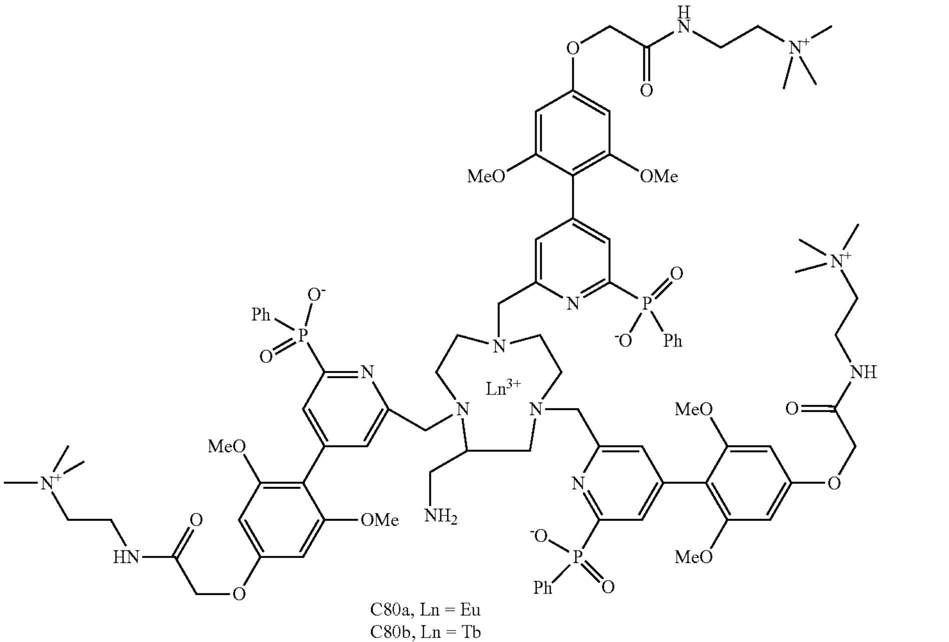
C80a, Ln = Eu
C80b, Ln = Tb -continued
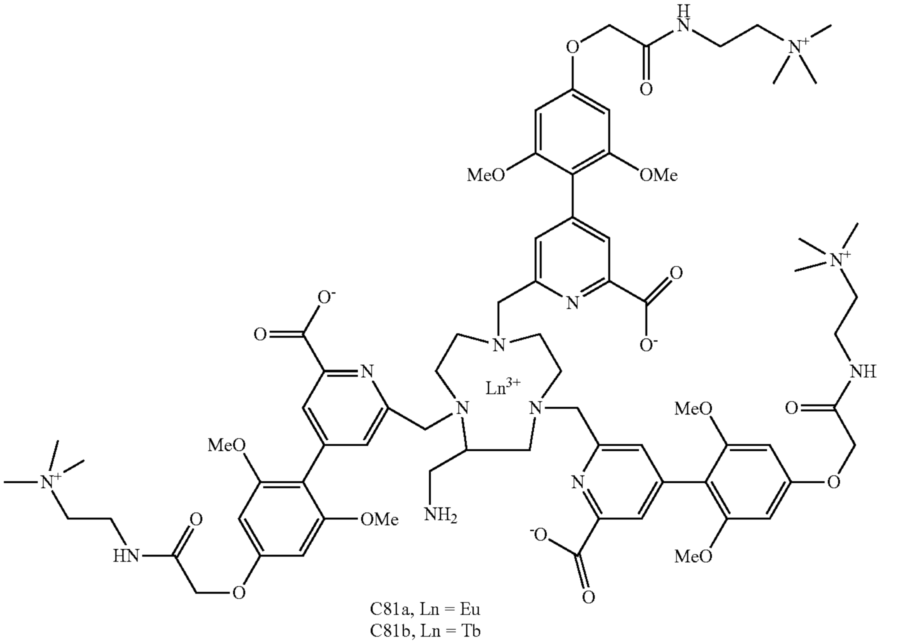
C81a, Ln = Eu
C81b, Ln = Tb
C82
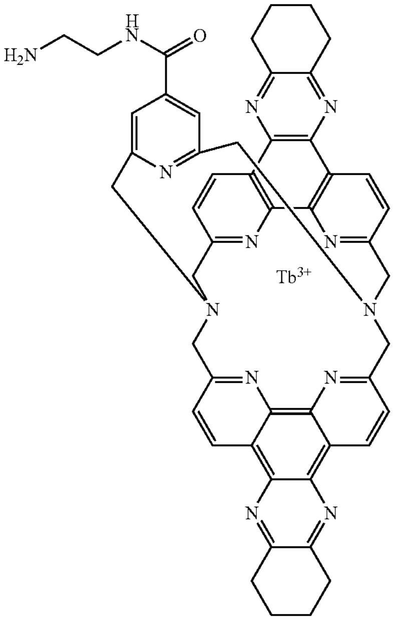
C83
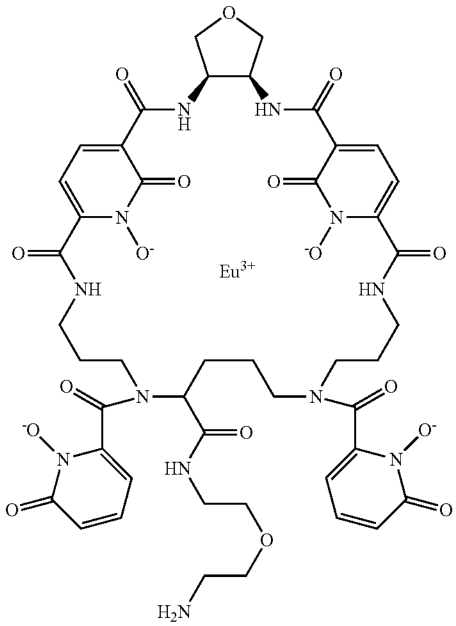

-continued
C84
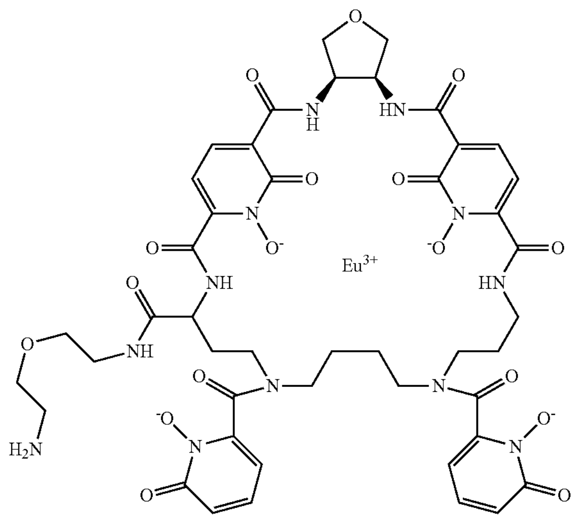
C85
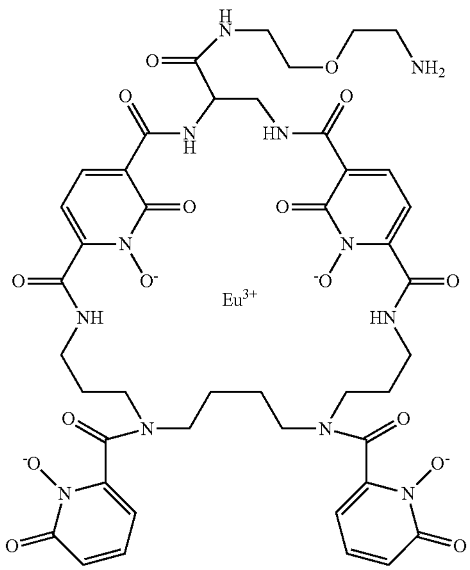
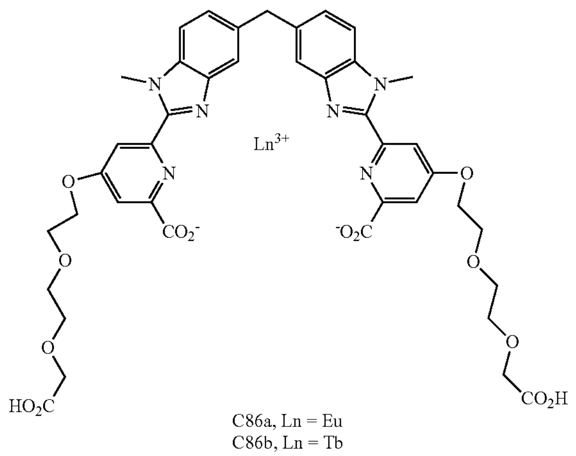
C86a, Ln = Eu
C86b, Ln = Tb
C87
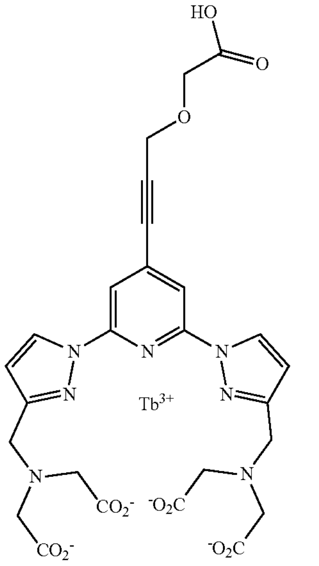
C88
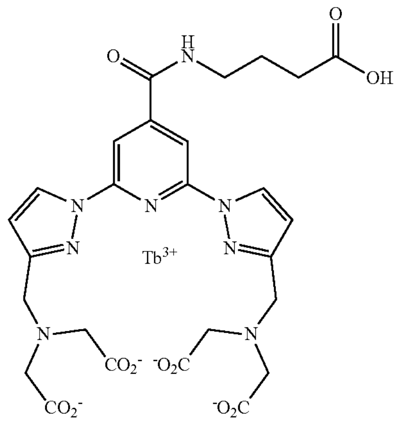
C89
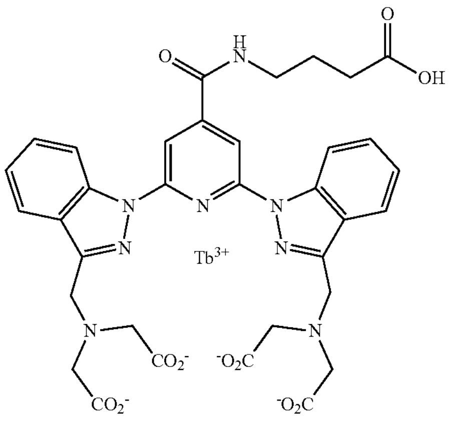

-continued

C90

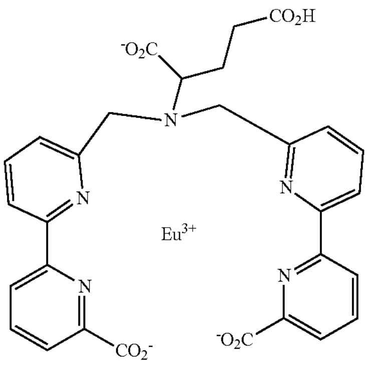

Advantageously, the lanthanide complex $Ln^{3+}$ is selected from one of the complexes C1 to C17, C24 to C32 and C36 to C44. More advantageously, the lanthanide complex $Ln^{3+}$ is selected from one of the complexes C1 to C17 and C36 to C44. Even more advantageously, the lanthanide complex $Ln^{3+}$ is selected from one of the complexes C1 to C17. Even more advantageously, the lanthanide complex $Ln^{3+}$ is selected from one of the complexes C1 to C4 and C11 to C17. Even more advantageously, the lanthanide complex $Ln^{3+}$ is selected from one of the complexes C1 to C4 and C11. Quite advantageously, the lanthanide complex $Ln^{3+}$ is the complex C2 or the complex C3.

Preparation of the aforementioned GTP analogues is described either in the literature, or in the French patent application filed on 30 Jan. 2019 under the number FR 19 00856.

Advantageously, the GTP analogue labeled with a fluorescent donor compound may be selected from GTPgN-C2 (GTP-gamma-N—C2), GTPgN-C3 (GTP-gamma-N—C3), GTPgN-octyl-C2 (GTP-gamma-N-octyl-C2), GTPgN-octyl-C11 (GTP-gamma-N-octyl-C11), GTPgN-octyl-C3 (GTP-gamma-N-octyl-C3), GTPgO-hexyl-C2 (GTP-gamma-O-hexyl-C2), GTPgO-hexyl-C3 (GTP-gamma-O-hexyl-C3) or GTP-gN-octyl-thiosuccinimidyl-C2 (GTP-gamma-N-octyl-thiosuccinimidyl-C2), presented below.

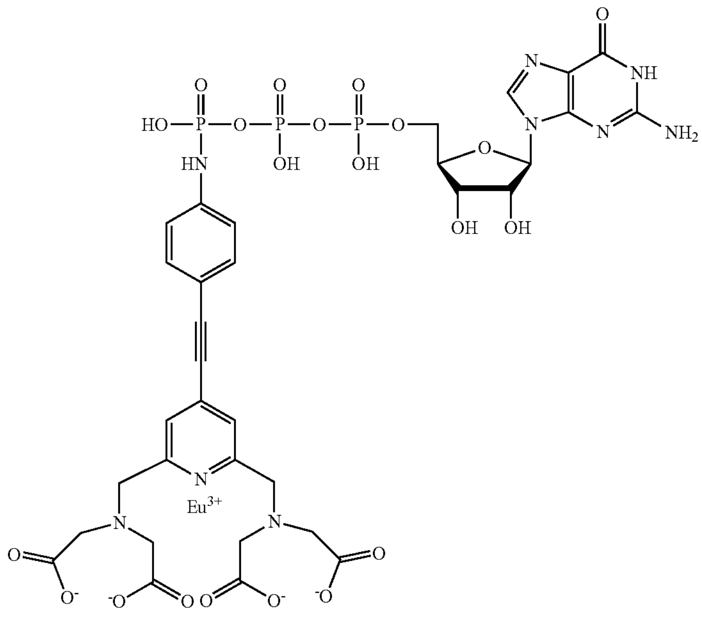

GTP-gamma-N-C2

-continued
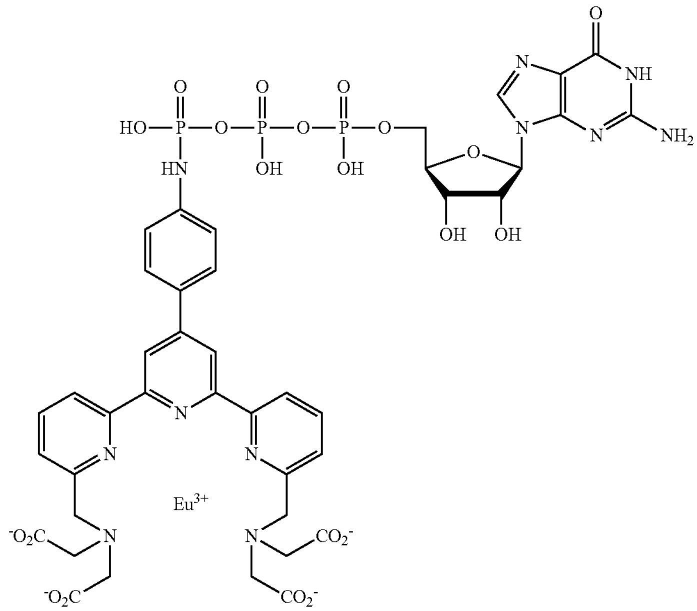
GTP-gamma-N-C3
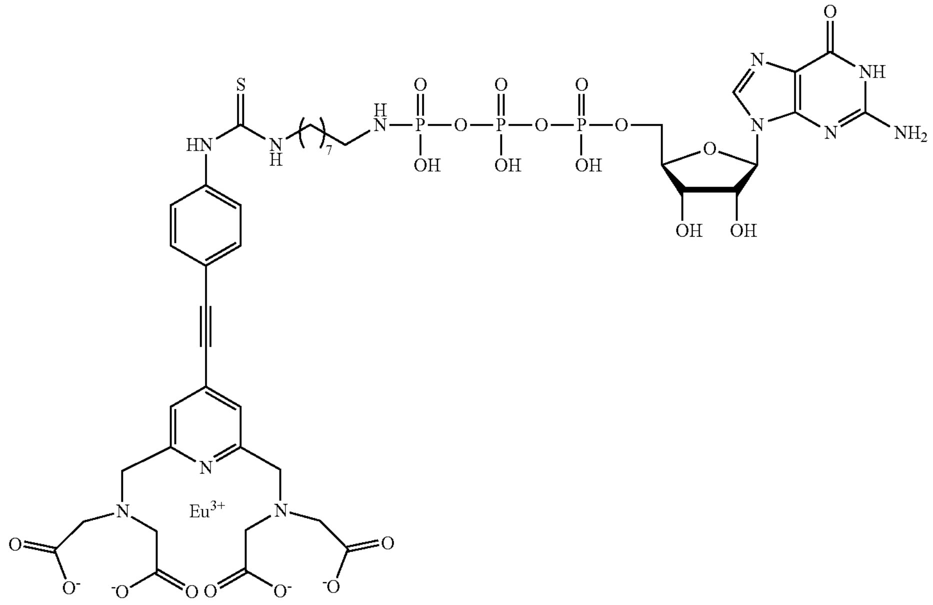
GTP-gamma-N octyl-C2

-continued
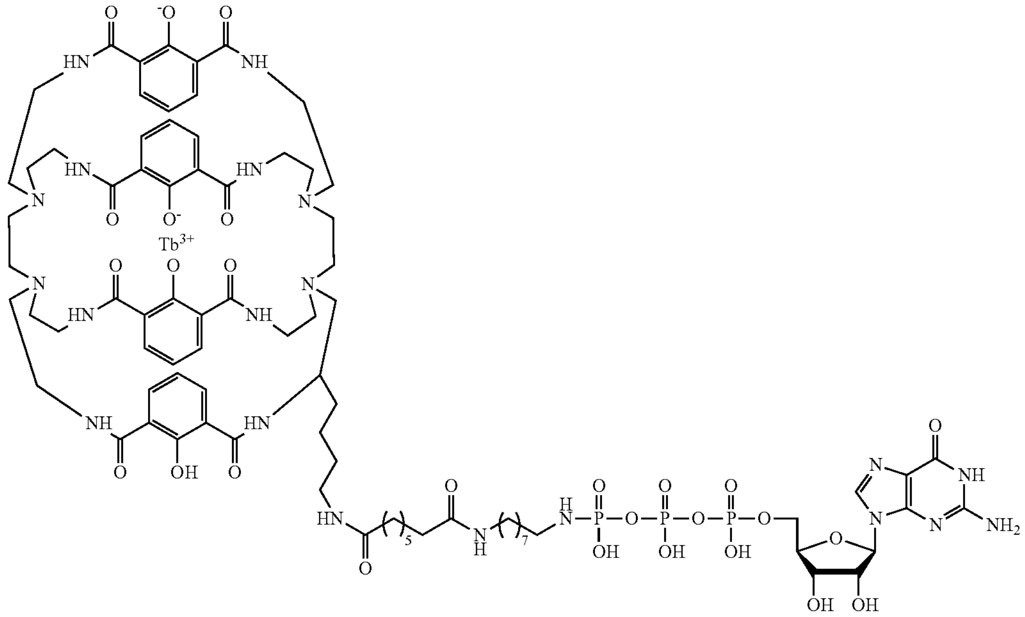
GTP-gamma-N oxtyl-C11
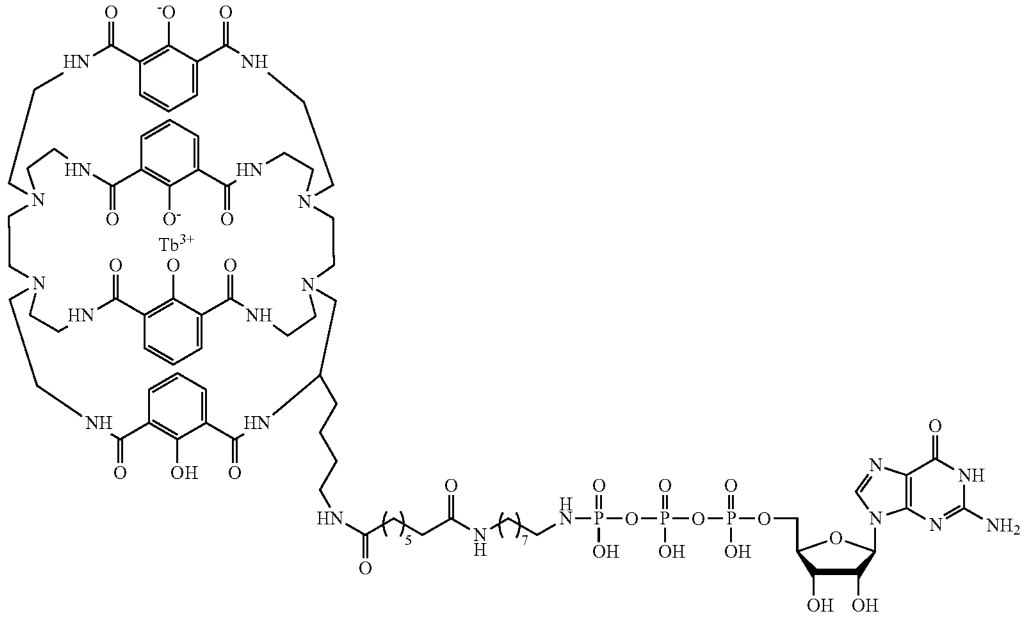
GTP-gamma-N oxtyl-C11

-continued
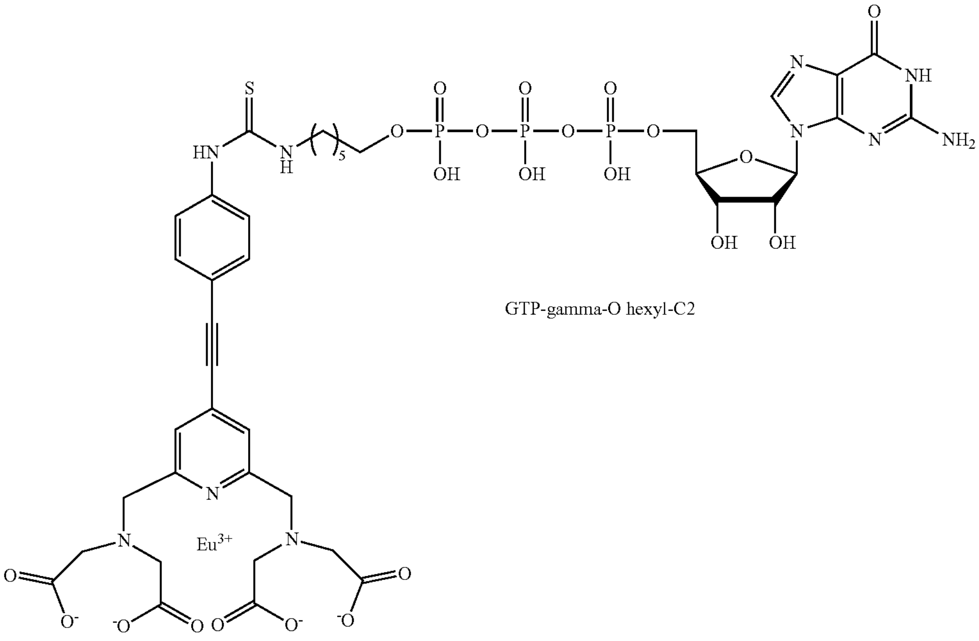
GTP-gamma-O hexyl-C2
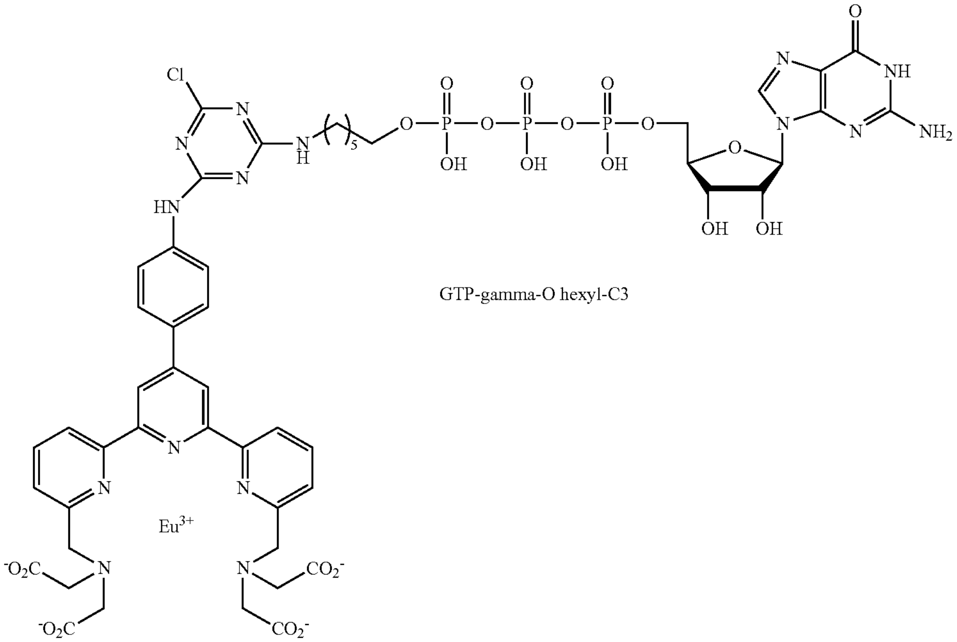
GTP-gamma-O hexyl-C3

In a particularly preferred embodiment, the GTP analogue labeled with a fluorescent donor compound is GTP-gN-octyl-thiosuccinimidyl-C2.

Fluorescent Acceptor Compounds

The fluorescent acceptor compounds may be selected from the following group: allophycocyanins, in particular those known by the trade name XL665; luminescent organic molecules, such as rhodamines, cyanins (for example such as Cy5), squaraines, coumarins, proflavins, acridines, fluoresceins, derivatives of boron-dipyrromethene (marketed under the name “BODIPY®”), fluorophors known by the name “ATTO™”, fluorophors known by the name “DY”, the compounds known by the name “Alexa Fluor®”, nitrobenzoxadiazole. Advantageously, the fluorescent acceptor compounds are selected from allophycocyanins, rhodamines, cyanins, squaraines, coumarins, proflavins, acridines, fluoresceins, derivatives of boron-dipyrromethene, nitrobenzoxadiazole.

The expressions “cyanins” and “rhodamines” are to be understood respectively as “cyanin derivatives” and “rhodamine derivatives”. A person skilled in the art is familiar with these various commercially available fluorophors.

The “Alexa Fluor®” compounds are marketed by the company Invitrogen; the “ATTO™” compounds are marketed by the company Attotec; the “DY” compounds are marketed by the company Dyomics; the “Cy” compounds are marketed by the company Amersham Biosciences; the other compounds are marketed by various suppliers of chemical reagents, such as the companies Sigma, Aldrich or Acros.

The following fluorescent proteins may also be used as the fluorescent acceptor compound: the cyan fluorescent proteins (AmCyan1, Midori-Ishi Cyan, mTFP1), the green fluorescent proteins (EGFP, AcGFP, TurboGFP, Emerald, Azami Green, ZsGreen), the yellow fluorescent proteins (EYFP, Topaz, Venus, mCitrine, YPet, PhiYFP, ZsYellow1, mBanana), the orange and red fluorescent proteins (Orange kusibari, mOrange, tdtomato, DsRed, DsRed2, DsRed-Express, DsRed-Monomer, mTangerine, AsRed2, mRFP1, JRed, mCherry, mStrawberry, HcRed1, mRaspberry, HcRed-Tandem, mPlim, AQ143), the fluorescent proteins in the far red (mKate, mKate2, tdKatushka2).

Advantageously, for the ligand of the alpha G-protein, the fluorescent acceptor compound is a FRET partner selected from: allophycocyanins, rhodamines, cyanins, squaraines, coumarins, proflavins, acridines, fluoresceins, derivatives of boron-dipyrromethene, nitrobenzoxadiazole and a quantum dot, GFP, the GFP variants selected from GFP10, GFP2 and eGFP, YFP, the YFP variants selected from eYFP, YFP topaz, YFP citrine, YFP venus and YPet, mOrange, DsRed.

Advantageously, for the labeled GTP analogue, the fluorescent acceptor compound is a FRET partner selected from: rhodamines, cyanins, squaraines, coumarins, proflavins, acridines, fluoresceins, derivatives of boron-dipyrromethene and nitrobenzoxadiazole.

Nonhydrolyzable or slowly hydrolyzable GTPs labeled with a fluorescent acceptor compound that may be used in the FRET method of the invention are represented by the following general formulas (3) and (4a, 4b, 4c):

3

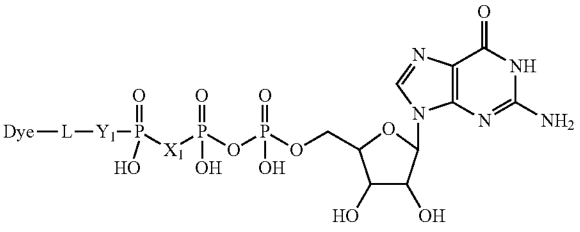

$Y_1$ = O, NH, $CH_2$
$X_1$ = O, NH, $CH_2$
L = linker divalent 4a-c

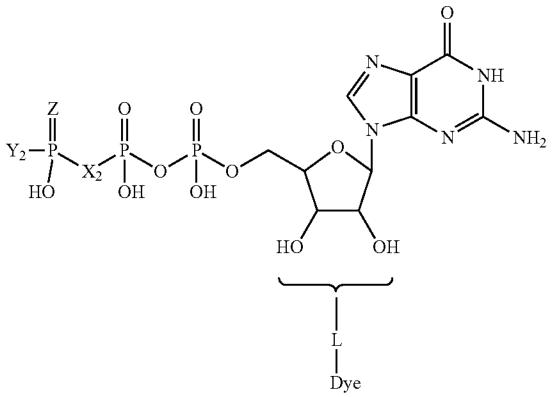

4a, Z = S, $Y_2$ = OH, $X_2$ = O;
4b, Z = O, $Y_2$ = OH, $X_2$ = NH
4c, Z = O, $Y_2$ = OH, $X_2$ = $CH_2$
L = linker divalent The labeling of the GTP analogues may be carried out at different positions of the GTP:

in a gamma position of the phosphate (O, NH, $CH_2$); or at positions 2' and 3' of the ribose.

In a particular embodiment, nonhydrolyzable or slowly hydrolyzable GTPs labeled with a fluorescent acceptor compound that may be used in the method of the invention may be selected from GTPgO-Linker-Cy5(P) (GTP-gO-hexyl-Cy5 diSO3-) (Jena Bioscience—NU-834-CY5), GTPgS-Linker-Cy5(R) (GTP-gS-EDA-Cy5) (Jena Bioscience—NU-1610-CY5), GTPgN-octyl-AF488 (GTP-gN-octyl-AF488) (Cisbio Bioassays), GTPgN-L18-Fluorescein (GTP-gN-EDA-pentyl-Fluorescein) (Cisbio Bioassays) and GTPgN-octyl-CY5 (GTP-gN-octyl-Cy5) (Cisbio Bioassays) and are represented by the following formulas:

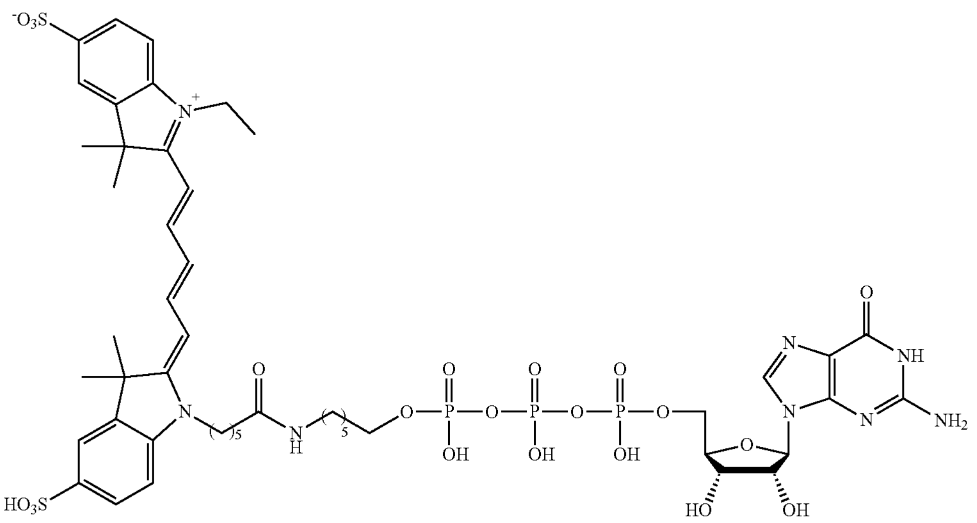
GTP-gO-hexyl-Cy5 diSO3⁻
(Jena Bioscience-NU-834-Cy5)
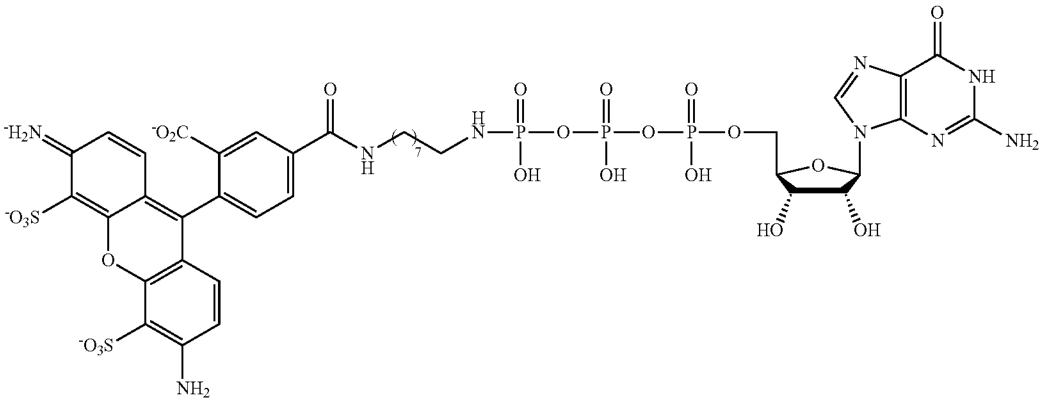
GTP-gN-octyl-AF488
(Cisbio Bioassays)
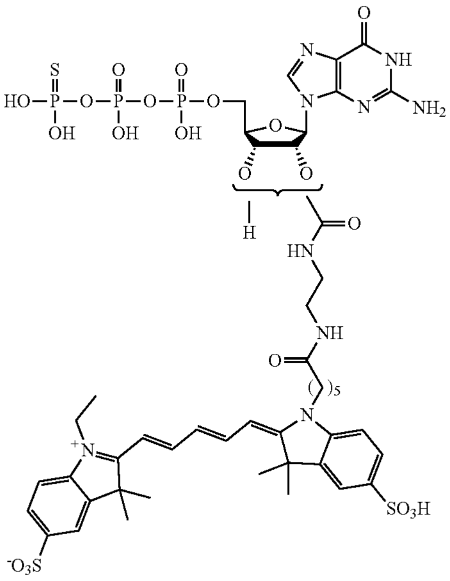
GTP-gS-EDA-Cy5
(Jena Bioscience-NU-1610-Cy5)

-continued

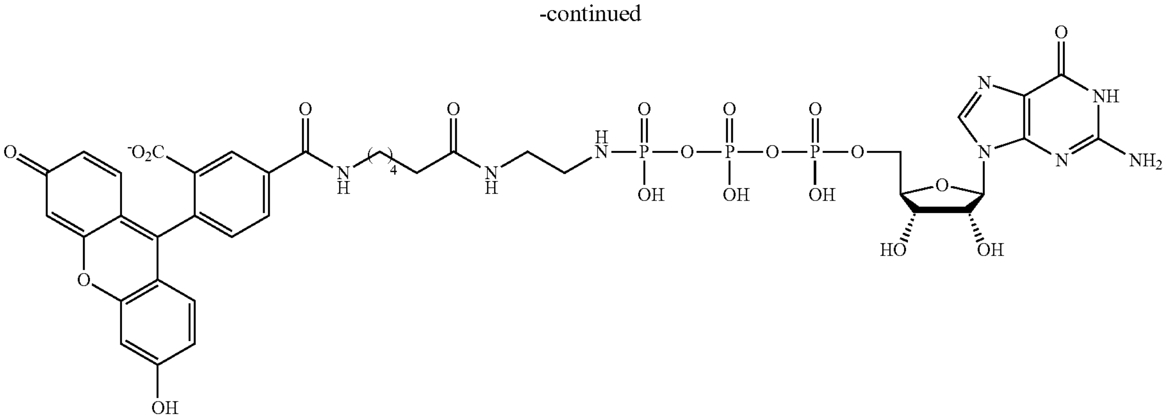

GTP-gN-EDA-pentyl-Fluoresceine
(Cisbio Bioassays)

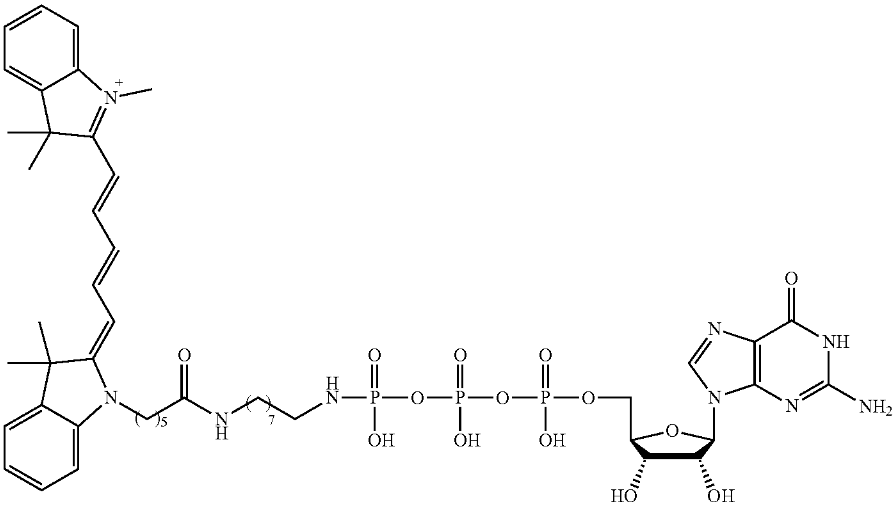

GTP-gN-octyl-Cy5
(Cisbio Bioassays)

Labeling for Carrying Out a BRET

In a particular embodiment, the ligand is labeled with a member of a pair of BRET partners, i.e. an energy-donating luminescent compound or an energy-accepting fluorescent compound.

The direct labeling of the ligand with a luminescent donor compound or a fluorescent acceptor compound of the protein type, a member of a pair of BRET partners, may be carried out by the conventional methods known by a person skilled in the art and in particular described in the article by Tarik Issad and Ralf Jockers (Bioluminescence Resonance Energy Transfer to Monitor Protein-Protein Interactions, Transmembrane Signaling Protocols pp 195-209, Part of the Methods in Molecular Biology™ book series MIMB, volume 332) to which a person skilled in the art may refer.

The direct labeling of the ligand or of the nonhydrolyzable or slowly hydrolyzable GTP with a fluorescent acceptor compound of the organic molecule type, a member of a pair of BRET partners, may be carried out by the conventional methods known by a person skilled in the art, based on the presence of reactive groups on the ligand as mentioned above.

The reactive groups may form a covalent bond with a reactive group borne by a member of a pair of BRET partners. The suitable reactive groups, borne by the member of a pair of BRET partners, are familiar to a person skilled in the art, for example an acceptor compound functionalized with a maleimide group will be for example capable of bonding covalently to the thiol groups borne by the cysteines borne by a protein or a peptide, for example an antibody or an antibody fragment. Similarly, an acceptor compound bearing an N-hydroxysuccinimide ester will be capable of binding covalently to an amine present in a protein or a peptide.

Selection of the pair of BRET partners for obtaining a BRET signal is within the capability of a person skilled in the art. For example, donor-acceptor pairs usable for studying the BRET phenomena are described in particular in the article by Dasiel O. Borroto-Escuela (BIOLUMINESCENCE RESONANCE ENERGY TRANSFER (BRET) METHODS TO STUDY G PROTEIN-COUPLED RECEPTOR-RECEPTOR TYROSINE KINASE HETERORECEPTOR COMPLEXES, Methods Cell Biol. 2013; 117: 141-164), to which a person skilled in the art may refer.

Luminescent Donor Compounds

In a particular embodiment, the luminescent donor compound is a BRET partner selected from: Luciferase (luc), Renilla Luciferase (Rluc), the variants of Renilla Luciferase (Rluc8) and Firefly Luciferase.

Fluorescent Acceptor Compounds

In a particular embodiment, the fluorescent acceptor compound is a BRET partner selected from: allophycocyanins, rhodamines, cyanins, squaraines, coumarins, proflavins, acridines, fluoresceins, derivatives of boron-dipyrromethene, nitrobenzoxadiazole, a quantum dot, GFP, GFP variants (GFP10, GFP2, eGFP), YFP, YFP variants (eYFP, YFP topaz, YFP citrine, YFP venus, YPet), mOrange, DsRed.

EXAMPLES

Materials

- the cell membrane preparations expressing the receptors under investigation and the alphai G-protein were purchased from Perkin Elmer or Euroscreen. The following table lists the base cells and references of the various samples used:

TABLE 1

| | Base cell | Supplier | Reference |
|---|---|---|---|
| Delta Opioid | HEK293 | Perkin Elmer | 6110549400UA |
| Delta Opioid | CHO-K1 | Euroscreen | Service |
| Dopamine D2S | CHO-K1 | Euroscreen | Service |

- the DSV36S and DSV38S antibodies were generated by Cisbio Bioassays and are available from Cisbio Bioassays on request (under the respective references DSV36S and DSV38S). The DSV36S antibody comprises a variable domain of the heavy chain that consists of the amino acid sequence SEQ ID NO: 14 and a variable domain of the light chain that consists of the amino acid sequence SEQ ID NO: 15. The antibodies were labeled with the fluorescent probes compatible for TR-FRET detection (acceptor red—d2 or donor Lumi4Tb). The two antibodies DSV36S and DSV38S bind at the level of the switch II domain of the alphai G-protein.
- the nucleotides GTP, GDP and GTPγS were purchased from Sigma Aldrich (respective catalog references G8877, G7127 and G8634).
- the GPCR agonists Delta Opioid (SNC162) and Dopamine D2S (PPHT) and the GPCR antagonist Delta Opioid (Naltrindole) were purchased from Tocris (respective catalog references 1529 and 0740).
- the Low volume 384-well plates, white with white base were purchased from Greiner Bio One (Catalog reference 784075).
- The nonhydrolyzable/slowly hydrolyzable GTP analogues labeled with donor or acceptor fluorophors (GTPgN-C2; GTPgN-C3; GTPgN-octyl-C2; GTPgN-octyl-C11, GTPgN-octyl-C3; GTPgO-hexyl-C2; GTPgO-hexyl-C3; GTP-gN-octyl-thiosuccinimidyl-C2, GTPgN-octyl-Cy5; GTPgN-octyl-AF488) were synthesized at Cisbio Bioassays.
- The nonhydrolyzable/slowly hydrolyzable GTP analogues labeled with acceptor fluorophors GTPgO-Linker-Cy5(P) and GTPgS-Linker-Cy5(R) were purchased from Jena Bioscience under the respective references NU-834-CY5 and NU-1610-CY5.

Method

Preparation of the Reagents

All the reagents were diluted in TrisHCl buffer 50 mM pH 7.4, MgCl2 10 mM, BSA 0.1%, NaCl 10 mM or 100 mM or 300 mM or 500 mM (concentration specified in the legend of each figure), 0 or 0.5 or 1 μM GDP (concentration specified in the legend of each figure). The membranes were prepared 4× for distributing 1 or 10 μg/well (amount specified in the legend of each figure). The nucleotide GTPgS (nonspecific signal condition) was prepared 6.67× to obtain a final concentration in the wells of 100 μM. The test compounds (agonists or antagonists) were prepared 10× to obtain the final concentrations in the wells mentioned in the diagrams. The anti-G-alphai antibodies used for detection were prepared 4× for the following final concentrations in the wells: DSV36S-d2 antibody (10 nM), DSV36S-Lumi4Tb antibody (0.5 or 1 nM), DSV38S-d2 antibody (10 nM). The nonhydrolyzable/slowly hydrolyzable GTP analogues labeled with donor or acceptor fluorescent probes were prepared 4× for the final concentrations in the wells mentioned in the legends of each figure.

Distribution of the Reagents in the 384-Well Plates

- Membranes expressing the GPCR and the G protein: 5 μL
- Buffer or GTPgS nucleotide (for the nonspecific signal condition): 3 μL
- Nonhydrolyzable/slowly hydrolyzable GTP analogue—donor or acceptor: 5 μL
- anti G-alphai-donor or acceptor ligand: 5 μL
- Buffer or test compounds (agonists and/or antagonists): 2 μL.

The nonspecific signal (fluorescence background noise) was measured with wells containing an excess of GTPgS (100 μM).

Reading the HTRF Signal

The plates were incubated at 21° C. for 20 h (unless otherwise specified in the figures) and then the HTRF signal was measured on the PHERAstar reader (BMG Labtech) with the following configuration:

- Module: HTRF (Excitation 337 nm, Emission 665 nm and 620 nm)
- Excitation: laser, 40 flashes or lamp, 100 flashes
- Reading window: time: 60 μs—Integration: 400 μs.

Signal Processing

From the raw signals at 665 nm (for red acceptor—Cy5) or 520 nm (for green acceptors—AF488 or Fluorescein) and 620 nm, the HTRF Ratio was calculated from the following formula: HTRF Ratio=Signal at 665 nm or Signal at 520 nm/Signal at 620 nm*10.000.

Test Formats

FIG. 2A illustrates the test principle using a nonhydrolyzable/slowly hydrolyzable GTP analogue labeled with a RET donor partner and an anti G protein ligand labeled with a RET acceptor partner in which activation of the GPCR with an agonist compound induces a decrease in binding of the donor GTP analogue to the G protein and therefore a decrease in the RET signal (format 1A).

FIG. 2B illustrates the test principle using a nonhydrolyzable/slowly hydrolyzable GTP analogue labeled with a RET acceptor partner and an anti G protein ligand labeled with a RET donor partner in which activation of the GPCR with an agonist compound induces a decrease in binding of the acceptor GTP analogue to the G protein and therefore a decrease in the RET signal (format 1B).

FIG. 2C illustrates the test principle using a nonhydrolyzable/slowly hydrolyzable GTP analogue labeled with a RET donor partner and an anti G protein ligand labeled with a RET acceptor partner in which activation of the GPCR with an agonist compound induces an increase in binding of the donor GTP analogue to the G protein and therefore an increase in the RET signal (format 2A).

FIG. 2D illustrates the test principle using a nonhydrolyzable/slowly hydrolyzable GTP analogue labeled with a RET acceptor partner and an anti G protein ligand labeled with a RET donor partner in which activation of the GPCR with an agonist compound induces an increase in binding of the acceptor GTP analogue to the G protein and therefore an increase in the RET signal (format 2B).

Examples 1 to 7—Activation Test According to Format 1A on Delta Opioid GPCR (DOR): Decrease in the TR-FRET Signal Between GTP-Donor and G-Alphai Protein Acceptor Antibody Under Stimulation of an Agonist Firstly, the capacity of the GTP-donor/anti-G-alphai acceptor antibody pairs for generating a specific TR-FRET signal on binding to the G protein was detected using HEK293 or CHO-K1 cell membrane preparations expressing the Delta Opioid GPCR and the Galphai protein. The following experimental conditions were used:

- Example 1/FIG. 3A: GTPgN-octyl-C2 (6 nM final in the well); DSV36S-d2 (10 nM final in the well); 10 µg CHO-DOR membranes/well; Buffer: TrisHCl 50 mM pH7.4; MgCl2 10 mM; NaCl 10 mM; BSA 0.1%.
- Example 2/FIG. 4A: GTPgN-octyl-C11 (6 nM final in the well); DSV36S-d2 (10 nM final in the well); 10 µg CHO-DOR membranes/well; Buffer: TrisHCl 50 mM pH7.4; MgCl2 10 mM; NaCl 10 mM; BSA 0.1%.
- Example 3/FIG. 5A: GTPgO-hexyl-C2 (6 nM final in the well); DSV36S-d2 (10 nM final in the well); 10 µg CHO-DOR membranes/well; Buffer: TrisHCl 50 mM pH7.4; MgCl2 10 mM; NaCl 10 mM; BSA 0.1%.
- Example 4/FIG. 6A: GTPgN-C2 (6 nM final in the well); DSV36S-d2 (10 nM final in the well); 10 µg CHO-DOR membranes/well; Buffer: TrisHCl 50 mM pH7.4; MgCl2 10 mM; NaCl 10 mM; BSA 0.1%.
- Example 5/FIG. 7A: GTPgN-C3 (6 nM final in the well); DSV36S-d2 (10 nM final in the well); 1 µg HEK-DOR membranes/well; Buffer: TrisHCl 50 mM pH7.4; MgCl2 10 mM, NaCl 10 mM, BSA 0.1%.
- Example 6/FIG. 8: GTPgN-octyl-C3 (6 nM final in the well); DSV36S-d2 (10 nM final in the well); 1 µg HEK-DOR membranes/well; Buffer: TrisHCl 50 mM pH7.4; MgCl2 10 mM; NaCl 10 mM; BSA 0.1%.
- Example 7/FIG. 9: GTPgO-hexyl-C3 (6 nM final in the well); DSV36S-d2 (10 nM final in the well); 1 µg HEK-DOR membranes/well; Buffer: TrisHCl 50 mM pH7.4; MgCl2 10 mM; NaCl 10 mM; BSA 0.1%.

The membranes were incubated in the absence or in the presence of a large excess of GTPgS (100 µM). The TR-FRET signal difference (HTRF Ratio) observed between these two conditions shows that the analogues GTPgN-octyl-C2, GTPgN-octyl-C11, GTPgO-hexyl-C2, GTPgN-C2, GTPgN-C3, GTPgN-octyl-C3, GTPgO-hexyl-C3 are capable of binding to the alphai G-protein and generating a TR-FRET signal with the anti G-alphai-acceptor antibody (FIG. 3A to 9).

Secondly, the capacity of a GPCR agonist for modulating the proportion of alpha G-protein bound to the GTP-donor was tested with the same membranes and experimental conditions mentioned above. The decrease in the TR-FRET signal (HTRF Ratio) generated by stimulation with the agonist signifies that the proportion of alpha G-protein form bound to the GTP-donor decreases (i.e. the empty alpha G-protein form increases). Thus, the GPCR receptor activated by its agonist leads to the GTP-donor leaving the G protein, which then changes to the empty form and leads to a decrease in the TR-FRET signal. These results are presented in FIGS. 3B (Example 1), 4B (Example 2), 5B (Example 3), 6B (Example 4) and 7B (Example 5). This modulation of the signal by an agonist was not tested with the analogues GTPgN-octyl-C3 (Example 6) and GTPgO-hexyl-C3 (Example 7).

Example 8—Effect of the Concentration of Membrane and of GTP-Donor on the Activation Test According to Format 1A on Delta Opioid GPCR (DOR): Decrease in the TR-FRET Signal Between GTP-Donor and G-Alphai Protein Acceptor Antibody Under Stimulation of an Agonist Firstly, the capacity of the GTPgN-octyl-C2/anti-G-alphai DSV36S-d2 antibody pair for generating a specific TR-FRET signal on binding to the G protein was detected using CHO-K1 cell membrane preparations expressing the Delta Opioid GPCR and the Galphai protein (1 or 10 µg/well). GTPgN-octyl-C2 was used at 2 or 6 nM final in the wells. The membranes were incubated in the absence or in the presence of a large excess of GTPgS (100 µM). The TR-FRET signal difference (HTRF Ratio) observed between these two conditions shows that the GTPgN-octyl-C2 analogue is capable of binding to the alphai G-protein and generating a TR-FRET signal with the anti G-alphai DSV36S-d2 antibody (FIG. 10A). Moreover, the panel on the left shows an increase in the signal amplitude (S/B=Total Signal/Nonspecific Signal) on increasing the amount of membrane from 1 to 10 µg per well. The panel on the right shows an increase in the amplitude of the signal (S/B) on increasing the concentration of GTPgN-octyl-C2 from 2 to 6 nM.

Secondly, the capacity of a GPCR agonist for modulating the proportion of alpha G-protein bound to the GTP-donor was tested with the same membranes and experimental conditions mentioned above. The decrease in the TR-FRET signal (HTRF Ratio) generated by stimulation with the agonist signifies that the proportion of the alpha G-protein form bound to the GTP-donor decreases (i.e. the empty alpha G-protein form increases). Thus, the GPCR receptor activated by its agonist leads to the GTP-donor leaving the G protein, which then changes to the empty form and leads to a decrease in the TR-FRET signal. These results are shown in FIG. 10B. Moreover, the panel on the left shows an increase in the signal amplitude (S/B=Signal of Vehicle without agonist/Agonist Signal) on increasing the amount of membrane from 1 to 10 µg per well. The panel on the right shows an increase in the amplitude of the signal (S/B) on increasing the concentration of GTPgN-octyl-C2 from 2 to 6 nM.

Examples 9 and 10—Activation Test According to Format 1A on GPCR Dopamine D2S (D2S): Decrease in the TR-FRET Signal Between GTP-Donor and G-Alphai Protein Acceptor Antibody Under Stimulation of an Agonist Firstly, the capacity of the GTP-donor/anti-G-alphai acceptor antibody pairs for generating a specific TR-FRET signal on binding to the G protein was detected using CHO-K1 cell membrane preparations expressing the GPCR Dopamine D2S and the alphai G-protein. The following experimental conditions were used:

Example 9/FIG. 11A: GTPgN-octyl-C2 (6 nM final in the well); DSV36S-d2 (10 nM final in the well); 10 µg CHO-D2S membranes/well; Buffer: TrisHCl 50 mM pH7.4; MgCl2 10 mM; NaCl 10 mM; BSA 0.1%.

Example 10/FIG. 12A: GTPgN-octyl-C11 (6 nM final in the well); DSV36S-d2 (10 nM final in the well); 10 µg CHO-D2S membranes/well; Buffer: TrisHCl 50 mM pH7.4; MgCl2 10 mM; NaCl 10 mM; BSA 0.1%.

The membranes were incubated in the absence or in the presence of a large excess of GTPgS (100 µM). The TR-FRET signal difference (HTRF Ratio) observed between these two conditions shows that the analogues GTPgN-octyl-C2 and GTPgN-octyl-C11 are capable of binding to the alphai G-protein and generating a TR-FRET signal with the anti G-alphai-acceptor antibody (FIG. 11A to 12A).

Secondly, the capacity of a GPCR agonist for modulating the proportion of alpha G-protein bound to the GTP-donor was tested with the same membranes and experimental conditions mentioned above. The decrease in the TR-FRET signal (HTRF Ratio) generated by stimulation with the agonist signifies that the proportion of alpha G-protein form bound to the GTP-donor decreases (i.e. the empty alpha G-protein form increases). Thus, the GPCR receptor activated by its agonist leads to the GTP-donor leaving the G protein, which then changes to the empty form and leads to a decrease in the TR-FRET signal. These results are presented in FIGS. 11B (Example 9) and 12B (Example 10).

Examples 11 to 13—Activation Test According to Format 1B on Delta Opioid GPCR (DOR): Decrease in the TR-FRET Signal Between GTP-Acceptor and Anti G-Alphai Protein Donor Antibody Under Stimulation of an Agonist Firstly, the capacity of the GTP-acceptor/anti-G-alphai donor antibody pairs for generating a specific TR-FRET signal on binding to the G protein was detected using HEK293 cell membrane preparations expressing the Delta Opioid GPCR and the Galphai protein. The following experimental conditions were used:

Example 11/FIG. 13A: GTPgO-Linker-Cy5(P) (250 nM final in the well); DSV36S-Lumi4Tb (0.25 nM final in the well); 1 µg HEK-DOR membranes/well; Buffer: TrisHCl 50 mM pH7.4; MgCl2 10 mM; NaCl 10 mM; BSA 0.1%. Reading after incubation for 3 h at 21° C.

Example 12/FIG. 14A: GTPgS-Linker-Cy5(R) (250 nM final in the well); DSV36S-Lumi4Tb (0.25 nM final in the well); 10 µg HEK-DOR membranes/well; Buffer: TrisHCl 50 mM pH7.4; MgCl2 10 mM; NaCl 10 mM; BSA 0.1%. Reading after incubation for 1 h at 21° C.

Example 13/FIG. 15A: GTPgN-L18-Fluorescein (31 nM final in the well); DSV36S-Lumi4Tb (0.25 nM final in the well); 1 µg HEK-DOR membranes/well; Buffer: TrisHCl 50 mM pH7.4; MgCl2 10 mM; NaCl 10 mM; BSA 0.1%.

The membranes were incubated in the absence or in the presence of a large excess of GTPgS (100 µM). The TR-FRET signal difference (HTRF Ratio) observed between these two conditions shows that the analogues GTPgO-Linker-Cy5(P), GTPgS-Linker-Cy5(R) and GTPgN-L18-Fluorescein are capable of binding to the alphai G-protein and generating a TR-FRET signal with the anti G-alphai-donor antibody (FIG. 13A to 15A).

Secondly, the capacity of a GPCR agonist for modulating the proportion of alpha G-protein bound to the GTP-acceptor was tested with the same membranes and experimental conditions mentioned above. The decrease in the TR-FRET signal (HTRF Ratio) generated by stimulation with the agonist signifies that the proportion of alpha G-protein form bound to the GTP-acceptor decreases (i.e. the empty alpha G-protein form increases). Thus, the GPCR receptor activated by its agonist leads to the GTP-acceptor leaving the G protein, which then changes to the empty form and leads to a decrease in the TR-FRET signal. These results are presented in FIGS. 13B (Example 11), 14B (Example 12), 15B (Example 13). This modulation of the signal by an agonist is very slight with the analogue GTPgS-Linker-Cy5(R) (Example 12).

Examples 14 to 19—Activation Test According to Format 2A on Delta Opioid GPCR (DOR): Increase in the TR-FRET Signal Between GTP-Donor and G-Alphai Protein Acceptor Antibody Under Stimulation of an Agonist Firstly, the capacity of the GTP-donor/anti-G-alphai acceptor antibody pairs for generating a specific TR-FRET signal on binding to the G protein was detected using CHO-K1 cell membrane preparations expressing the Delta Opioid GPCR and the Galphai protein. The following experimental conditions were used:

Example 14/FIG. 16A: GTPgN-octyl-C2 (6 nM final in the well); DSV36S-d2 (10 nM final in the well); 10 µg CHO-DOR membranes/well; Buffer: TrisHCl 50 mM pH7.4; MgCl2 10 mM; NaCl 500 mM; BSA 0.1%.

Example 15/FIG. 17A: GTPgN-octyl-C2 (6 nM final in the well); DSV36S-d2 (10 nM final in the well); 10 µg CHO-DOR membranes/well; Buffer: TrisHCl 50 mM pH7.4; MgCl2 10 mM; NaCl 300 mM; GDP 0.5 µM; BSA 0.1%.

Example 16/FIG. 18A: GTPgN-octyl-C2 (6 nM final in the well); DSV38S-d2 (10 nM final in the well); 10 µg CHO-DOR membranes/well; Buffer: TrisHCl 50 mM pH7.4; MgCl2 10 mM; NaCl 300 mM; GDP 0.5 µM; BSA 0.1%.

Example 17/FIG. 19A: GTPgN-octyl-C11 (6 nM final in the well); DSV36S-d2 (10 nM final in the well); 10 µg CHO-DOR membranes/well; Buffer: TrisHCl 50 mM pH7.4; MgCl2 10 mM; NaCl 300 mM; GDP 0.5 µM, BSA 0.1%.

Example 18/FIG. 20A: GTPgO-hexyl-C2 (6 nM final in the well); DSV36S-d2 (10 nM final in the well); 10 µg CHO-DOR membranes/well; Buffer: TrisHCl 50 mM pH7.4; MgCl2 10 mM; NaCl 300 mM; GDP 0.5 µM, BSA 0.1%.

Example 19/FIG. 21A: GTPgN-C2 (6 nM final in the well); DSV36S-d2 (10 nM final in the well); 10 µg CHO-DOR membranes/well; Buffer: TrisHCl 50 mM pH7.4; MgCl2 10 mM; NaCl 300 mM; GDP 0.5 µM; BSA 0.1%.

The membranes were incubated in the absence or in the presence of a large excess of GTPgS (100 µM). The TR-FRET signal difference (HTRF Ratio) observed between these two conditions shows that the analogues GTPgN-octyl-C2, GTPgN-octyl-C11, GTPgO-hexyl-C2, GTPgN-C2 are capable of binding to the alphai G-protein and generating a TR-FRET signal with the anti G-alphai-acceptor antibody (FIGS. 16A to 21A).

Secondly, the capacity of a GPCR agonist for modulating the proportion of alpha G-protein bound to the GTP-donor was tested with the same membranes and experimental conditions mentioned above. The increase in the TR-FRET signal (HTRF Ratio) generated by stimulation with the agonist signifies that the proportion of alpha G-protein form bound to the GTP-donor increases (i.e. the empty alpha G-protein form decreases). Thus, the GPCR receptor activated by its agonist leads to binding of the GTP-donor to the G protein, which then changes to the GTP-donor form and leads to an increase in the TR-FRET signal. These results are presented in FIGS. 16B (Example 14), 17B (Example 15), 18B (Example 16), 19B (Example 17), 20B (Example 18) and 21B (Example 19). Moreover, FIG. 17B (Example 15) shows a second condition where activation by a fixed concentration of GPCR agonist SNC162 (200 nM) was inhibited by an increasing concentration of GPCR antagonist (Naltrindole). This inhibition of activation is observed from the decrease in the TR-FRET signal (HTRF Ratio).

Examples 20 to 22—Activation Test According to Format 2A on GPCR Dopamine D2S (D2S): Increase in the TR-FRET Signal Between GTP-Donor and G-Alphai Protein Acceptor Antibody Under Stimulation of an Agonist Firstly, the capacity of the GTP-donor/anti-G-alphai acceptor antibody pairs for generating a specific TR-FRET signal on binding to the G protein was detected using CHO-K1 cell membrane preparations expressing the GPCR Dopamine D2S and the alphai G-protein. The following experimental conditions were used:

Example 20/FIG. 22A: GTPgN-octyl-C2 (6 nM final in the well); DSV36S-d2 (10 nM final in the well); 10 μg CHO-D2S membranes/well; Buffer: TrisHCl 50 mM pH7.4; MgCl2 10 mM; NaCl 10 mM; GDP 1 μM, BSA 0.1%.

Example 21/FIG. 23A: GTPgN-octyl-C2 (6 nM final in the well); DSV36S-d2 (10 nM final in the well); 10 μg CHO-D2S membranes/well; Buffer: TrisHCl 50 mM pH7.4; MgCl2 10 mM; NaCl 100 mM; BSA 0.1%.

Example 22/FIG. 24A: GTPgN-octyl-C2 (6 nM final in the well); DSV36S-d2 (10 nM final in the well); 10 μg CHO-D2S membranes/well; Buffer: TrisHCl 50 mM pH7.4; MgCl2 10 mM; NaCl 100 mM; GDP 1 μM, BSA 0.1%.

The membranes were incubated in the absence or in the presence of a large excess of GTPgS (100 μM). The TR-FRET signal difference (HTRF Ratio) observed between these two conditions shows that the analogue GTPgN-octyl-C2 is capable of binding to the alphai G-protein and generating a TR-FRET signal with the anti G-alphai-acceptor antibody (FIG. 22A to 24A).

Secondly, the capacity of a GPCR agonist for modulating the proportion of alpha G-protein bound to the GTP-donor was tested with the same membranes and experimental conditions mentioned above. The increase in the TR-FRET signal (HTRF Ratio) generated by stimulation with the agonist signifies that the proportion of alpha G-protein form bound to the GTP-donor increases (i.e. the empty alpha G-protein form decreases). Thus, the GPCR receptor activated by its agonist leads to binding of the GTP-donor to the G protein, which then changes to the GTP-donor form and leads to an increase in the TR-FRET signal. These results are presented in FIGS. 22B (Example 20), 23B (Example 21) and 24B (Example 22).

Examples 23 and 24—Activation Test According to Format 2B on Delta Opioid GPCR (DOR): Increase in the TR-FRET Signal Between GTP-Acceptor and Anti G-Alphai Protein Donor Antibody Under Stimulation of an Agonist Firstly, the capacity of the GTP-acceptor/anti-G-alphai donor antibody pairs for generating a specific TR-FRET signal on binding to the G protein was detected using CHO-K1 cell membrane preparations expressing the Delta Opioid GPCR and the Galphai protein. The following experimental conditions were used:

Example 23/FIG. 25A: GTPgN-octyl-Cy5 (50 nM final in the well); DSV36S-Lumi4Tb (1 nM final in the well); 10 μg CHO-DOR membranes/well; Buffer: TrisHCl 50 mM pH7.4; MgCl2 10 mM; NaCl 300 mM; GDP 0.5 μM; BSA 0.1%. Reading after incubation for 3 h at 21° C.

Example 24/FIG. 26A: GTPgN-octyl-AF488 (50 nM final in the well); DSV36S-Lumi4Tb (1 nM final in the well); 10 μg CHO-DOR membranes/well; Buffer: TrisHCl 50 mM pH7.4; MgCl2 10 mM; NaCl 300 mM; GDP 0.5 μM; BSA 0.1%. Reading after incubation for 3 h at 21° C.

The membranes were incubated in the absence or in the presence of a large excess of GTPgS (100 μM). The TR-FRET signal difference (HTRF Ratio) observed between these two conditions shows that the analogues GTPgN-octyl-Cy5 and GTPgN-octyl-AF488 are capable of binding to the alphai G-protein and generating a TR-FRET signal with the anti G-alphai-donor antibody (FIG. 25A to 26A).

Secondly, the capacity of a GPCR agonist for modulating the proportion of alpha G-protein bound to the GTP-acceptor was tested with the same membranes and experimental conditions mentioned above. The increase in the TR-FRET signal (HTRF Ratio) generated by stimulation with the agonist signifies that the proportion of alpha G-protein form bound to the GTP-acceptor increases (i.e. the empty alpha G-protein form decreases). Thus, the GPCR receptor activated by its agonist leads to binding of the GTP-acceptor to the G protein, which then changes to the GTP-acceptor form and leads to an increase in the TR-FRET signal. These results are presented in FIGS. 25B (Example 23) and 26B (Example 24).

Example 25—Activation Test According to Format 2A on Delta Opioid GPCR (DOR): Increase in the TR-FRET Signal Between GTP-Donor and G-Alphai Protein Acceptor Antibody Under Stimulation of an Agonist Firstly, the capacity of the GTP-donor/anti-G-alphai acceptor antibody pairs for generating a specific TR-FRET signal on binding to the G protein was detected using CHO-K1 cell membrane preparations expressing the Delta Opioid GPCR and the Galphai protein. The following experimental conditions were used:

Example 25/FIG. 27A: GTP-gN-octyl-thiosuccinimidyl-C2 (7.5 nM final in the well); DSV36S-d2 (10 nM final in the well); 10 μg CHO-DOR membranes/well; Buffer: TrisHCl 50 mM pH7.4; MgCl2 60 mM; NaCl 150 mM; BSA 0.1%.

The membranes were incubated in the absence or in the presence of a large excess of GTPgS (100 μM). The TR-FRET signal difference (HTRF Ratio) observed between these two conditions shows that the analogue GTP-gN-octyl-thiosuccinimidyl-C2 is capable of binding to the alphai G-protein and generating a TR-FRET signal with the anti G-alphai-acceptor antibody (FIG. 27A).

Secondly, the capacity of a GPCR agonist for modulating the proportion of alpha G-protein bound to the GTP-donor was tested with the same membranes and experimental conditions mentioned above. The increase in the TR-FRET signal (HTRF Ratio) generated by stimulation with the agonist signifies that the proportion of alpha G-protein form bound to the GTP-donor increases (i.e. the empty alpha G-protein form decreases). Thus, the GPCR receptor activated by its agonist leads to binding of the GTP-donor to the G protein, which then changes to the GTP-donor form and leads to an increase in the TR-FRET signal. These results are shown in FIG. 27B (Example 25).

Example 26: Protocol for Obtaining the Anti-Protein G Alphai1 Antibodies Used in the Method According to the Invention Immunization of Mice The TST-G alphai1 recombinant protein (alphai1 G protein of sequence UniProt P63096-1, N-terminal tagged with the tag TwinStreptag (TST) (IBA) via a TEV linker) was produced in Sf9 insect cells (infection with a baculovirus encoding said protein) and then purified on an affinity column via the tag TwinStreptag (TST) (Strep-Tactin Superflow high capacity resin (IBA, Catalog: 2-1208-002)).

BALB/c mice were immunized by injection of the TST-G alphai1 protein previously diluted in buffer containing GTPgS (HEPES 20 mM pH8, NaCl 100 mM, MgCl2 3 mM, CHAPS 11 mM, GTPgS 100 μM). The primary injection was followed by three boosters at one month intervals.

Fifteen days after each injection, blood punctures on the mice allowed the presence of an immune response to be verified.

For this, an assay of the ELISA type was set up. The TST-G alphai1 protein previously diluted to 20 μg/mL in buffer containing GTPgS (Tris HCl 20 mM pH8.5, NaCl 140 mM, EDTA 2 mM, MgCl2 10 mM, BSA 0.1%, GTPgS 1 μM) was adsorbed via the tag Twin-Strep-Tag® on 96-well plates containing Strep-Tactin®XT (IBA, Catalog: 2-4101-001). For this, 100 μl of protein was added to each well and then incubated for 2 h at 37° C. followed by three washings in PBS buffer 1×, 0.05% Tween® 20.

The serial dilutions by a factor of 10 to 100 million of the blood punctures were then added at a level of 100 μL/well and incubated for 2 h at 37° C. The antibodies that were not fixed to the protein were removed by three washing steps in PBS buffer 1×, 0.05% Tween® 20 and then the fixed antibodies were detected using an anti-mouse Fc secondary antibody bound to HRP (horseradish peroxidase) (Sigma #A0168 diluted to 1/10 000 in PBS, BSA 0.1%). After incubation for 1 h at 37° C. and then three washings in PBS buffer 1×, 0.05% Tween20, development of the HRP was carried out by colorimetric assay at 450 nm following incubation of its substrate TMB (3,3',5,5'-tetramethylbenzidine, Sigma #T0440) for 20 min at room temperature with stirring.

In order to be sure that the antibodies detected by the ELISA assay were indeed directed against the alphai1 G protein and not against the tag TwinStrepTag, the same punctures were tested by ELISA assay after preincubation with an excess of another orthogonal protein tagged with TwinStrepTag (SNAPTag-TwinStrepTag). Thus, the anti-tag antibodies bind to the tagged orthogonal protein and therefore not to the alphai1 G protein attached to the bottom of the wells; in which case no HRP signal or a decrease in the HRP signal is detected.

The mice with the best antibody titers and the smallest decrease in the signal in the anti-tag control case were selected for the next step of lymphocyte hybridization, also called fusion. The spleen of the mice was recovered and a mixture of the lymphocytes and plasmocytes obtained from said spleen was fused in vitro with a myeloma cell line in the presence of a cell fusion catalyst of the polyethylene glycol type. A mutant myeloma cell line, lacking the HGPRT enzyme (Hypoxanthine Guanosine Phosphoribosyl Transferase) was used for selection of the hybrid cells, called hybridomas. These cells were cultured in a medium containing hypoxanthine, aminopterin (methotrexate) and thyamine (HAT medium) to allow removal of the unfused myeloma cells and thus select the hybridomas of interest. The unfused spleen cells die, since they are unable to proliferate in vitro. Thus, only the hybridomas survived.

These hybridomas were then cultured in culture plates. The supernatants of these hybridomas were then tested to evaluate their capacity for producing anti alphai1 G protein antibodies. For this, an ELISA assay as described above was carried out.

To evaluate the selectivity of the antibodies among the different forms of the alpahi1 G protein (full form bound to GDP vs full form bound to GTPgS vs empty form), assay was performed in parallel in conditions of TST-G alphai1 protein preincubated in the buffer containing either GDP at 1 μM, or GTPgS at 1 μM or without nucleotide. The best hybridomas were then cloned with a limiting dilution step in order to obtain hybridoma clones.

The hybridoma clones of interest were then injected in mice (intraperitoneal injection) in order to allow production of the antibodies in large amounts in the ascitic fluid.

The antibodies were then purified by affinity chromatography on columns with resins having protein A.

Capacity of the Antibodies Purified as Above for Competing for Binding to the Alpha G-Protein with the DSV36S Antibody All the reagents are diluted in TrisHCl buffer 50 mM pH 7.4, MgCl2 10 mM, BSA 0.1%, NaCl 10 mM. The Gai1 protein is prepared 2× to obtain a final concentration in the wells of 2.5 nM. The nucleotide GTPgS is prepared 2× to obtain a final concentration in the wells of 10 μM. These 2 reagents are prepared in one and the same solution and preincubated for 30 minutes at room temperature before being distributed in the wells. The antibodies purified as above are prepared 4× for final concentrations in the wells between 0.01 and 1 μM. The DSV36S-d2 antibody is prepared 4× for a final concentration of 10 nM. The anti-Twin-Strep-Tag®-Lumi4 Tb antibody is prepared 4× to obtain a final concentration in the wells of 0.5 nM.

The reagents are distributed in the 384-well plates as follows:

1. 10 μl of the preincubated mixture of ai1 G protein+GTPgS is put in each well,
2. 5 μl of the purified antibody is added to each well,
3. The plates are incubated for 30 minutes at room temperature, and
4. 5 μl of the mixture of anti-Twin-Strep-Tag®-Lumi4 Tb antibody and DSV36S-d2 antibody is added to each well.

The plates are incubated for 1 h at room temperature before reading the HTRF signal.

The antibodies according to the invention are capable of inhibiting the HTRF signal obtained with the DSV36S-d2 antibody. In contrast, the antibodies that are not according to the invention are not capable of inhibiting the signal generated by DSV36S-d2.

SEQUENCE LISTING

TABLE 3

| Sequence number | Type of sequences | Amino acid sequence |
|---|---|---|
| SEQ ID NO: 1 | Peptide KB1753 | SSRGYYHGIWVGEEGRLSR |
| SEQ ID NO: 2 | VH-CDR1 | GFNIKDYY |
| SEQ ID NO: 3 | VH-CDR2 | IDPENGNT |
| SEQ ID NO: 4 | VH-CDR3 | TRGGGYYSDWYFDV |
| SEQ ID NO: 5 | VL-CDR1 | SSVSY |
| SEQ ID NO: 6 | VL-CDR3 | QQWSSNPPIT |
| SEQ ID NO: 7 | VH-FR1 | EVQLQQSGAELVRPGALVKL SCKAS |
| SEQ ID NO: 8 | VH-FR2 | MHWVKQRPEQGLEWIGW |
| SEQ ID NO: 9 | VH-FR3 | IYDPKFQGKASITADTSSNT AYLQLSSLTSEDTAVYYC |
| SEQ ID NO: 10 | VH-FR4 | WGAGTTVTVSS |
| SEQ ID NO: 11 | VL-FR1 | QIVLTQSPAIMSASPGEKVT MTCSAS |
| SEQ ID NO: 12 | VL-FR2 | MHWYQQKSGTSPKRWIY |
| SEQ ID NO: 13 | VL-FR3 | KLASGVPARFSGSGSGTSYS LTISSMEAEDAATYYC |
| SEQ ID NO: 14 | VL-FR4 | FGAGTKLELK |
| SEQ ID NO: 15 | VH | EVQLQQSGAELVRPGALVKLSC KASGFNIKDYYMHWVKQRPEQ GLEWIGWIDPENGNTIYDPKFQ GKASITADTSSNTAYLQLSSLT SEDTAVYYCTRGGGYYSDWYF DVWGAGTTVTVSS |
| SEQ ID NO: 16 | VL | QIVLTQSPAIMSASPGEKVTMT CSASSSVSYMHWYQQKSGTSP KRWIYDTSKLASGVPARFSGSG SGTSYSLTISSMEAEDAATYYC QQWSSNPPITFGAGTKLELK |

The invention claimed is:

1. A method for determining the capacity of a molecule for modulating the activation of a G protein-coupled receptor (GPCR), said method comprising the following steps:

a) introducing, in a first container:
   - a membrane preparation bearing one or more GPCRs and one or more alpha G proteins,
   - a source of nonhydrolyzable or slowly hydrolyzable GTP labeled with a first member of a pair of resonance energy transfer (RET) partners,
   - a ligand of the alpha subunit of a G protein (alpha G-protein) labeled with a second member of the pair of RET partners, said ligand being capable of binding to the full alpha G-protein bound to the nonhydrolyzable or slowly hydrolyzable GTP labeled with the first member of a pair of RET partners,
   - optionally a GPCR agonist;

b) measuring the RET signal emitted in the first container;

c) introducing (i) in a second container, the same reagents as in step a) and the molecule to be assayed or (ii) in the first container, the molecule to be assayed;

d) measuring the RET signal emitted in the second container or in the first container obtained in step c);

e) comparing the signals obtained in steps b) and d), a modulation of the signal obtained in step d) relative to that obtained in step b) indicates that the molecule to be tested is capable of modulating the activation of the GPCR, wherein the ligand of the alpha G-protein is an antibody or an antibody fragment capable of binding to the alpha G-protein, which comprises:
   - a variable domain of a heavy chain comprising a CDR1 of amino acid sequence SEQ ID NO: 2, a CDR2 of amino acid sequence SEQ ID NO: 3, and a CDR3 of amino acid sequence SEQ ID NO: 4, and
   - a variable domain of a light chain comprising a CDR1 of amino acid sequence SEQ ID NO: 5, a CDR2 of amino acid sequence DTS, and a CDR3 of amino acid sequence SEQ ID NO: 6.

2. The method of claim 1, in which the first container does not contain a GPCR agonist and in step e) a decrease in the signal obtained in step d) relative to that obtained in step b) indicates that the molecule to be tested is a GPCR agonist.

3. The method of claim 1, in which the first container comprises a GPCR agonist and in step e):
   - an increase in the signal obtained in step d) relative to that obtained in step b) indicates that the molecule to be tested is an antagonist or a negative allosteric modulator of the GPCR; or
   - a decrease in the signal obtained in step d) relative to that obtained in step b) indicates that the molecule to be tested is an agonist or a positive allosteric modulator of the GPCR.

4. The method of claim 1, in which the first container does not comprise a GPCR agonist and in step e) an increase in the signal obtained in step d) relative to that obtained in step b) indicates that the molecule to be tested is a GPCR agonist.

5. The method of claim 1, in which the first container comprises a GPCR agonist and in step e):
   - a decrease in the signal obtained in step d) relative to that obtained in step b) indicates that the molecule to be tested is an antagonist or a negative allosteric modulator of the GPCR; or
   - an increase in the signal obtained in step d) relative to that obtained in step b) indicates that the molecule to be tested is an agonist or a positive allosteric modulator of the GPCR.

6. The method of claim 1, in which the alpha G-protein is selected from G-alphai1, G-alphai2, G-alphai3, G-alphao1, G-alphao2, G-alphaq, G-alpha12, G-alpha13, G-alphas, G-alphaz, G-alphat1, G-alphat2, G-alpha11, G-alpha14, G-alpha15, G-alpha16, and G-alphagus.

7. The method of claim 1, in which the nonhydrolyzable or slowly hydrolyzable GTP is selected from GTPgammaS, GppNHp, and GppCp.

8. The method of claim 1, in which one of the members of the pair of RET partners is a fluorescent donor compound or luminescent donor compound and the other member of the pair of RET partners is a fluorescent acceptor compound or a nonfluorescent acceptor compound.

9. The method of claim 1, in which the nonhydrolyzable or slowly hydrolyzable GTP is labeled with a fluorescent donor compound and the ligand of the alpha G-protein is labeled with a fluorescent acceptor compound or a nonfluorescent acceptor compound.

10. The method of claim 1, in which the nonhydrolyzable or slowly hydrolyzable GTP is labeled with a fluorescent acceptor compound or a nonfluorescent acceptor compound and the ligand of the alpha G-protein is labeled with a fluorescent donor compound or luminescent donor compound.

11. The method of claim 8, in which the fluorescent donor compound is a fluorescence resonance energy transfer (FRET) partner selected from: a europium cryptate, a europium chelate, a terbium chelate, a terbium cryptate, a ruthenium chelate, a quantum dot, the allophycocyanins, rhodamines, cyanins, squaraines, coumarins, proflavins, acridines, fluoresceins, derivatives of boron-dipyrromethene, and nitrobenzoxadiazole.

12. The method of claim 8, in which the fluorescent acceptor compound is a FRET partner selected from: the allophycocyanins, rhodamines, cyanins, squaraines, coumarins, proflavins, acridines, fluoresceins, derivatives of boron-dipyrromethene, nitrobenzoxadiazole, a quantum dot, GFP, GFP variants selected from GFPlO, GFP2 and eGFP, YFP, YFP variants selected from eYFP, YFP topaz, YFP citrine, YFP venus and YPet, mOrange, and DsRed.

13. The method of claim 8, in which the luminescent donor compound is a bioluminescence resonance energy transfer (BRET) partner selected from: Luciferase, Renilla Luciferase, the variants of Renilla Luciferase and Firefly Luciferase.

14. The method of claim 1, in which the nonhydrolyzable or slowly hydrolyzable GTP labeled with a first member of a pair of RET partners is a fluorescent donor compound of general formula (I): (not pictured in these proposed amendments for brevity)

in which:
   - X=0, NH or CH2;
   - Y=0, NH or CH2;
   - L is a divalent linker;
   - Ln3+ is a lanthanide complex optionally bearing a reactive group G3.

15. The method of claim 1, in which the nonhydrolyzable or slowly hydrolyzable GTP labeled with a first member of a pair of RET partners is selected from GTPgN-octyl-Cy5, GTPgN-octyl-AF488, GTPgN-L15-Fluorescein, GTPgO-Linker-Cy5 (P) and GTPgS-Linker-Cy5 (R).

16. The method of claim 1, in which the nonhydrolyzable or slowly hydrolyzable GTP labeled with a first member of a pair of RET partners is selected from GTPgNC2, GTPgN- C3, GTPgN-octyl-C2, GTPgN-octyl-C11, GTPgN-octyl-C3, GTPgO-hexyl-C2, GTPgO-hexyl-C3 and GTP-gN-octyl-thiosuccinimidyl-C2.

* * * * *